United States Patent [19]

Crystal et al.

[11] Patent Number: 6,127,525
[45] Date of Patent: *Oct. 3, 2000

[54] CHIMERIC ADENOVIRAL COAT PROTEIN AND METHODS OF USING SAME

[75] Inventors: Ronald G. Crystal, Potomac, Md.; Erik Falck-Pedersen, Dobbs Ferry; Jason Gall, New York, both of N.Y.; Imre Kovesdi, Rockville, Md.; Thomas J. Wickham, Falls Church, Va.

[73] Assignees: Cornell Research Foundation, Inc., Ithaca, N.Y.; GenVec, Inc., Rockville, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/816,346

[22] Filed: Mar. 13, 1997

Related U.S. Application Data

[63] Continuation-in-part of application No. 08/395,381, Feb. 21, 1995, Pat. No. 5,770,442.

[51] Int. Cl.[7] .......................... C07K 16/00; C07H 21/04; C12P 21/02; C12N 15/63
[52] U.S. Cl. ..................................... 530/388.22; 435/69.1; 435/69.7; 435/235.1; 435/320.1; 435/440; 530/300; 530/350; 536/24.2
[58] Field of Search .................................. 435/69.1, 69.7, 435/235.1, 320.1, 440; 536/24.2; 530/388.22, 300, 350

[56] References Cited

U.S. PATENT DOCUMENTS

| | | |
|---|---|---|
| 4,487,829 | 12/1984 | Sharp et al. . |
| 4,517,686 | 5/1985 | Ruoslahti et al. . |
| 4,578,079 | 3/1986 | Ruoslahti et al. . |
| 4,589,881 | 5/1986 | Pierschbacher et al. . |
| 4,593,002 | 6/1986 | Dulbecco . |
| 4,792,525 | 12/1988 | Ruoslahti et al. . |
| 4,797,368 | 1/1989 | Carter et al. . |
| 4,956,281 | 9/1990 | Wallner et al. . |
| 5,024,939 | 6/1991 | Gorman . |
| 5,096,815 | 3/1992 | Ladner et al. . |
| 5,166,320 | 11/1992 | Wu et al. . |
| 5,198,346 | 3/1993 | Ladner et al. . |
| 5,204,445 | 4/1993 | Plow et al. . |
| 5,223,394 | 6/1993 | Wallner . |
| 5,223,409 | 6/1993 | Ladner et al. . |
| 5,240,846 | 8/1993 | Collins et al. . |
| 5,246,921 | 9/1993 | Reddy et al. . |
| 5,332,567 | 7/1994 | Goldenberg . |
| 5,349,053 | 9/1994 | Landolfi . |
| 5,403,484 | 4/1995 | Ladner et al. . |

(List continued on next page.)

FOREIGN PATENT DOCUMENTS

| | | |
|---|---|---|
| 259212 | 3/1988 | European Pat. Off. . |
| 2078631 | 3/1990 | Japan . |
| WO 91/00360 | 1/1991 | WIPO . |
| WO 91/05805 | 5/1991 | WIPO . |
| WO 91/05871 | 5/1991 | WIPO . |
| WO 92/02553 | 2/1992 | WIPO . |
| WO 92/13081 | 8/1992 | WIPO . |
| WO 93/03769 | 3/1993 | WIPO . |
| WO 93/06223 | 4/1993 | WIPO . |
| WO 93/07282 | 4/1993 | WIPO . |

(List continued on next page.)

OTHER PUBLICATIONS

Albiges–Rizo et al., *Journal of Biological Chemistry*, 266(6), 3961–3967 (1991).
Bai et al., *Journal of Virology*, 67(9), 5198–5205 (1993).
Ball–Goodrich et al., *Virology*, 184, 175–186 (1991).
Batra et al., *Gene Therapy*, 1, 255–260 (1994).
Boursnell et al., *Gene*, 13, 311–317 (1981).
Caillet–Boudin et al., *J. Mol. Biol.*, 217, 477–486 (1991).
Chroboczek et al., *Virology*, 186, 280–285 (1992).
Chu et al., *Gene Therapy*, 1, 292–299 (1994).
Cotton et al., *Proc. Natl. Acad. Sci. USA*, 87, 4033–4037 (1990).
Cotton et al., *Proc. Natl. Acad. Sci. USA*, 89, 6094–6098 (1992).
Crystal, *Science*, 270, 404–410 (1995).
Curiel et al., *Human Gene Therapy*, 3, 147–154 (1992).
Curiel et al., *Proc. Natl. Acad. Sci. USA*, 88, 8850–8854 (1991).
Defer et al., *Journal of Virology*, 64(8), 3661–3673 (1990).
Dupuit et al., *Human Gene Therapy*, 6, 1185–1193 (1995).
Etienne–Julan et al., *Journal of General Virology*, 73, 3251–3255 (1992).
Falgout et al., *Journal of Virology*, 62(2), 622–625 (1988).
Greber et al., *Cell*, 75, 477–486 (1993).
Green et al., *EMBO Journal*, 2(8), 1357–1365 (1983).
Grubb et al., *Nature*, 371, 802–806 (1994).
Han et al., *Proc. Natl. Acad. Sci. USA*, 92, 9747–9751 (1995).
Henry et al., *Journal of Virology*, 68(8), 5239–5246 (1994).
Hong et al., *Virology*, 185(2), 758–767 (1991).
Horvath et al., *Journal of Virology*, 62(1), 341–345 (1988).
Huang et al., *Journal of Virology*, 69(4), 2257–2263 (1995).
Karayan et al., *Virology*, 202, 782–785 (1994).

(List continued on next page.)

*Primary Examiner*—David Guzo
*Assistant Examiner*—Jon Shuman
*Attorney, Agent, or Firm*—Leydig, Voit & Mayer, Ltd.

[57] ABSTRACT

The present invention provides a chimeric adenoviral coat protein (particularly a chimeric adenovirus hexon and/or fiber protein). The chimeric adenovirus coat protein has a decreased ability or inability to be recognized by a neutralizing antibody directed against the corresponding wild-type adenovirus coat protein. The invention also provides an adenovirus comprising a chimeric adenovirus coat protein, and methods of constructing and using such an adenovirus, for instance, in gene therapy.

48 Claims, 2 Drawing Sheets

U.S. PATENT DOCUMENTS

| | | | |
|---|---|---|---|
| 5,436,146 | 7/1995 | Shenk et al. . | |
| 5,443,953 | 8/1995 | Hansen et al. . | |
| 5,474,935 | 12/1995 | Chatterjee et al. . | |
| 5,521,291 | 5/1996 | Curiel et al. . | |
| 5,534,423 | 7/1996 | Palsson et al. . | |
| 5,543,328 | 8/1996 | McClelland et al. . | |
| 5,547,932 | 8/1996 | Curiel et al. . | |
| 5,552,311 | 9/1996 | Sorscher et al. . | |
| 5,559,099 | 9/1996 | Wickham et al. . | |
| 5,571,698 | 11/1996 | Ladner et al. . | |
| 5,622,699 | 4/1997 | Ruoslahti et al. | 424/93.6 |
| 5,693,509 | 12/1997 | Cotten et al. | 435/456 |
| 5,712,136 | 1/1998 | Wickham et al. | 435/456 |
| 5,731,190 | 3/1998 | Wickham et al. | 435/320.1 |
| 5,756,086 | 5/1998 | McClelland et al. | 424/93.2 |
| 5,770,442 | 6/1998 | Wickham et al. | 435/320.1 |
| 5,922,315 | 7/1999 | Roy | 424/93.2 |

FOREIGN PATENT DOCUMENTS

| | | |
|---|---|---|
| WO 93/07283 | 4/1993 | WIPO . |
| WO 94/08026 | 4/1994 | WIPO . |
| WO 94/10323 | 5/1994 | WIPO . |
| WO 94/11506 | 5/1994 | WIPO . |
| WO 94/15644 | 7/1994 | WIPO . |
| WO 94/17832 | 8/1994 | WIPO . |
| WO 94/24299 | 10/1994 | WIPO . |
| WO 94/26915 | 11/1994 | WIPO . |
| WO 95/05201 | 2/1995 | WIPO . |
| WO 95/06745 | 3/1995 | WIPO . |
| WO 95/14785 | 6/1995 | WIPO . |
| WO 95/16037 | 6/1995 | WIPO . |
| WO 95/21259 | 8/1995 | WIPO . |
| WO 95/26412 | 10/1995 | WIPO . |
| WO 95/27071 | 10/1995 | WIPO . |
| WO 95/31187 | 11/1995 | WIPO . |
| WO 95/31566 | 11/1995 | WIPO . |
| WO 96/00790 | 1/1996 | WIPO . |
| WO 96/07739 | 3/1996 | WIPO . |
| WO 96/10087 | 4/1996 | WIPO . |
| WO 96/13597 | 5/1996 | WIPO . |
| WO 96/14837 | 5/1996 | WIPO . |
| WO 96/17073 | 6/1996 | WIPO . |
| WO 96/18740 | 6/1996 | WIPO . |
| WO 97/24453 | 7/1997 | WIPO . |
| WO 97/38723 | 10/1997 | WIPO . |
| WO 98/07865 | 2/1998 | WIPO . |
| WO 98/11221 | 3/1998 | WIPO . |
| WO 98/13499 | 4/1998 | WIPO . |
| WO 98/22609 | 5/1998 | WIPO . |
| WO 98/32842 | 7/1998 | WIPO . |
| WO 98/40509 | 9/1998 | WIPO . |

OTHER PUBLICATIONS

Kass–Eisler et al., *Proc. Natl. Acad. Sci. USA*, 90, 11498–11502 (1993).
Komoriya et al., *Journal of Biological Chemistry*, 266(23), 15075–15079 (1991).
Maraveyas et al., *Acta Oncologica*, 32(7/8), 741–746 (1993).
Mastrangeli et al., *Human Gene Therapy*, 7, 79–87 (1996).
Mastrangeli et al., *Ped. Pulm., Suppl.*, 12, 230, Abst. No. 180 (1995).
Mathias et al., *Journal of Virology*, 68(10), 6811–6814 (1994).
Michael et al., presented at *Adenovirus Workshop: St. Andrews University*, p. 52 (Jul. 13–15, 1995).
Michael et al., *Gene Therapy*, 2, 660–668 (1995).
Michael et al., *Journal of Biological Chemistry*, 268(10), 6866–6869 (1993.
Miller et al., *FASEB Journal*, 9, 190–199 (1995).
Neda et al., *Journal of Biological Chemistry*, 266(22), 14143–14146 (1991).
Nemerow et al., *Biology of Vitronectins and their Receptors*, 177–184 (1993).
Nemerow et al., *Trends In Cell Biology*, 4, 52–55 (1994).
Novelli et al., *Virology*, 185, 365–376 (1991).
Orkin et al., *Report and Recommendations of the Panel to Assess the NIH Investment in Research on Gene Therapy*, (1995).
Peteranderl et al., *Biochemistry*, 31, 12272–12276 (1992).
Russell et al., *Nucleic Acids Research*, 21(5), 1081–1085 (1993).
Signas et al., *Journal of Virology*, 53(2), 672–678 (1985).
Silver et al., *Virology*, 165, 377–387 (1988).
Stewart et al., *EMBO Journal*, 12(7), 2589–2599 (1993).
Wagner et al., *Proc. Natl. Acad. Sci. USA*, 89, 6099–6103 (1992).
Watkins et al., presented at *Keystone Symposium on Molecular and Cellular Biology*, Abst. No. 336 (Taos: NM, Feb. 22–28, 1996).
Watson et al., *Journal of Virology*, 69, 525–535 (1988).
Wickham et al., *Cell*, 73, 309–319 (1993).
Wickham et al., *Gene Therapy*, 2, 750–756 (1995).
Wickham et al., *Journal of Cell Biology*, 127(1), 257–264 (1994).
Crompton et al., *J. Gen. Virol.*, 75(1), 133–139 (1994).
Crawford–Miksza et al., *J. Virol.*, 70(3), 1836–1844 (1996).
Abstract of grant application No. 1 P01 HL51746–01UB: 0004, "Gene Therapy For Cystic Fibrosis", Falck–Pedersen, submitted to the National Institutes of Health, (1994).
Bailey et al., *Virology*, 205, 439–452 (1994).
Crawford–Mikzsa et al., *Virology*, 224, 357–356 (1996).
Gall et al., *J. Virol.*, 70 (4), 2116–63 (1996).
Kass–Eisler et al., *Gene Ther.*, 3 154–62(1996).
Mautner et al., *Virology*, 131, 1–10 (1983).
Mautner et al., *Virology*, 139, 43–52, (1984).
Pring–Akerblom et al., *Virology*, 212, 232–36 (1995).
Roberts et al., *Science*, 232, 1148–51 (1986).
Verma et al., *Nature*, 389, 239–42 (1997).
Wadell, *Curr. Top. Microbiol. Immunol.*, 110, 191–220 (1984).

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
      (A) LENGTH: 2907 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
ATG GCT ACC CCT TCG ATG ATG CCG CAG TGG TCT TAC ATG CAC ATC TCG          48
Met Ala Thr Pro Ser Met Met Pro Gln Trp Ser Tyr Met His Ile Ser
 1               5                  10                  15

GGC CAG GAC GCC TCG GAG TAC CTG AGC CCC GGG CTG GTG CAG TTT GCC          96
Gly Gln Asp Ala Ser Glu Tyr Leu Ser Pro Gly Leu Val Gln Phe Ala
             20                  25                  30

CGC GCC ACC GAG ACG TAC TTC AGC CTG AAT AAC AAG TTT AGA AAC CCC         144
Arg Ala Thr Glu Thr Tyr Phe Ser Leu Asn Asn Lys Phe Arg Asn Pro
         35                  40                  45

ACG GTG GCA CCT ACG CAC GAC GTA ACC ACA GAC CGG TCC CAG CGT TTG         192
Thr Val Ala Pro Thr His Asp Val Thr Thr Asp Arg Ser Gln Arg Leu
     50                  55                  60

ACG CTG CGG TTC ATC CCT GTG GAC CGC GAG GAT ACC GCG TAC TCG TAC         240
Thr Leu Arg Phe Ile Pro Val Asp Arg Glu Asp Thr Ala Tyr Ser Tyr
 65                  70                  75                  80

AAA GCG CGG TTC ACC CTG GCT GTG GGT GAC AAC CGT GTG CTT GAT ATG         288
Lys Ala Arg Phe Thr Leu Ala Val Gly Asp Asn Arg Val Leu Asp Met
                 85                  90                  95

GCT TCC ACG TAC TTT GAC ATC CGC GGC GTG CTG GAC AGG GGG CCT ACT         336
Ala Ser Thr Tyr Phe Asp Ile Arg Gly Val Leu Asp Arg Gly Pro Thr
            100                 105                 110

TTT AAG CCC TAC TCC GGC ACT GCC TAC AAC GCT CTA GCT CCC AAG GGC         384
Phe Lys Pro Tyr Ser Gly Thr Ala Tyr Asn Ala Leu Ala Pro Lys Gly
        115                 120                 125

GCT CCT AAC TCC TGT GAG TGG GAA CAA ACC GAA GAT AGC GGC CGG GCA         432
Ala Pro Asn Ser Cys Glu Trp Glu Gln Thr Glu Asp Ser Gly Arg Ala
    130                 135                 140

GTT GCC GAG GAT GAA GAA GAG GAA GAT GAA GAT GAA GAA GAG GAA GAA         480
Val Ala Glu Asp Glu Glu Glu Glu Asp Glu Asp Glu Glu Glu Glu Glu
145                 150                 155                 160

GAA GAG CAA AAC GCT CGA GAT CAG GCT ACT AAG AAA ACA CAT GTC TAT         528
Glu Glu Gln Asn Ala Arg Asp Gln Ala Thr Lys Lys Thr His Val Tyr
                165                 170                 175

GCC CAG GCT CCT TTG TCT GGA GAA ACA ATT ACA AAA AGC GGG CTA CAA         576
Ala Gln Ala Pro Leu Ser Gly Glu Thr Ile Thr Lys Ser Gly Leu Gln
            180                 185                 190

ATA GGA TCA GAC AAT GCA GAA ACA CAA GCT AAA CCT GTA TAC GCA GAT         624
Ile Gly Ser Asp Asn Ala Glu Thr Gln Ala Lys Pro Val Tyr Ala Asp
        195                 200                 205

CCT TCC TAT CAA CCA GAA CCT CAA ATT GGC GAA TCT CAG TGG AAC GAA         672
Pro Ser Tyr Gln Pro Glu Pro Gln Ile Gly Glu Ser Gln Trp Asn Glu
    210                 215                 220

GCT GAT GCT AAT GCG GCA GGA GGG AGA GTG CTT AAA AAA ACA ACT CCC         720
Ala Asp Ala Asn Ala Ala Gly Gly Arg Val Leu Lys Lys Thr Thr Pro
225                 230                 235                 240
```

```
ATG AAA CCA TGC TAT GGA TCT TAT GCC AGG CCT ACA AAT CCT TTT GGT      768
Met Lys Pro Cys Tyr Gly Ser Tyr Ala Arg Pro Thr Asn Pro Phe Gly
            245                 250                 255

GGT CAA TCC GTT CTG GTT CCG GAT GAA AAA GGG GTG CCT CTT CCA AAG      816
Gly Gln Ser Val Leu Val Pro Asp Glu Lys Gly Val Pro Leu Pro Lys
            260                 265                 270

GTT GAC TTG CAA TTC TTC TCA AAT ACT ACC TCT TTG AAC GAC CGG CAA      864
Val Asp Leu Gln Phe Phe Ser Asn Thr Thr Ser Leu Asn Asp Arg Gln
            275                 280                 285

GGC AAT GCT ACT AAA CCA AAA GTG GTT TTG TAC AGT GAA GAT GTA AAT      912
Gly Asn Ala Thr Lys Pro Lys Val Val Leu Tyr Ser Glu Asp Val Asn
290                 295                 300

ATG GAA ACC CCA GAC ACA CAT CTG TCT TAC AAA CCT GGA AAA GGT GAT      960
Met Glu Thr Pro Asp Thr His Leu Ser Tyr Lys Pro Gly Lys Gly Asp
305                 310                 315                 320

GAA AAT TCT AAA GCT ATG TTG GGT CAA CAA TCT ATG CCA AAC AGA CCC     1008
Glu Asn Ser Lys Ala Met Leu Gly Gln Gln Ser Met Pro Asn Arg Pro
                325                 330                 335

AAT TAC ATT GCT TTC AGG GAC AAT TTT ATT GGC CTA ATG TAT TAT AAC     1056
Asn Tyr Ile Ala Phe Arg Asp Asn Phe Ile Gly Leu Met Tyr Tyr Asn
                340                 345                 350

AGC ACT GGC AAC ATG GGT GTT CTT GCT GGT CAG GCA TCG CAG CTA AAT     1104
Ser Thr Gly Asn Met Gly Val Leu Ala Gly Gln Ala Ser Gln Leu Asn
            355                 360                 365

GCC GTG GTA GAT TTG CAA GAC AGA AAC ACA GAG CTG TCC TAT CAA CTC     1152
Ala Val Val Asp Leu Gln Asp Arg Asn Thr Glu Leu Ser Tyr Gln Leu
            370                 375                 380

TTG CTT GAT TCC ATA GGT GAT AGA ACC AGA TAT TTT TCT ATG TGG AAT     1200
Leu Leu Asp Ser Ile Gly Asp Arg Thr Arg Tyr Phe Ser Met Trp Asn
385                 390                 395                 400

CAG GCT GTA GAC AGC TAT GAT CCA GAT GTT AGA ATC ATT GAA AAC CAT     1248
Gln Ala Val Asp Ser Tyr Asp Pro Asp Val Arg Ile Ile Glu Asn His
                405                 410                 415

GGA ACT GAG GAT GAA TTG CCA AAT TAT TGT TTT CCT CTT GGG GGT ATT     1296
Gly Thr Glu Asp Glu Leu Pro Asn Tyr Cys Phe Pro Leu Gly Gly Ile
                420                 425                 430

GGG GTA ACT GAC ACC TAT CAA GCT ATT AAG GCT AAT GGC AAT GGC TCA     1344
Gly Val Thr Asp Thr Tyr Gln Ala Ile Lys Ala Asn Gly Asn Gly Ser
            435                 440                 445

GGC GAT AAT GGA GAT ACT ACA TGG ACA AAA GAT GAA ACT TTT GCA ACA     1392
Gly Asp Asn Gly Asp Thr Thr Trp Thr Lys Asp Glu Thr Phe Ala Thr
            450                 455                 460

CGT AAT GAA ATA GGA GTG GGT AAC AAC TTT GCC ATG GAA ATT AAC CTA     1440
Arg Asn Glu Ile Gly Val Gly Asn Asn Phe Ala Met Glu Ile Asn Leu
465                 470                 475                 480

AAT GCC AAC CTA TGG AGA AAT TTC CTT TAC TCC AAT ATT GCG CTG TAC     1488
Asn Ala Asn Leu Trp Arg Asn Phe Leu Tyr Ser Asn Ile Ala Leu Tyr
                485                 490                 495

CTG CCA GAC AAG CTA AAA TAC AAC CCC ACC AAT GTG GAA ATA TCT GAC     1536
Leu Pro Asp Lys Leu Lys Tyr Asn Pro Thr Asn Val Glu Ile Ser Asp
                500                 505                 510

AAC CCC AAC ACC TAC GAC TAC ATG AAC AAG CGA GTG GTG GCT CCC GGG     1584
Asn Pro Asn Thr Tyr Asp Tyr Met Asn Lys Arg Val Val Ala Pro Gly
            515                 520                 525

CTT GTA GAC TGC TAC ATT AAC CTT GGG GCG CGC TGG TCT CTG GAC TAC     1632
Leu Val Asp Cys Tyr Ile Asn Leu Gly Ala Arg Trp Ser Leu Asp Tyr
            530                 535                 540
```

```
ATG GAC AAC GTT AAT CCC TTT AAC CAC CAC CGC AAT GCG GGC CTC CGT         1680
Met Asp Asn Val Asn Pro Phe Asn His His Arg Asn Ala Gly Leu Arg
545                 550                 555                 560

TAT CGC TCC ATG TTG TTG GGA AAC GGC CGC TAC GTG CCC TTT CAC ATT         1728
Tyr Arg Ser Met Leu Leu Gly Asn Gly Arg Tyr Val Pro Phe His Ile
                565                 570                 575

CAG GTG CCC CAA AAG TTT TTT GCC ATT AAA AAC CTC CTC CTC CTG CCA         1776
Gln Val Pro Gln Lys Phe Phe Ala Ile Lys Asn Leu Leu Leu Leu Pro
            580                 585                 590

GGC TCA TAT ACA TAT GAA TGG AAC TTC AGG AAG GAT GTT AAC ATG GTT         1824
Gly Ser Tyr Thr Tyr Glu Trp Asn Phe Arg Lys Asp Val Asn Met Val
        595                 600                 605

CTG CAG AGC TCT CTG GGA AAC GAT CTT AGA GTT GAC GGG GCT AGC ATT         1872
Leu Gln Ser Ser Leu Gly Asn Asp Leu Arg Val Asp Gly Ala Ser Ile
610                 615                 620

AAG TTT GAC AGC ATT TGT CTT TAC GCC ACC TTC TTC CCC ATG GCC CAC         1920
Lys Phe Asp Ser Ile Cys Leu Tyr Ala Thr Phe Phe Pro Met Ala His
625                 630                 635                 640

AAC ACG GCC TCC ACG CTG GAA GCC ATG CTC AGA AAT GAC ACC AAC GAC         1968
Asn Thr Ala Ser Thr Leu Glu Ala Met Leu Arg Asn Asp Thr Asn Asp
                645                 650                 655

CAG TCC TTT AAT GAC TAC CTT TCC GCC GCC AAC ATG CTA TAC CCC ATA         2016
Gln Ser Phe Asn Asp Tyr Leu Ser Ala Ala Asn Met Leu Tyr Pro Ile
            660                 665                 670

CCC GCC AAC GCC ACC AAC GTG CCC ATC TCC ATC CCA TCG CGC AAC TGG         2064
Pro Ala Asn Ala Thr Asn Val Pro Ile Ser Ile Pro Ser Arg Asn Trp
        675                 680                 685

GCA GCA TTT CGC GGT TGG GCC TTC ACA CGC TTG AAG ACA AAG GAA ACC         2112
Ala Ala Phe Arg Gly Trp Ala Phe Thr Arg Leu Lys Thr Lys Glu Thr
    690                 695                 700

CCT TCC CTG GGA TCA GGC TAC GAC CCT TAC TAC ACC TAC TCT GGC TCC         2160
Pro Ser Leu Gly Ser Gly Tyr Asp Pro Tyr Tyr Thr Tyr Ser Gly Ser
705                 710                 715                 720

ATA CCA TAC CTT GAC GGA ACC TTC TAT CTT AAT CAC ACC TTT AAG AAG         2208
Ile Pro Tyr Leu Asp Gly Thr Phe Tyr Leu Asn His Thr Phe Lys Lys
                725                 730                 735

GTG GCC ATT ACC TTT GAC TCT TCT GTT AGC TGG CCG GGC AAC GAC CGC         2256
Val Ala Ile Thr Phe Asp Ser Ser Val Ser Trp Pro Gly Asn Asp Arg
            740                 745                 750

CTG CTT ACT CCC AAT GAG TTT GAG ATT AAA CGC TCA GTT GAC GGG GAG         2304
Leu Leu Thr Pro Asn Glu Phe Glu Ile Lys Arg Ser Val Asp Gly Glu
        755                 760                 765

GGC TAC AAC GTA GCT CAG TGC AAC ATG ACC AAG GAC TGG TTC CTG GTG         2352
Gly Tyr Asn Val Ala Gln Cys Asn Met Thr Lys Asp Trp Phe Leu Val
    770                 775                 780

CAG ATG TTG GCC AAC TAC AAT ATT GGC TAC CAG GGC TTC TAC ATT CCA         2400
Gln Met Leu Ala Asn Tyr Asn Ile Gly Tyr Gln Gly Phe Tyr Ile Pro
785                 790                 795                 800

GAA AGC TAC AAG GAC CGC ATG TAC TCG TTC TTC AGA AAC TTC CAG CCC         2448
Glu Ser Tyr Lys Asp Arg Met Tyr Ser Phe Phe Arg Asn Phe Gln Pro
                805                 810                 815

ATG AGC CGG CAA GTG GTT GAC GAT ACT AAA TAC AAG GAG TAT CAG CAG         2496
Met Ser Arg Gln Val Val Asp Asp Thr Lys Tyr Lys Glu Tyr Gln Gln
            820                 825                 830

GTT GGA ATT CTT CAC CAG CAT AAC AAC TCA GGA TTC GTA GGC TAC CTC         2544
Val Gly Ile Leu His Gln His Asn Asn Ser Gly Phe Val Gly Tyr Leu
        835                 840                 845

GCT CCC ACC ATG CGC GAG GGA CAG GCT TAC CCC GCC AAC GTG CCC TAC         2592
Ala Pro Thr Met Arg Glu Gly Gln Ala Tyr Pro Ala Asn Val Pro Tyr
    850                 855                 860
```

-continued

```
CCA CTA ATA GGC AAA ACC GCG GTT GAC AGT ATT ACC CAG AAA AAG TTT      2640
Pro Leu Ile Gly Lys Thr Ala Val Asp Ser Ile Thr Gln Lys Lys Phe
865             870                 875                 880

CTT TGC GAT CGC ACC CTT TGG CGC ATC CCA TTC TCC AGT AAC TTT ATG      2688
Leu Cys Asp Arg Thr Leu Trp Arg Ile Pro Phe Ser Ser Asn Phe Met
                885                 890                 895

TCC ATG GGC GCA CTC ACA GAC CTG GGC CAA AAC CTT CTC TAC GCC AAC      2736
Ser Met Gly Ala Leu Thr Asp Leu Gly Gln Asn Leu Leu Tyr Ala Asn
            900                 905                 910

TCC GCC CAC GCG CTA GAC ATG ACT TTT GAG GTG GAT CCC ATG GAC GAG      2784
Ser Ala His Ala Leu Asp Met Thr Phe Glu Val Asp Pro Met Asp Glu
        915                 920                 925

CCC ACC CTT CTT TAT GTT TTG TTT GAA GTC TTT GAC GTG GTC CGT GTG      2832
Pro Thr Leu Leu Tyr Val Leu Phe Glu Val Phe Asp Val Val Arg Val
    930                 935                 940

CAC CAG CCG CAC CGC GGC GTC ATC GAG ACC GTG TAC CTG CGC ACG CCC      2880
His Gln Pro His Arg Gly Val Ile Glu Thr Val Tyr Leu Arg Thr Pro
945                 950                 955                 960

TTC TCG GCC GGC AAC GCC ACA ACA TAA                                  2907
Phe Ser Ala Gly Asn Ala Thr Thr
                965
```

(2) INFORMATION FOR SEQ ID NO:2:

(i) SEQUENCE CHARACTERISTICS:
        (A) LENGTH: 968 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Ser Cys Glu Trp Glu Gln Thr Glu Asp Ser Gly Arg Ala
    130                 135                 140

Val Ala Glu Asp Glu Glu Glu Asp Glu Asp Glu Glu Glu Glu Glu Glu
145                 150                 155                 160

Glu Glu Gln Asn Ala Arg Asp Gln Ala Thr Lys Lys Thr His Val Tyr
                165                 170                 175

Ala Gln Ala Pro Leu Ser Gly Glu Thr Ile Thr Lys Ser Gly Leu Gln
            180                 185                 190

Ile Gly Ser Asp Asn Ala Glu Thr Gln Ala Lys Pro Val Tyr Ala Asp
        195                 200                 205
```

-continued

```
Pro Ser Tyr Gln Pro Glu Pro Gln Ile Gly Glu Ser Gln Trp Asn Glu
    210                 215                 220
Ala Asp Ala Asn Ala Ala Gly Gly Arg Val Leu Lys Lys Thr Thr Pro
225                 230                 235                 240
Met Lys Pro Cys Tyr Gly Ser Tyr Ala Arg Pro Thr Asn Pro Phe Gly
            245                 250                 255
Gly Gln Ser Val Leu Val Pro Asp Glu Lys Gly Val Pro Leu Pro Lys
                260                 265                 270
Val Asp Leu Gln Phe Phe Ser Asn Thr Thr Ser Leu Asn Asp Arg Gln
                275                 280                 285
Gly Asn Ala Thr Lys Pro Lys Val Val Leu Tyr Ser Glu Asp Val Asn
    290                 295                 300
Met Glu Thr Pro Asp Thr His Leu Ser Tyr Lys Pro Gly Lys Gly Asp
305                 310                 315                 320
Glu Asn Ser Lys Ala Met Leu Gly Gln Gln Ser Met Pro Asn Arg Pro
                325                 330                 335
Asn Tyr Ile Ala Phe Arg Asp Asn Phe Ile Gly Leu Met Tyr Tyr Asn
                340                 345                 350
Ser Thr Gly Asn Met Gly Val Leu Ala Gly Gln Ala Ser Gln Leu Asn
            355                 360                 365
Ala Val Val Asp Leu Gln Asp Arg Asn Thr Glu Leu Ser Tyr Gln Leu
    370                 375                 380
Leu Leu Asp Ser Ile Gly Asp Arg Thr Arg Tyr Phe Ser Met Trp Asn
385                 390                 395                 400
Gln Ala Val Asp Ser Tyr Asp Pro Asp Val Arg Ile Ile Glu Asn His
                405                 410                 415
Gly Thr Glu Asp Glu Leu Pro Asn Tyr Cys Phe Pro Leu Gly Gly Ile
                420                 425                 430
Gly Val Thr Asp Thr Tyr Gln Ala Ile Lys Ala Asn Gly Asn Gly Ser
            435                 440                 445
Gly Asp Asn Gly Asp Thr Thr Trp Thr Lys Asp Glu Thr Phe Ala Thr
    450                 455                 460
Arg Asn Glu Ile Gly Val Gly Asn Asn Phe Ala Met Glu Ile Asn Leu
465                 470                 475                 480
Asn Ala Asn Leu Trp Arg Asn Phe Leu Tyr Ser Asn Ile Ala Leu Tyr
                485                 490                 495
Leu Pro Asp Lys Leu Lys Tyr Asn Pro Thr Asn Val Glu Ile Ser Asp
                500                 505                 510
Asn Pro Asn Thr Tyr Asp Tyr Met Asn Lys Arg Val Val Ala Pro Gly
            515                 520                 525
Leu Val Asp Cys Tyr Ile Asn Leu Gly Ala Arg Trp Ser Leu Asp Tyr
    530                 535                 540
Met Asp Asn Val Asn Pro Phe Asn His His Arg Asn Ala Gly Leu Arg
545                 550                 555                 560
Tyr Arg Ser Met Leu Leu Gly Asn Gly Arg Tyr Val Pro Phe His Ile
            565                 570                 575
Gln Val Pro Gln Lys Phe Phe Ala Ile Lys Asn Leu Leu Leu Leu Pro
                580                 585                 590
Gly Ser Tyr Thr Tyr Glu Trp Asn Phe Arg Lys Asp Val Asn Met Val
            595                 600                 605
Leu Gln Ser Ser Leu Gly Asn Asp Leu Arg Val Asp Gly Ala Ser Ile
    610                 615                 620
```

```
Lys Phe Asp Ser Ile Cys Leu Tyr Ala Thr Phe Pro Met Ala His
625                 630                 635                 640

Asn Thr Ala Ser Thr Leu Glu Ala Met Leu Arg Asn Asp Thr Asn Asp
                645                 650                 655

Gln Ser Phe Asn Asp Tyr Leu Ser Ala Ala Asn Met Leu Tyr Pro Ile
                660                 665                 670

Pro Ala Asn Ala Thr Asn Val Pro Ile Ser Ile Pro Ser Arg Asn Trp
            675                 680                 685

Ala Ala Phe Arg Gly Trp Ala Phe Thr Arg Leu Lys Thr Lys Glu Thr
        690                 695                 700

Pro Ser Leu Gly Ser Gly Tyr Asp Pro Tyr Tyr Thr Tyr Ser Gly Ser
705                 710                 715                 720

Ile Pro Tyr Leu Asp Gly Thr Phe Tyr Leu Asn His Thr Phe Lys Lys
                725                 730                 735

Val Ala Ile Thr Phe Asp Ser Ser Val Ser Trp Pro Gly Asn Asp Arg
            740                 745                 750

Leu Leu Thr Pro Asn Glu Phe Glu Ile Lys Arg Ser Val Asp Gly Glu
        755                 760                 765

Gly Tyr Asn Val Ala Gln Cys Asn Met Thr Lys Asp Trp Phe Leu Val
770                 775                 780

Gln Met Leu Ala Asn Tyr Asn Ile Gly Tyr Gln Gly Phe Tyr Ile Pro
785                 790                 795                 800

Glu Ser Tyr Lys Asp Arg Met Tyr Ser Phe Phe Arg Asn Phe Gln Pro
                805                 810                 815

Met Ser Arg Gln Val Val Asp Thr Lys Tyr Lys Glu Tyr Gln Gln
            820                 825                 830

Val Gly Ile Leu His Gln His Asn Asn Ser Gly Phe Val Gly Tyr Leu
        835                 840                 845

Ala Pro Thr Met Arg Glu Gly Gln Ala Tyr Pro Ala Asn Val Pro Tyr
850                 855                 860

Pro Leu Ile Gly Lys Thr Ala Val Asp Ser Ile Thr Gln Lys Lys Phe
865                 870                 875                 880

Leu Cys Asp Arg Thr Leu Trp Arg Ile Pro Phe Ser Ser Asn Phe Met
                885                 890                 895

Ser Met Gly Ala Leu Thr Asp Leu Gly Gln Asn Leu Leu Tyr Ala Asn
            900                 905                 910

Ser Ala His Ala Leu Asp Met Thr Phe Glu Val Asp Pro Met Asp Glu
        915                 920                 925

Pro Thr Leu Leu Tyr Val Leu Phe Glu Val Phe Asp Val Val Arg Val
930                 935                 940

His Gln Pro His Arg Gly Val Ile Glu Thr Val Tyr Leu Arg Thr Pro
945                 950                 955                 960

Phe Ser Ala Gly Asn Ala Thr Thr (2) INFORMATION FOR SEQ ID NO:3:

(i) SEQUENCE CHARACTERISTICS:
        (A) LENGTH: 2858 base pairs
        (B) TYPE: nucleic acid
        (C) STRANDEDNESS: double
        (D) TOPOLOGY: linear (ii) MOLECULE TYPE: DNA (genomic)
```

(ix) FEATURE:
   (A) NAME/KEY: misc_feature
   (B) LOCATION: 951, 952
   (D) OTHER INFORMATION: /note="Xaa can be either Gln, His, or Thr"

(xi) SEQUENCE DESCRIPTION: SEQ ID NO:3:

| | | |
|---|---|---|
| ATG GCT ACC CCT TCG ATG ATG CCG CAG TGG TCT TAC ATG CAC ATC TCG | 48 | |
| Met Ala Thr Pro Ser Met Met Pro Gln Trp Ser Tyr Met His Ile Ser | | |
| 1               5                   10                  15 | | |
| GGC CAG GAC GCC TCG GAG TAC CTG AGC CCC GGG CTG GTG CAG TTT GCC | 96 | |
| Gly Gln Asp Ala Ser Glu Tyr Leu Ser Pro Gly Leu Val Gln Phe Ala | | |
|             20                  25                  30 | | |
| CGC GCC ACC GAG ACG TAC TTC AGC CTG AAT AAC AAG TTT AGA AAC CCC | 144 | |
| Arg Ala Thr Glu Thr Tyr Phe Ser Leu Asn Asn Lys Phe Arg Asn Pro | | |
|         35                  40                  45 | | |
| ACG GTG GCG CCT ACG CAC GAC GTG ACC ACA GAC CGG TCC CAG CGT TTG | 192 | |
| Thr Val Ala Pro Thr His Asp Val Thr Thr Asp Arg Ser Gln Arg Leu | | |
|     50                  55                  60 | | |
| ACG CTG CGG TTC ATC CCT GTG GAC CGT GAG GAT ACT GCG TAC TCG TAC | 240 | |
| Thr Leu Arg Phe Ile Pro Val Asp Arg Glu Asp Thr Ala Tyr Ser Tyr | | |
| 65                  70                  75                  80 | | |
| AAG GCG CGG TTC ACC CTA GCT GTG GGT GAT AAC CGT GTG CTG GAC ATG | 288 | |
| Lys Ala Arg Phe Thr Leu Ala Val Gly Asp Asn Arg Val Leu Asp Met | | |
|                 85                  90                  95 | | |
| GCT TCC ACG TAC TTT GAC ATC CGC GGC GTG CTG GAC AGG GGC CCT ACT | 336 | |
| Ala Ser Thr Tyr Phe Asp Ile Arg Gly Val Leu Asp Arg Gly Pro Thr | | |
|             100                 105                 110 | | |
| TTT AAG CCC TAC TCT GGC ACT GCC TAC AAC GCC CTG GCT CCC AAG GGT | 384 | |
| Phe Lys Pro Tyr Ser Gly Thr Ala Tyr Asn Ala Leu Ala Pro Lys Gly | | |
|         115                 120                 125 | | |
| GCC CCA AAT CCT TGC GAA TGG GAT GAA GCT GCT ACT GCT CTT GAA ATA | 432 | |
| Ala Pro Asn Pro Cys Glu Trp Asp Glu Ala Ala Thr Ala Leu Glu Ile | | |
|     130                 135                 140 | | |
| AAC CTA GAA GAA GAG GAC GAT GAC AAC GAA GAC GAA GTA GAC GAG CAA | 480 | |
| Asn Leu Glu Glu Glu Asp Asp Asp Asn Glu Asp Glu Val Asp Glu Gln | | |
| 145                 150                 155                 160 | | |
| GCT GAG CAG CAA AAA ACT CAC GTA TTT GGG CAG GCG CCT TAT TCT GGT | 528 | |
| Ala Glu Gln Gln Lys Thr His Val Phe Gly Gln Ala Pro Tyr Ser Gly | | |
|                 165                 170                 175 | | |
| ATA AAT ATT ACA AAG GAG GGT ATT CAA ATA GGT GTC GAA GGT CAA ACA | 576 | |
| Ile Asn Ile Thr Lys Glu Gly Ile Gln Ile Gly Val Glu Gly Gln Thr | | |
|             180                 185                 190 | | |
| CCT AAA TAT GCC GAT AAA ACA TTT CAA CCT GAA CCT CAA ATA GGA GAA | 624 | |
| Pro Lys Tyr Ala Asp Lys Thr Phe Gln Pro Glu Pro Gln Ile Gly Glu | | |
|         195                 200                 205 | | |
| TCT CAG TGG TAC GAA ACT GAA ATT AAT CAT GCA GCT GGG AGA GTC CTT | 672 | |
| Ser Gln Trp Tyr Glu Thr Glu Ile Asn His Ala Ala Gly Arg Val Leu | | |
|     210                 215                 220 | | |
| AAA AAG ACT ACC CCA ATG AAA CCA TGT TAC GGT TCA TAT GCA AAA CCC | 720 | |
| Lys Lys Thr Thr Pro Met Lys Pro Cys Tyr Gly Ser Tyr Ala Lys Pro | | |
| 225                 230                 235                 240 | | |
| ACA AAT GAA AAT GGA GGG CAA GGC ATT CTT GTA AAG CAA CAA AAT GGA | 768 | |
| Thr Asn Glu Asn Gly Gly Gln Gly Ile Leu Val Lys Gln Gln Asn Gly | | |
|                 245                 250                 255 | | |
| AAG CTA GAA AGT CAA GTG GAA ATG CAA TTT TTC TCA ACT ACT GAG GCG | 816 | |
| Lys Leu Glu Ser Gln Val Glu Met Gln Phe Phe Ser Thr Thr Glu Ala | | |
|             260                 265                 270 | | |
| ACC GCA GGC AAT GGT GAT AAC TTG ACT CCT AAA GTG GTA TTG TAC AGT | 864 | |
| Thr Ala Gly Asn Gly Asp Asn Leu Thr Pro Lys Val Val Leu Tyr Ser | | |
|         275                 280                 285 | | |

-continued

| | |
|---|---|
| GAA GAT GTA GAT ATA GAA ACC CCA GAC ACT CAT ATT TCT TAC ATG CCC<br>Glu Asp Val Asp Ile Glu Thr Pro Asp Thr His Ile Ser Tyr Met Pro<br>290                                    295                        300 | 912 |
| ACT ATT AAG GAA GGT AAC TCA CGA GAA CTA ATG GGC CAA CAA TCT ATG<br>Thr Ile Lys Glu Gly Asn Ser Arg Glu Leu Met Gly Gln Gln Ser Met<br>305                             310                         315                  320 | 960 |
| CCC AAC AGG CCT AAT TAC ATT GCT TTT AGG GAC AAT TTT ATT GGT CTA<br>Pro Asn Arg Pro Asn Tyr Ile Ala Phe Arg Asp Asn Phe Ile Gly Leu<br>                        325                         330                        335 | 1008 |
| ATG TAT TAC AAC AGC ACG GGT AAT ATG GGT GTT CTG GCG GGC CAA GCA<br>Met Tyr Tyr Asn Ser Thr Gly Asn Met Gly Val Leu Ala Gly Gln Ala<br>                  340                         345                        350 | 1056 |
| TCG CAG TTG AAT GCT GTT GTA GAT TTG CAA GAC AGA AAC ACA GAG CTT<br>Ser Gln Leu Asn Ala Val Val Asp Leu Gln Asp Arg Asn Thr Glu Leu<br>             355                         360                        365 | 1104 |
| TCA TAC CAG CTT TTG CTT GAT TCC ATT GGT GAT AGA ACC AGG TAC TTT<br>Ser Tyr Gln Leu Leu Leu Asp Ser Ile Gly Asp Arg Thr Arg Tyr Phe<br>370                                    375                        380 | 1152 |
| TCT ATG TGG AAT CAG GCT GTT GAC AGC TAT GAT CCA GAT GTT AGA ATT<br>Ser Met Trp Asn Gln Ala Val Asp Ser Tyr Asp Pro Asp Val Arg Ile<br>385                                  390                         395                  400 | 1200 |
| ATT GAA AAT CAT GGA ACT GAA GAT GAA CTT CCA AAT TAC TGC TTT CCA<br>Ile Glu Asn His Gly Thr Glu Asp Glu Leu Pro Asn Tyr Cys Phe Pro<br>                  405                         410                        415 | 1248 |
| CTG GGA GGT GTG ATT AAT ACA GAG ACT CTT ACC AAG GTA AAA CCT AAA<br>Leu Gly Gly Val Ile Asn Thr Glu Thr Leu Thr Lys Val Lys Pro Lys<br>             420                         425                        430 | 1296 |
| ACA GGT CAG GAA AAT GGA TGG GAA AAA GAT GCT ACA GAA TTT TCA GAT<br>Thr Gly Gln Glu Asn Gly Trp Glu Lys Asp Ala Thr Glu Phe Ser Asp<br>                  435                         440                        445 | 1344 |
| AAA AAT GAA ATA AGA GTT GGA AAT AAT TTT GCC ATG GAA ATC AAT CTA<br>Lys Asn Glu Ile Arg Val Gly Asn Asn Phe Ala Met Glu Ile Asn Leu<br>450                                  455                        460 | 1392 |
| AAT GCC AAC CTG TGG AGA AAT TTC CTG TAC TCC AAC ATA GCG CTG TAT<br>Asn Ala Asn Leu Trp Arg Asn Phe Leu Tyr Ser Asn Ile Ala Leu Tyr<br>465                                  470                        475                  480 | 1440 |
| TTG CCC GAC AAG CTA AAG TAC AGT CCT TCC AAC GTA AAA ATT TCT GAT<br>Leu Pro Asp Lys Leu Lys Tyr Ser Pro Ser Asn Val Lys Ile Ser Asp<br>                  485                         490                        495 | 1488 |
| AAC CCA AAC ACC TAC GAC TAC ATG AAC AAG CGA GTG GTG GCT CCC GGG<br>Asn Pro Asn Thr Tyr Asp Tyr Met Asn Lys Arg Val Val Ala Pro Gly<br>             500                         505                        510 | 1536 |
| TTA GTG GAC TGC TAC ATT AAC CTT GGA GCA CGC TGG TCC CTT GAC TAT<br>Leu Val Asp Cys Tyr Ile Asn Leu Gly Ala Arg Trp Ser Leu Asp Tyr<br>                  515                         520                        525 | 1584 |
| ATG GAC AAC GTC AAC CCA TTT AAC CAC CAC CGC AAT GCT GGC CTG CGC<br>Met Asp Asn Val Asn Pro Phe Asn His His Arg Asn Ala Gly Leu Arg<br>530                                  535                        540 | 1632 |
| TAC CGC TCA ATG TTG CTG GGC AAT GGT CGC TAT GTG CCC TTC CAC ATC<br>Tyr Arg Ser Met Leu Leu Gly Asn Gly Arg Tyr Val Pro Phe His Ile<br>545                                  550                        555                  560 | 1680 |
| CAG GTG CCT CAG AAG TTC TTT GCC ATT AAA AAC CTC CTT CTC CTG CCG<br>Gln Val Pro Gln Lys Phe Phe Ala Ile Lys Asn Leu Leu Leu Leu Pro<br>                  565                         570                        575 | 1728 |
| GGC TCA TAC ACC TAC GAG TGG AAC TTC AGG AAG GAT GTT AAC ATG GTT<br>Gly Ser Tyr Thr Tyr Glu Trp Asn Phe Arg Lys Asp Val Asn Met Val<br>             580                         585                        590 | 1776 |

```
CTG CAG AGC TCC CTA GGA AAT GAC CTA AGG GTT GAC GGA GCC AGC ATT    1824
Leu Gln Ser Ser Leu Gly Asn Asp Leu Arg Val Asp Gly Ala Ser Ile
        595                 600                 605

AAG TTT GAT AGC ATT TGC CTT TAC GCC ACC TTC TTC CCC ATG GCC CAC    1872
Lys Phe Asp Ser Ile Cys Leu Tyr Ala Thr Phe Phe Pro Met Ala His
610                 615                 620

AAC ACC GCC TCC ACG CTT GAG GCC ATG CTT AGA AAC GAC ACC AAC GAC    1920
Asn Thr Ala Ser Thr Leu Glu Ala Met Leu Arg Asn Asp Thr Asn Asp
625                 630                 635                 640

CAG TCC TTT AAC GAC TAT CTC TCC GCC GCC AAC ATG CTC TAC CCT ATA    1968
Gln Ser Phe Asn Asp Tyr Leu Ser Ala Ala Asn Met Leu Tyr Pro Ile
            645                 650                 655

CCC GCC AAC GCT ACC AAC GTG CCC ATA TCC ATC CCC TCC CGC AAC TGG    2016
Pro Ala Asn Ala Thr Asn Val Pro Ile Ser Ile Pro Ser Arg Asn Trp
        660                 665                 670

GCG GCT TTC CGC GGC TGG GCC TTC ACG CGC CTT AAG ACT AAG GAA ACC    2064
Ala Ala Phe Arg Gly Trp Ala Phe Thr Arg Leu Lys Thr Lys Glu Thr
    675                 680                 685

CCA TCA CTG GGC TCG GGC TAC GAC CCT TAT TAC ACC TAC TCT GGC TCT    2112
Pro Ser Leu Gly Ser Gly Tyr Asp Pro Tyr Tyr Thr Tyr Ser Gly Ser
690                 695                 700

ATA CCC TAC CTA GAT GGA ACC TTT TAC CTC AAC CAC ACC TTT AAG AAG    2160
Ile Pro Tyr Leu Asp Gly Thr Phe Tyr Leu Asn His Thr Phe Lys Lys
705                 710                 715                 720

GTG GCC ATT ACC TTT GAC TCT TCT GTC AGC TGG CCT GGC AAT GAC CGC    2208
Val Ala Ile Thr Phe Asp Ser Ser Val Ser Trp Pro Gly Asn Asp Arg
            725                 730                 735

CTG CTT ACC CCC AAC GAG TTT GAA ATT AAG CGC TCA GTT GAC GGG GAG    2256
Leu Leu Thr Pro Asn Glu Phe Glu Ile Lys Arg Ser Val Asp Gly Glu
        740                 745                 750

GGT TAC AAC GTT GCC CAG TGT AAC ATG ACC AAA GAC TGG TTC CTG GTA    2304
Gly Tyr Asn Val Ala Gln Cys Asn Met Thr Lys Asp Trp Phe Leu Val
    755                 760                 765

CAA ATG CTA GCT AAC TAC AAC ATT GGC TAC CAG GGC TTC TAT ATC CCA    2352
Gln Met Leu Ala Asn Tyr Asn Ile Gly Tyr Gln Gly Phe Tyr Ile Pro
770                 775                 780

GAG AGC TAC AAG GAC CGC ATG TAC TCC TTC TTT AGA AAC TTC CAG CCC    2400
Glu Ser Tyr Lys Asp Arg Met Tyr Ser Phe Phe Arg Asn Phe Gln Pro
785                 790                 795                 800

ATG AGC CGT CAG GTG GTG GAT GAT ACT AAA TAC AAG GAC TAC CAA CAG    2448
Met Ser Arg Gln Val Val Asp Asp Thr Lys Tyr Lys Asp Tyr Gln Gln
            805                 810                 815

GTG GGC ATC CTA CAC CAA CAC AAC AAC TCT GGA TTT GTT GGC TAC CTT    2496
Val Gly Ile Leu His Gln His Asn Asn Ser Gly Phe Val Gly Tyr Leu
        820                 825                 830

GCC CCC ACC ATG CGC GAA GGA CAG GCC TAC CCT GCT AAC TTC CCC TAT    2544
Ala Pro Thr Met Arg Glu Gly Gln Ala Tyr Pro Ala Asn Phe Pro Tyr
    835                 840                 845

CCG CTT ATA GGC AAG ACC GCA GTT GAC AGC ATT ACC CAG AAA AAG TTT    2592
Pro Leu Ile Gly Lys Thr Ala Val Asp Ser Ile Thr Gln Lys Lys Phe
850                 855                 860

CTT TGC GAT CGC ACC CTT TGG CGC ATC CCA TTC TCC AGT AAC TTT ATG    2640
Leu Cys Asp Arg Thr Leu Trp Arg Ile Pro Phe Ser Ser Asn Phe Met
865                 870                 875                 880

TCC ATG GGC GCA CTC ACA GAC CTG GGC CAA AAC CTT CTC TAC GCC AAC    2688
Ser Met Gly Ala Leu Thr Asp Leu Gly Gln Asn Leu Leu Tyr Ala Asn
            885                 890                 895

TCC GCC CAC GCG CTA GAC ATG ACT TTT GAG GTG GAT CCC ATG GAC GAG    2736
Ser Ala His Ala Leu Asp Met Thr Phe Glu Val Asp Pro Met Asp Glu
        900                 905                 910
```

```
CCC ACC CTT CTT TAT GTT TTG TTT GAA GTC TTT GAC GTG GTC CGT GTG     2784
Pro Thr Leu Leu Tyr Val Leu Phe Glu Val Phe Asp Val Val Arg Val
        915                 920                 925

CAC CGG CCG CAC CGC GGC GTC ATC GAA ACC GTG TAC CTG CGC ACG CCC     2832
His Arg Pro His Arg Gly Val Ile Glu Thr Val Tyr Leu Arg Thr Pro
        930                 935                 940

TTC TCG GCC GGC AAC GCA HHH HHH    HH                               2858
Phe Ser Ala Gly Asn Ala Xaa Xaa
945                 950
```

(2) INFORMATION FOR SEQ ID NO:4:

(i) SEQUENCE CHARACTERISTICS:
        (A) LENGTH: 952 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 951,952
        (D) OTHER INFORMATION: /note= "Xaa can be either Gln, His, or Thr"

(xi) SEQUENCE DESCRIPTION: SEQ ID NO:4:

```
Met Ala Thr Pro Ser Met Met Pro Gln Trp Ser Tyr Met His Ile Ser
 1               5                  10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
        50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ala Leu Ala Pro Lys Gly
            115                 120                 125

Ala Pro Asn Pro Cys Glu Trp Asp Glu Ala Ala Thr Ala Leu Glu Ile
        130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255
```

-continued

```
Lys Leu Glu Ser Gln Val Glu Met Gln Phe Phe Ser Thr Thr Glu Ala
            260                 265                 270
Thr Ala Gly Asn Gly Asp Asn Leu Thr Pro Lys Val Val Leu Tyr Ser
        275                 280                 285
Glu Asp Val Asp Ile Glu Thr Pro Asp Thr His Ile Ser Tyr Met Pro
    290                 295                 300
Thr Ile Lys Glu Gly Asn Ser Arg Glu Leu Met Gly Gln Gln Ser Met
305                 310                 315                 320
Pro Asn Arg Pro Asn Tyr Ile Ala Phe Arg Asp Asn Phe Ile Gly Leu
                325                 330                 335
Met Tyr Tyr Asn Ser Thr Gly Asn Met Gly Val Leu Ala Gly Gln Ala
            340                 345                 350
Ser Gln Leu Asn Ala Val Val Asp Leu Gln Asp Arg Asn Thr Glu Leu
        355                 360                 365
Ser Tyr Gln Leu Leu Leu Asp Ser Ile Gly Asp Arg Thr Arg Tyr Phe
    370                 375                 380
Ser Met Trp Asn Gln Ala Val Asp Ser Tyr Asp Pro Asp Val Arg Ile
385                 390                 395                 400
Ile Glu Asn His Gly Thr Glu Asp Glu Leu Pro Asn Tyr Cys Phe Pro
                405                 410                 415
Leu Gly Gly Val Ile Asn Thr Glu Thr Leu Thr Lys Val Lys Pro Lys
            420                 425                 430
Thr Gly Gln Glu Asn Gly Trp Glu Lys Asp Ala Thr Glu Phe Ser Asp
        435                 440                 445
Lys Asn Glu Ile Arg Val Gly Asn Asn Phe Ala Met Glu Ile Asn Leu
    450                 455                 460
Asn Ala Asn Leu Trp Arg Asn Phe Leu Tyr Ser Asn Ile Ala Leu Tyr
465                 470                 475                 480
Leu Pro Asp Lys Leu Lys Tyr Ser Pro Ser Asn Val Lys Ile Ser Asp
                485                 490                 495
Asn Pro Asn Thr Tyr Asp Tyr Met Asn Lys Arg Val Val Ala Pro Gly
            500                 505                 510
Leu Val Asp Cys Tyr Ile Asn Leu Gly Ala Arg Trp Ser Leu Asp Tyr
        515                 520                 525
Met Asp Asn Val Asn Pro Phe Asn His His Arg Asn Ala Gly Leu Arg
    530                 535                 540
Tyr Arg Ser Met Leu Leu Gly Asn Gly Arg Tyr Val Pro Phe His Ile
545                 550                 555                 560
Gln Val Pro Gln Lys Phe Phe Ala Ile Lys Asn Leu Leu Leu Leu Pro
                565                 570                 575
Gly Ser Tyr Thr Tyr Glu Trp Asn Phe Arg Lys Asp Val Asn Met Val
            580                 585                 590
Leu Gln Ser Ser Leu Gly Asn Asp Leu Arg Val Asp Gly Ala Ser Ile
        595                 600                 605
Lys Phe Asp Ser Ile Cys Leu Tyr Ala Thr Phe Phe Pro Met Ala His
    610                 615                 620
Asn Thr Ala Ser Thr Leu Glu Ala Met Leu Arg Asn Asp Thr Asn Asp
625                 630                 635                 640
Gln Ser Phe Asn Asp Tyr Leu Ser Ala Ala Asn Met Leu Tyr Pro Ile
                645                 650                 655
Pro Ala Asn Ala Thr Asn Val Pro Ile Ser Ile Pro Ser Arg Asn Trp
            660                 665                 670
Ala Ala Phe Arg Gly Trp Ala Phe Thr Arg Leu Lys Thr Lys Glu Thr
```

-continued

```
            675                 680                 685
Pro Ser Leu Gly Ser Gly Tyr Asp Pro Tyr Tyr Thr Tyr Ser Gly Ser
            690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                    725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
                755                 760                 765

Gln Met Leu Ala Asn Tyr Asn Ile Gly Tyr Gln Gly Phe Tyr Ile Pro
770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                    805                 810                 815

Val Gly Ile Leu His Gln His Asn Asn Ser Gly Phe Val Gly Tyr Leu
                820                 825                 830

Ala Pro Thr Met Arg Glu Gly Gln Ala Tyr Pro Ala Asn Phe Pro Tyr
            835                 840                 845

Pro Leu Ile Gly Lys Thr Ala Val Asp Ser Ile Thr Gln Lys Lys Phe
850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                    885                 890                 895

Ser Ala His Ala Leu Asp Met Thr Phe Glu Val Asp Pro Met Asp Glu
                900                 905                 910

Pro Thr Leu Leu Tyr Val Leu Phe Glu Val Phe Asp Val Val Arg Val
            915                 920                 925

His Arg Pro His Arg Gly Val Ile Glu Thr Val Tyr Leu Arg Thr Pro
930                 935                 940

Phe Ser Ala Gly Asn Ala Xaa Xaa
945                 950
```

(2) INFORMATION FOR SEQ ID NO:5:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

```
TCC TGT GAG TGG GAA CAA ACC GAA GAT AGC GGC CGG GCA GTT GCC GAG      48
Ser Cys Glu Trp Glu Gln Thr Glu Asp Ser Gly Arg Ala Val Ala Glu
  1               5                  10                  15

GAT GAA GAA GAG GAA GAT GAA GAT GAA GAA GAG GAA GAA GAA GAG CAA      96
Asp Glu Glu Glu Glu Asp Glu Asp Glu Glu Glu Glu Glu Glu Glu Gln
                 20                  25                  30

AAC GCT CGA GAT CAG GCT ACT AAG AAA ACA CAT GTC TAT GCC CAG GCT     144
Asn Ala Arg Asp Gln Ala Thr Lys Lys Thr His Val Tyr Ala Gln Ala
             35                  40                  45

CCT TTG TCT GGA GAA ACA ATT ACA AAA AGC GGG CTA CAA ATA GGA TCA     192
```

-continued

```
Pro Leu Ser Gly Glu Thr Ile Thr Lys Ser Gly Leu Gln Ile Gly Ser
     50                  55                  60

GAC AAT GCA GAA ACA CAA GCT AAA CCT GTA TAC GCA GAT CCT TCC TAT      240
Asp Asn Ala Glu Thr Gln Ala Lys Pro Val Tyr Ala Asp Pro Ser Tyr
 65                  70                  75                  80

CAA CCA GAA CCT CAA ATT GGC GAA TCT CAG TGG AAC GAA GCT GAT GCT      288
Gln Pro Glu Pro Gln Ile Gly Glu Ser Gln Trp Asn Glu Ala Asp Ala
                 85                  90                  95

AAT GCG GCA GGA GGG AGA GTG CTT AAA AAA ACA ACT CCC ATG AAA CCA      336
Asn Ala Ala Gly Gly Arg Val Leu Lys Lys Thr Thr Pro Met Lys Pro
            100                 105                 110

TGC TAT GGA TCT TAT GCC AGG CCT ACA AAT CCT TTT GGT GGT CAA TCC      384
Cys Tyr Gly Ser Tyr Ala Arg Pro Thr Asn Pro Phe Gly Gly Gln Ser
        115                 120                 125

GTT CTG GTT CCG GAT GAA AAA GGG GTG CCT CTT CCA AAG GTT GAC TTG      432
Val Leu Val Pro Asp Glu Lys Gly Val Pro Leu Pro Lys Val Asp Leu
    130                 135                 140

CAA TTC TTC TCA AAT ACT ACC TCT TTG AAC GAC CGG CAA GGC AAT GCT      480
Gln Phe Phe Ser Asn Thr Thr Ser Leu Asn Asp Arg Gln Gly Asn Ala
145                 150                 155                 160

ACT AAA CCA AAA GTG GTT TTG TAC AGT GAA GAT GTA AAT ATG GAA ACC      528
Thr Lys Pro Lys Val Val Leu Tyr Ser Glu Asp Val Asn Met Glu Thr
                165                 170                 175

CCA GAC ACA CAT CTG TCT TAC AAA CCT GGA AAA GGT GAT GAA AAT TCT      576
Pro Asp Thr His Leu Ser Tyr Lys Pro Gly Lys Gly Asp Glu Asn Ser
            180                 185                 190

AAA GCT ATG TTG GGT CAA CAA TCT ATG                                  603
Lys Ala Met Leu Gly Gln Gln Ser Met
        195                 200
```

(2) INFORMATION FOR SEQ ID NO:6:

(i) SEQUENCE CHARACTERISTICS:
        (A) LENGTH: 201 amino acids
        (B) TYPE: amino acid
        (D) TOPOLOGY: linear (ii) MOLECULE TYPE: peptide (xi) SEQUENCE DESCRIPTION: SEQ ID NO:6:

```
Ser Cys Glu Trp Glu Gln Thr Glu Asp Ser Gly Arg Ala Val Ala Glu
 1               5                  10                  15

Asp Glu Glu Glu Asp Glu Asp Glu Glu Glu Glu Glu Glu Glu Glu Gln
                20                  25                  30

Asn Ala Arg Asp Gln Ala Thr Lys Lys Thr His Val Tyr Ala Gln Ala
            35                  40                  45

Pro Leu Ser Gly Glu Thr Ile Thr Lys Ser Gly Leu Gln Ile Gly Ser
     50                  55                  60

Asp Asn Ala Glu Thr Gln Ala Lys Pro Val Tyr Ala Asp Pro Ser Tyr
 65                  70                  75                  80

Gln Pro Glu Pro Gln Ile Gly Glu Ser Gln Trp Asn Glu Ala Asp Ala
                 85                  90                  95

Asn Ala Ala Gly Gly Arg Val Leu Lys Lys Thr Thr Pro Met Lys Pro
            100                 105                 110

Cys Tyr Gly Ser Tyr Ala Arg Pro Thr Asn Pro Phe Gly Gly Gln Ser
        115                 120                 125

Val Leu Val Pro Asp Glu Lys Gly Val Pro Leu Pro Lys Val Asp Leu
    130                 135                 140

Gln Phe Phe Ser Asn Thr Thr Ser Leu Asn Asp Arg Gln Gly Asn Ala
```

```
145                 150                 155                 160
Thr Lys Pro Lys Val Val Leu Tyr Ser Glu Asp Val Asn Met Glu Thr
                    165                 170                 175

Pro Asp Thr His Leu Ser Tyr Lys Pro Gly Lys Gly Asp Glu Asn Ser
            180                 185                 190

Lys Ala Met Leu Gly Gln Gln Ser Met
        195                 200
```

(2) INFORMATION FOR SEQ ID NO:7:

(i) SEQUENCE CHARACTERISTICS:
        (A) LENGTH: 567 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
CCT TGC GAA TGG GAT GAA GCT GCT ACT GCT CTT GAA ATA AAC CTA GAA         48
Pro Cys Glu Trp Asp Glu Ala Ala Thr Ala Leu Glu Ile Asn Leu Glu
 1               5                  10                  15

GAA GAG GAC GAT GAC AAC GAA GAC GAA GTA GAC GAG CAA GCT GAG CAG         96
Glu Glu Asp Asp Asp Asn Glu Asp Glu Val Asp Glu Gln Ala Glu Gln
                20                  25                  30

CAA AAA ACT CAC GTA TTT GGG CAG GCG CCT TAT TCT GGT ATA AAT ATT        144
Gln Lys Thr His Val Phe Gly Gln Ala Pro Tyr Ser Gly Ile Asn Ile
            35                  40                  45

ACA AAG GAG GGT ATT CAA ATA GGT GTC GAA GGT CAA ACA CCT AAA TAT        192
Thr Lys Glu Gly Ile Gln Ile Gly Val Glu Gly Gln Thr Pro Lys Tyr
        50                  55                  60

GCC GAT AAA ACA TTT CAA CCT GAA CCT CAA ATA GGA GAA TCT CAG TGG        240
Ala Asp Lys Thr Phe Gln Pro Glu Pro Gln Ile Gly Glu Ser Gln Trp
 65                  70                  75                  80

TAC GAA ACT GAA ATT AAT CAT GCA GCT GGG AGA GTC CTT AAA AAG ACT        288
Tyr Glu Thr Glu Ile Asn His Ala Ala Gly Arg Val Leu Lys Lys Thr
                 85                  90                  95

ACC CCA ATG AAA CCA TGT TAC GGT TCA TAT GCA AAA CCC ACA AAT GAA        336
Thr Pro Met Lys Pro Cys Tyr Gly Ser Tyr Ala Lys Pro Thr Asn Glu
            100                 105                 110

AAT GGA GGG CAA GGC ATT CTT GTA AAG CAA CAA AAT GGA AAG CTA GAA        384
Asn Gly Gly Gln Gly Ile Leu Val Lys Gln Gln Asn Gly Lys Leu Glu
        115                 120                 125

AGT CAA GTG GAA ATG CAA TTT TTC TCA ACT ACT GAG GCG ACC GCA GGC        432
Ser Gln Val Glu Met Gln Phe Phe Ser Thr Thr Glu Ala Thr Ala Gly
130                 135                 140

AAT GGT GAT AAC TTG ACT CCT AAA GTG GTA TTG TAC AGT GAA GAT GTA        480
Asn Gly Asp Asn Leu Thr Pro Lys Val Val Leu Tyr Ser Glu Asp Val
145                 150                 155                 160

GAT ATA GAA ACC CCA GAC ACT CAT ATT TCT TAC ATG CCC ACT ATT AAG        528
Asp Ile Glu Thr Pro Asp Thr His Ile Ser Tyr Met Pro Thr Ile Lys
                165                 170                 175

GAA GGT AAC TCA CGA GAA CTA ATG GGC CAA CAA TCT ATG                    567
Glu Gly Asn Ser Arg Glu Leu Met Gly Gln Gln Ser Met
            180                 185
```

(2) INFORMATION FOR SEQ ID NO:8:

(i) SEQUENCE CHARACTERISTICS:
        (A) LENGTH: 189 amino acids
        (B) TYPE: amino acid
        (D) TOPOLOGY: linear (ii) MOLECULE TYPE: peptide (xi) SEQUENCE DESCRIPTION: SEQ ID NO:8:

```
Pro Cys Glu Trp Asp Glu Ala Ala Thr Ala Leu Glu Ile Asn Leu Glu
 1               5                  10                  15

Glu Glu Asp Asp Asp Asn Glu Asp Val Asp Glu Gln Ala Glu Gln
             20                  25                  30

Gln Lys Thr His Val Phe Gly Gln Ala Pro Tyr Ser Gly Ile Asn Ile
         35                  40                  45

Thr Lys Glu Gly Ile Gln Ile Gly Val Glu Gly Gln Thr Pro Lys Tyr
 50                  55                  60

Ala Asp Lys Thr Phe Gln Pro Glu Pro Gln Ile Gly Glu Ser Gln Trp
 65                  70                  75                  80

Tyr Glu Thr Glu Ile Asn His Ala Ala Gly Arg Val Leu Lys Lys Thr
                 85                  90                  95

Thr Pro Met Lys Pro Cys Tyr Gly Ser Tyr Ala Lys Pro Thr Asn Glu
             100                 105                 110

Asn Gly Gly Gln Gly Ile Leu Val Lys Gln Gln Asn Gly Lys Leu Glu
             115                 120                 125

Ser Gln Val Glu Met Gln Phe Phe Ser Thr Thr Glu Ala Thr Ala Gly
 130                 135                 140

Asn Gly Asp Asn Leu Thr Pro Lys Val Val Leu Tyr Ser Glu Asp Val
 145                 150                 155                 160

Asp Ile Glu Thr Pro Asp Thr His Ile Ser Tyr Met Pro Thr Ile Lys
                 165                 170                 175

Glu Gly Asn Ser Arg Glu Leu Met Gly Gln Gln Ser Met
             180                 185
```

(2) INFORMATION FOR SEQ ID NO:9:

(i) SEQUENCE CHARACTERISTICS:
            (A) LENGTH: 153 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:9:

```
ACC GAA GAT AGC GGC CGG GCA GTT GCC GAG GAT GAA GAA GAG GAA GAT    48
Thr Glu Asp Ser Gly Arg Ala Val Ala Glu Asp Glu Glu Glu Glu Asp
 1               5                  10                  15

GAA GAT GAA GAA GAG GAA GAA GAA GAG CAA AAC GCT CGA GAT CAG GCT    96
Glu Asp Glu Glu Glu Glu Glu Glu Glu Gln Asn Ala Arg Asp Gln Ala
             20                  25                  30

ACT AAG AAA ACA CAT GTC TAT GCC CAG GCT CCT TTG TCT GGA GAA ACA   144
Thr Lys Lys Thr His Val Tyr Ala Gln Ala Pro Leu Ser Gly Glu Thr
         35                  40                  45

ATT ACA AAA                                                       153
Ile Thr Lys
         50
```

(2) INFORMATION FOR SEQ ID NO:10:

(i) SEQUENCE CHARACTERISTICS:
            (A) LENGTH: 51 amino acids
            (B) TYPE: amino acid
            (D) TOPOLOGY: linear (ii) MOLECULE TYPE: peptide (xi) SEQUENCE DESCRIPTION: SEQ ID NO:10:

Thr Glu Asp Ser Gly Arg Ala Val Ala Glu Asp Glu Glu Glu Asp
  1               5                  10                  15

Glu Asp Glu Glu Glu Glu Glu Glu Gln Asn Ala Arg Asp Gln Ala
                 20                  25                  30

Thr Lys Lys Thr His Val Tyr Ala Gln Ala Pro Leu Ser Gly Glu Thr
             35                  40                  45

Ile Thr Lys
         50

(2) INFORMATION FOR SEQ ID NO:11:

(i) SEQUENCE CHARACTERISTICS:
            (A) LENGTH: 135 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:11:

GCT GCT ACT GCT CTT GAA ATA AAC CTA GAA GAA GAG GAC GAT GAC AAC          48
Ala Ala Thr Ala Leu Glu Ile Asn Leu Glu Glu Glu Asp Asp Asp Asn
  1               5                  10                  15

GAA GAC GAA GTA GAC GAG CAA GCT GAG CAG CAA AAA ACT CAC GTA TTT          96
Glu Asp Glu Val Asp Glu Gln Ala Glu Gln Gln Lys Thr His Val Phe
                 20                  25                  30

GGG CAG GCG CCT TAT TCT GGT ATA AAT ATT ACA AAG GAG                     135
Gly Gln Ala Pro Tyr Ser Gly Ile Asn Ile Thr Lys Glu
             35                  40                  45

(2) INFORMATION FOR SEQ ID NO:12:

(i) SEQUENCE CHARACTERISTICS:
            (A) LENGTH: 45 amino acids
            (B) TYPE: amino acid
            (D) TOPOLOGY: linear (ii) MOLECULE TYPE: peptide (xi) SEQUENCE DESCRIPTION: SEQ ID NO:12:

Ala Ala Thr Ala Leu Glu Ile Asn Leu Glu Glu Glu Asp Asp Asp Asn
  1               5                  10                  15

Glu Asp Glu Val Asp Glu Gln Ala Glu Gln Gln Lys Thr His Val Phe
                 20                  25                  30

Gly Gln Ala Pro Tyr Ser Gly Ile Asn Ile Thr Lys Glu
             35                  40                  45

(2) INFORMATION FOR SEQ ID NO:13:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

TCA GAC AAT GCA GAA ACA CAA GCT AAA CCT GTA                              33
Ser Asp Asn Ala Glu Thr Gln Ala Lys Pro Val
  1               5                  10

(2) INFORMATION FOR SEQ ID NO:14:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:14:

```
Ser Asp Asn Ala Glu Thr Gln Ala Lys Pro Val
 1               5                  10
```

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

```
GTC GAA GGT CAA ACA CCT AAA                                      21
Val Glu Gly Gln Thr Pro Lys
 1               5
```

(2) INFORMATION FOR SEQ ID NO:16:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:16:

```
Val Glu Gly Gln Thr Pro Lys
 1               5
```

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

```
AAC GAA GCT GAT GCT AAT GCG GCA                                  24
Asn Glu Ala Asp Ala Asn Ala Ala
 1               5
```

(2) INFORMATION FOR SEQ ID NO:18:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:18:

```
Asn Glu Ala Asp Ala Asn Ala Ala
 1               5
```

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

```
TAC GAA ACT GAA ATT AAT CAT GCA                                24
Tyr Glu Thr Glu Ile Asn His Ala
 1               5
```

(2) INFORMATION FOR SEQ ID NO:20:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:20:

```
Tyr Glu Thr Glu Ile Asn His Ala
 1               5
```

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:21:

```
TCC GTT CTG GTT CCG GAT GAA AAA GGG GTG CCT CTT CCA AAG         42
Ser Val Leu Val Pro Asp Glu Lys Gly Val Pro Leu Pro Lys
 1               5                  10
```

(2) INFORMATION FOR SEQ ID NO:22:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:22:

```
Ser Val Leu Val Pro Asp Glu Lys Gly Val Pro Leu Pro Lys
 1               5                  10
```

(2) INFORMATION FOR SEQ ID NO:23:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGC ATT CTT GTA AAG CAA CAA AAT GGA AAG CTA GAA AGT CAA         42
Gly Ile Leu Val Lys Gln Gln Asn Gly Lys Leu Glu Ser Gln
  1               5                  10
```

(2) INFORMATION FOR SEQ ID NO:24:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:24:

```
Gly Ile Leu Val Lys Gln Gln Asn Gly Lys Leu Glu Ser Gln
  1               5                  10
```

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

```
TCA AAT ACT ACC TCT TTG AAC GAC CGG CAA GGC AAT GCT ACT AAA CCA         48
Ser Asn Thr Thr Ser Leu Asn Asp Arg Gln Gly Asn Ala Thr Lys Pro
  1               5                  10                  15

AAA                                                                      51
Lys
```

(2) INFORMATION FOR SEQ ID NO:26:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:26:

```
Ser Asn Thr Thr Ser Leu Asn Asp Arg Gln Gly Asn Ala Thr Lys Pro
  1               5                  10                  15

Lys
```

(2) INFORMATION FOR SEQ ID NO:27:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:27:

```
TCA ACT ACT GAG GCG ACC GCA GGC AAT GGT GAT AAC TTG ACT CCT AAA         48
Ser Thr Thr Glu Ala Thr Ala Gly Asn Gly Asp Asn Leu Thr Pro Lys
  1               5                  10                  15
```

(2) INFORMATION FOR SEQ ID NO:28:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:28:

```
Ser Thr Thr Glu Ala Thr Ala Gly Asn Gly Asp Asn Leu Thr Pro Lys
 1               5                  10                  15
```

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:29:

```
TTG TAC AGT GAA GAT GTA AAT ATG                                    24
Leu Tyr Ser Glu Asp Val Asn Met
 1               5
```

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:30:

```
Leu Tyr Ser Glu Asp Val Asn Met
 1               5
```

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:31:

```
TTG TAC AGT GAA GAT GTA GAT ATA                                    24
Leu Tyr Ser Glu Asp Val Asp Ile
 1               5
```

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:32:

```
Leu Tyr Ser Glu Asp Val Asp Ile
 1               5
```

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:33:

```
GGA AAA GGT GAT GAA AAT TCT AAA GCT ATG TTG GGT             36
Gly Lys Gly Asp Glu Asn Ser Lys Ala Met Leu Gly
 1               5                  10
```

(2) INFORMATION FOR SEQ ID NO:34:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:34:

```
Gly Lys Gly Asp Glu Asn Ser Lys Ala Met Leu Gly
 1               5                  10
```

(2) INFORMATION FOR SEQ ID NO:35:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:35:

```
ACT ATT AAG GAA GGT AAC TCA CGA GAA CTA ATG GGC             36
Thr Ile Lys Glu Gly Asn Ser Arg Glu Leu Met Gly
 1               5                  10
```

(2) INFORMATION FOR SEQ ID NO:36:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:36:

```
Thr Ile Lys Glu Gly Asn Ser Arg Glu Leu Met Gly
 1               5                  10
```

(2) INFORMATION FOR SEQ ID NO:37:

(i) SEQUENCE CHARACTERISTICS:
        (A) LENGTH: 165 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:37:

```
AAT TAT TGT TTT CCT CTT GGG GGT ATT GGG GTA ACT GAC ACC TAT CAA     48
Asn Tyr Cys Phe Pro Leu Gly Gly Ile Gly Val Thr Asp Thr Tyr Gln
 1               5                  10                  15
```

```
GCT ATT AAG GCT AAT GGC AAT GGC TCA GGC GAT AAT GGA GAT ACT ACA      96
Ala Ile Lys Ala Asn Gly Asn Gly Ser Gly Asp Asn Gly Asp Thr Thr
             20                  25                  30

TGG ACA AAA GAT GAA ACT TTT GCA ACA CGT AAT GAA ATA GGA GTG GGT     144
Trp Thr Lys Asp Glu Thr Phe Ala Thr Arg Asn Glu Ile Gly Val Gly
         35                  40                  45

AAC AAC TTT GCC ATG GAA ATT                                         165
Asn Asn Phe Ala Met Glu Ile
 50                  55
```

(2) INFORMATION FOR SEQ ID NO:38:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (xi) SEQUENCE DESCRIPTION: SEQ ID NO:38:

```
Asn Tyr Cys Phe Pro Leu Gly Gly Ile Gly Val Thr Asp Thr Tyr Gln
 1               5                  10                  15

Ala Ile Lys Ala Asn Gly Asn Gly Ser Gly Asp Asn Gly Asp Thr Thr
             20                  25                  30

Trp Thr Lys Asp Glu Thr Phe Ala Thr Arg Asn Glu Ile Gly Val Gly
         35                  40                  45

Asn Asn Phe Ala Met Glu Ile
 50                  55
```

(2) INFORMATION FOR SEQ ID NO:39:

(i) SEQUENCE CHARACTERISTICS:
        (A) LENGTH: 153 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:39:

```
AAT TAC TGC TTT CCA CTG GGA GGT GTG ATT AAT ACA GAG ACT CTT ACC      48
Asn Tyr Cys Phe Pro Leu Gly Gly Val Ile Asn Thr Glu Thr Leu Thr
 1               5                  10                  15

AAG GTA AAA CCT AAA ACA GGT CAG GAA AAT GGA TGG GAA AAA GAT GCT      96
Lys Val Lys Pro Lys Thr Gly Gln Glu Asn Gly Trp Glu Lys Asp Ala
             20                  25                  30

ACA GAA TTT TCA GAT AAA AAT GAA ATA AGA GTT GGA AAT AAT TTT GCC     144
Thr Glu Phe Ser Asp Lys Asn Glu Ile Arg Val Gly Asn Asn Phe Ala
         35                  40                  45

ATG GAA ATC                                                         153
Met Glu Ile
     50
```

(2) INFORMATION FOR SEQ ID NO:40:

(i) SEQUENCE CHARACTERISTICS:
        (A) LENGTH: 51 amino acids
        (B) TYPE: amino acid
        (D) TOPOLOGY: linear (ii) MOLECULE TYPE: peptide (xi) SEQUENCE DESCRIPTION: SEQ ID NO:40:

```
Asn Tyr Cys Phe Pro Leu Gly Gly Val Ile Asn Thr Glu Thr Leu Thr
 1               5                  10                 15

Lys Val Lys Pro Lys Thr Gly Gln Glu Asn Gly Trp Glu Lys Asp Ala
                20                  25                 30

Thr Glu Phe Ser Asp Lys Asn Glu Ile Arg Val Gly Asn Asn Phe Ala
            35                  40                  45

Met Glu Ile
    50
```

(2) INFORMATION FOR SEQ ID NO:41:

(i) SEQUENCE CHARACTERISTICS:
        (A) LENGTH: 54 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

```
GTA ACT GAC ACC TAT CAA GCT ATT AAG GCT AAT GGC AAT GGC TCA GGC    48
Val Thr Asp Thr Tyr Gln Ala Ile Lys Ala Asn Gly Asn Gly Ser Gly
 1               5                  10                 15

GAT AAT                                                           54
Asp Asn
```

(2) INFORMATION FOR SEQ ID NO:42:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:42:

```
Val Thr Asp Thr Tyr Gln Ala Ile Lys Ala Asn Gly Asn Gly Ser Gly
 1               5                  10                 15

Asp Asn
```

(2) INFORMATION FOR SEQ ID NO:43:

(i) SEQUENCE CHARACTERISTICS:
        (A) LENGTH: 87 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:43:

```
AAT ACA GAG ACT CTT ACC AAG GTA AAA CCT AAA ACA GGT CAG GAA AAT    48
Asn Thr Glu Thr Leu Thr Lys Val Lys Pro Lys Thr Gly Gln Glu Asn
 1               5                  10                 15

GGA TGG GAA AAA GAT GCT ACA GAA TTT TCA GAT AAA AAT                87
Gly Trp Glu Lys Asp Ala Thr Glu Phe Ser Asp Lys Asn
                20                  25
```

(2) INFORMATION FOR SEQ ID NO:44:

(i) SEQUENCE CHARACTERISTICS:
        (A) LENGTH: 29 amino acids
        (B) TYPE: amino acid
        (D) TOPOLOGY: linear

```
        (ii) MOLECULE TYPE: peptide (xi) SEQUENCE DESCRIPTION: SEQ ID NO:44:

Asn Thr Glu Thr Leu Thr Lys Val Lys Pro Lys Thr Gly Gln Glu Asn
 1               5                  10                  15

Gly Trp Glu Lys Asp Ala Thr Glu Phe Ser Asp Lys Asn
            20                  25

(2) INFORMATION FOR SEQ ID NO:45:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:45:

ACT TTT GCA ACA CGT AAT GAA                                    21
Thr Phe Ala Thr Arg Asn Glu
 1               5

(2) INFORMATION FOR SEQ ID NO:46:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:46:

Thr Phe Ala Thr Arg Asn Glu
 1               5

(2) INFORMATION FOR SEQ ID NO:47:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:47:

ACA GAA TTT TCA GAT AAA AAT GAA                                24
Thr Glu Phe Ser Asp Lys Asn Glu
 1               5

(2) INFORMATION FOR SEQ ID NO:48:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:48:

Thr Glu Phe Ser Asp Lys Asn Glu
 1               5

(2) INFORMATION FOR SEQ ID NO:49:

(i) SEQUENCE CHARACTERISTICS:
            (A) LENGTH: 24 base pairs
```

```
            (B) TYPE: nucleic acid
            (C) STRANDEDNESS: double
            (D) TOPOLOGY: linear (ii) MOLECULE TYPE: other nucleic acid (xi) SEQUENCE DESCRIPTION: SEQ ID NO:49:

GAC TAC AAA GAC GAC GAC GAC AAA                                      24
Asp Tyr Lys Asp Asp Asp Asp Lys
  1               5

(2) INFORMATION FOR SEQ ID NO:50:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (xi) SEQUENCE DESCRIPTION: SEQ ID NO:50:

Asp Tyr Lys Asp Asp Asp Asp Lys
  1               5

(2) INFORMATION FOR SEQ ID NO:51:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:51:

CACACACCCG TAACGCTGGA C                                              21

(2) INFORMATION FOR SEQ ID NO:52:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:52:

GGGGGGATCG ATGGCGCGCG GCGGCCAGCA GCT                                 33

(2) INFORMATION FOR SEQ ID NO:53:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO:53:

CGATCCAAGA TGGCCACCCC AT                                             22

(2) INFORMATION FOR SEQ ID NO:54:

(i) SEQUENCE CHARACTERISTICS:
            (A) LENGTH: 22 base pairs
            (B) TYPE: nucleic acid
```

```
            (C) STRANDEDNESS: single
            (D) TOPOLOGY: linear (ii) MOLECULE TYPE: other nucleic acid (xi) SEQUENCE DESCRIPTION: SEQ ID NO:54:

CGATGGGGTG GCCATCTTGG AT                                                   22

(2) INFORMATION FOR SEQ ID NO:55:

(i) SEQUENCE CHARACTERISTICS:
            (A) LENGTH: 2907 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:55:
```

| | | | | | | | | | | | | | | | | |
|---|---|---|---|---|---|---|---|---|---|---|---|---|---|---|---|---|
| ATG | GCT | ACC | CCT | TCG | ATG | ATG | CCG | CAG | TGG | TCT | TAC | ATG | CAC | ATC | TCG | 48 |
| Met | Ala | Thr | Pro | Ser | Met | Met | Pro | Gln | Trp | Ser | Tyr | Met | His | Ile | Ser | |
| 1 | | | | 5 | | | | | 10 | | | | | | 15 | |
| GGC | CAG | GAC | GCC | TCG | GAG | TAC | CTG | AGC | CCC | GGG | CTG | GTG | CAG | TTT | GCC | 96 |
| Gly | Gln | Asp | Ala | Ser | Glu | Tyr | Leu | Ser | Pro | Gly | Leu | Val | Gln | Phe | Ala | |
| | | | 20 | | | | | 25 | | | | | 30 | | | |
| CGC | GCC | ACC | GAG | ACG | TAC | TTC | AGC | CTG | AAT | AAC | AAG | TTT | AGA | AAC | CCC | 144 |
| Arg | Ala | Thr | Glu | Thr | Tyr | Phe | Ser | Leu | Asn | Asn | Lys | Phe | Arg | Asn | Pro | |
| | | 35 | | | | | 40 | | | | | 45 | | | | |
| ACG | GTG | GCA | CCT | ACG | CAC | GAC | GTA | ACC | ACA | GAC | CGG | TCC | CAG | CGT | TTG | 192 |
| Thr | Val | Ala | Pro | Thr | His | Asp | Val | Thr | Thr | Asp | Arg | Ser | Gln | Arg | Leu | |
| | 50 | | | | | 55 | | | | | 60 | | | | | |
| ACG | CTG | CGG | TTC | ATC | CCT | GTG | GAC | CGC | GAG | GAT | ACC | GCG | TAC | TCG | TAC | 240 |
| Thr | Leu | Arg | Phe | Ile | Pro | Val | Asp | Arg | Glu | Asp | Thr | Ala | Tyr | Ser | Tyr | |
| 65 | | | | | 70 | | | | | 75 | | | | | | |
| AAA | GCG | CGG | TTC | ACC | CTG | GCT | GTG | GGT | GAC | AAC | CGT | GTG | CTT | GAT | ATG | 288 |
| Lys | Ala | Arg | Phe | Thr | Leu | Ala | Val | Gly | Asp | Asn | Arg | Val | Leu | Asp | Met | |
| 80 | | | | | 85 | | | | | 90 | | | | | 95 | |
| GCT | TCC | ACG | TAC | TTT | GAC | ATC | CGC | GGC | GTG | CTG | GAC | AGG | GGG | CCT | ACT | 336 |
| Ala | Ser | Thr | Tyr | Phe | Asp | Ile | Arg | Gly | Val | Leu | Asp | Arg | Gly | Pro | Thr | |
| | | | | 100 | | | | | 105 | | | | | 110 | | |
| TTT | AAG | CCC | TAC | TCC | GGC | ACT | GCC | TAC | AAC | GCT | CTA | GCT | CCC | AAG | GGC | 384 |
| Phe | Lys | Pro | Tyr | Ser | Gly | Thr | Ala | Tyr | Asn | Ala | Leu | Ala | Pro | Lys | Gly | |
| | | | 115 | | | | | 120 | | | | | 125 | | | |
| GCT | CCT | AAC | TCC | TGT | GAG | TGG | GAA | CAA | ACC | GAA | GAT | AGC | GGC | CGG | GCA | 432 |
| Ala | Pro | Asn | Ser | Cys | Glu | Trp | Glu | Gln | Thr | Glu | Asp | Ser | Gly | Arg | Ala | |
| | | 130 | | | | | 135 | | | | | 140 | | | | |
| GTT | GCC | GAG | GAT | GAA | GAA | GAG | GAA | GAT | GAA | GAT | GAA | GAA | GAG | GAA | GAA | 480 |
| Val | Ala | Glu | Asp | Glu | Glu | Glu | Glu | Asp | Glu | Asp | Glu | Glu | Glu | Glu | Glu | |
| | 145 | | | | | 150 | | | | | 155 | | | | | |
| GAA | GAG | CAA | AAC | GCT | CGA | GAT | CAG | GCT | ACT | AAG | AAA | ACA | CAT | GTC | TAT | 528 |
| Glu | Glu | Gln | Asn | Ala | Arg | Asp | Gln | Ala | Thr | Lys | Lys | Thr | His | Val | Tyr | |
| 160 | | | | | 165 | | | | | 170 | | | | | 175 | |
| GCC | CAG | GCT | CCT | TTG | TCT | GGA | GAA | ACA | ATT | ACA | AAA | AGC | GGG | CTA | CAA | 576 |
| Ala | Gln | Ala | Pro | Leu | Ser | Gly | Glu | Thr | Ile | Thr | Lys | Ser | Gly | Leu | Gln | |
| | | | | 180 | | | | | 185 | | | | | 190 | | |
| ATA | GGA | TCA | GAC | AAT | GCA | GAA | ACA | CAA | GCT | AAA | CCT | GTA | TAC | GCA | GAT | 624 |
| Ile | Gly | Ser | Asp | Asn | Ala | Glu | Thr | Gln | Ala | Lys | Pro | Val | Tyr | Ala | Asp | |
| | | | 195 | | | | | 200 | | | | | 205 | | | |
| CCT | TCC | TAT | CAA | CCA | GAA | CCT | CAA | ATT | GGC | GAA | TCT | CAG | TGG | AAC | GAA | 672 |
| Pro | Ser | Tyr | Gln | Pro | Glu | Pro | Gln | Ile | Gly | Glu | Ser | Gln | Trp | Asn | Glu | |
| | | 210 | | | | | 215 | | | | | 220 | | | | |

-continued

| | |
|---|---|
| GCT GAT GCT AAT GCG GCA GGA GGG AGA GTG CTT AAA AAA ACA ACT CCC<br>Ala Asp Ala Asn Ala Ala Gly Gly Arg Val Leu Lys Lys Thr Thr Pro<br>225                         230                       235 | 720 |
| ATG AAA CCA TGC TAT GGA TCT TAT GCC AGG CCT ACA AAT CCT TTT GGT<br>Met Lys Pro Cys Tyr Gly Ser Tyr Ala Arg Pro Thr Asn Pro Phe Gly<br>240                       245                   250                   255 | 768 |
| GGT CAA TCC GTT CTG GTT CCG GAT GAA AAA GGG GTG CCT CTT CCA AAG<br>Gly Gln Ser Val Leu Val Pro Asp Glu Lys Gly Val Pro Leu Pro Lys<br>                 260                   265                   270 | 816 |
| GTT GAC TTG CAA TTC TTC TCA AAT ACT ACC TCT TTG AAC GAC CGG CAA<br>Val Asp Leu Gln Phe Phe Ser Asn Thr Thr Ser Leu Asn Asp Arg Gln<br>          275                   280                   285 | 864 |
| GGC AAT GCT ACT AAA CCA AAA GTG GTT TTG TAC AGT GAA GAT GTA AAT<br>Gly Asn Ala Thr Lys Pro Lys Val Val Leu Tyr Ser Glu Asp Val Asn<br>          290                   295                   300 | 912 |
| ATG GAA ACC CCA GAC ACA CAT CTG TCT TAC AAA CCT GGA AAA GGT GAT<br>Met Glu Thr Pro Asp Thr His Leu Ser Tyr Lys Pro Gly Lys Gly Asp<br>305                       310                   315 | 960 |
| GAA AAT TCT AAA GCT ATG TTG GGT CAA CAA TCT ATG CCA AAC AGA CCC<br>Glu Asn Ser Lys Ala Met Leu Gly Gln Gln Ser Met Pro Asn Arg Pro<br>320                       325                   330                   335 | 1008 |
| AAT TAC ATT GCT TTC AGG GAC AAT TTT ATT GGC CTA ATG TAT TAT AAC<br>Asn Tyr Ile Ala Phe Arg Asp Asn Phe Ile Gly Leu Met Tyr Tyr Asn<br>                 340                   345                   350 | 1056 |
| AGC ACT GGC AAC ATG GGT GTT CTT GCT GGT CAG GCA TCG CAG CTA AAT<br>Ser Thr Gly Asn Met Gly Val Leu Ala Gly Gln Ala Ser Gln Leu Asn<br>          355                   360                   365 | 1104 |
| GCC GTG GTA GAT TTG CAA GAC AGA AAC ACA GAG CTG TCC TAT CAA CTC<br>Ala Val Val Asp Leu Gln Asp Arg Asn Thr Glu Leu Ser Tyr Gln Leu<br>          370                   375                   380 | 1152 |
| TTG CTT GAT TCC ATA GGT GAT AGA ACC AGA TAT TTT TCT ATG TGG AAT<br>Leu Leu Asp Ser Ile Gly Asp Arg Thr Arg Tyr Phe Ser Met Trp Asn<br>385                       390                   395 | 1200 |
| CAG GCT GTA GAC AGC TAT GAT CCA GAT GTT AGA ATC ATT GAA AAC CAT<br>Gln Ala Val Asp Ser Tyr Asp Pro Asp Val Arg Ile Ile Glu Asn His<br>400                       405                   410                   415 | 1248 |
| GGA ACT GAG GAT GAA TTG CCA AAT TAT TGT TTT CCT CTT GGG GGT ATT<br>Gly Thr Glu Asp Glu Leu Pro Asn Tyr Cys Phe Pro Leu Gly Gly Ile<br>                 420                   425                   430 | 1296 |
| GGG GTA ACT GAC ACC TAT CAA GCT ATT AAG GCT AAT GGC AAT GGC TCA<br>Gly Val Thr Asp Thr Tyr Gln Ala Ile Lys Ala Asn Gly Asn Gly Ser<br>          435                   440                   445 | 1344 |
| GGC GAT AAT GGA GAT ACT ACA TGG ACA AAA GAT GAA ACT TTT GCA ACA<br>Gly Asp Asn Gly Asp Thr Thr Trp Thr Lys Asp Glu Thr Phe Ala Thr<br>450                       455                   460 | 1392 |
| CGT AAT GAA ATA GGA GTG GGT AAC AAC TTT GCC ATG GAA ATT AAC CTA<br>Arg Asn Glu Ile Gly Val Gly Asn Asn Phe Ala Met Glu Ile Asn Leu<br>          465                   470                   475 | 1440 |
| AAT GCC AAC CTA TGG AGA AAT TTC CTT TAC TCC AAT ATT GCG CTG TAC<br>Asn Ala Asn Leu Trp Arg Asn Phe Leu Tyr Ser Asn Ile Ala Leu Tyr<br>480                       485                   490                   495 | 1488 |
| CTG CCA GAC AAG CTA AAA TAC AAC CCC ACC AAT GTG GAA ATA TCT GAC<br>Leu Pro Asp Lys Leu Lys Tyr Asn Pro Thr Asn Val Glu Ile Ser Asp<br>                 500                   505                   510 | 1536 |
| AAC CCC AAC ACC TAC GAC TAC ATG AAC AAG CGA GTG GTG GCT CCC GGG<br>Asn Pro Asn Thr Tyr Asp Tyr Met Asn Lys Arg Val Val Ala Pro Gly<br>          515                   520                   525 | 1584 |
| CTT GTA GAC TGC TAC ATT AAC CTT GGG GCG CGC TGG TCT CTG GAC TAC<br>Leu Val Asp Cys Tyr Ile Asn Leu Gly Ala Arg Trp Ser Leu Asp Tyr<br>          530                   535                   540 | 1632 |

```
ATG GAC AAC GTT AAT CCC TTT AAC CAC CAC CGC AAT GCG GGC CTC CGT      1680
Met Asp Asn Val Asn Pro Phe Asn His His Arg Asn Ala Gly Leu Arg
    545                 550                 555

TAT CGC TCC ATG TTG TTG GGA AAC GGC CGC TAC GTG CCC TTT CAC ATT      1728
Tyr Arg Ser Met Leu Leu Gly Asn Gly Arg Tyr Val Pro Phe His Ile
560                 565                 570                 575

CAG GTG CCC CAA AAG TTT TTT GCC ATT AAA AAC CTC CTC CTC CTG CCA      1776
Gln Val Pro Gln Lys Phe Phe Ala Ile Lys Asn Leu Leu Leu Leu Pro
                580                 585                 590

GGC TCA TAT ACA TAT GAA TGG AAC TTC AGG AAG GAT GTT AAC ATG GTT      1824
Gly Ser Tyr Thr Tyr Glu Trp Asn Phe Arg Lys Asp Val Asn Met Val
            595                 600                 605

CTG CAG AGC TCT CTG GGA AAC GAT CTT AGA GTT GAC GGG GCT AGC ATT      1872
Leu Gln Ser Ser Leu Gly Asn Asp Leu Arg Val Asp Gly Ala Ser Ile
        610                 615                 620

AAG TTT GAC AGC ATT TGT CTT TAC GCC ACC TTC TTC CCC ATG GCC CAC      1920
Lys Phe Asp Ser Ile Cys Leu Tyr Ala Thr Phe Phe Pro Met Ala His
    625                 630                 635

AAC ACG GCC TCC ACG CTG GAA GCC ATG CTC AGA AAT GAC ACC AAC GAC      1968
Asn Thr Ala Ser Thr Leu Glu Ala Met Leu Arg Asn Asp Thr Asn Asp
640                 645                 650                 655

CAG TCC TTT AAT GAC TAC CTT TCC GCC GCC AAC ATG CTA TAC CCC ATA      2016
Gln Ser Phe Asn Asp Tyr Leu Ser Ala Ala Asn Met Leu Tyr Pro Ile
                660                 665                 670

CCC GCC AAC GCC ACC AAC GTG CCC ATC TCC ATC CCA TCG CGC AAC TGG      2064
Pro Ala Asn Ala Thr Asn Val Pro Ile Ser Ile Pro Ser Arg Asn Trp
            675                 680                 685

GCA GCA TTT CGC GGT TGG GCC TTC ACA CGC TTG AAG ACA AAG GAA ACC      2112
Ala Ala Phe Arg Gly Trp Ala Phe Thr Arg Leu Lys Thr Lys Glu Thr
        690                 695                 700

CCT TCC CTG GGA TCA GGC TAC GAC CCT TAC TAC ACC TAC TCT GGC TCC      2160
Pro Ser Leu Gly Ser Gly Tyr Asp Pro Tyr Tyr Thr Tyr Ser Gly Ser
    705                 710                 715

ATA CCA TAC CTT GAC GGA ACC TTC TAT CTT AAT CAC ACC TTT AAG AAG      2208
Ile Pro Tyr Leu Asp Gly Thr Phe Tyr Leu Asn His Thr Phe Lys Lys
720                 725                 730                 735

GTG GCC ATT ACC TTT GAC TCT TCT GTT AGC TGG CCG GGC AAC GAC CGC      2256
Val Ala Ile Thr Phe Asp Ser Ser Val Ser Trp Pro Gly Asn Asp Arg
                740                 745                 750

CTG CTT ACT CCC AAT GAG TTT GAG ATT AAA CGC TCA GTT GAC GGG GAG      2304
Leu Leu Thr Pro Asn Glu Phe Glu Ile Lys Arg Ser Val Asp Gly Glu
            755                 760                 765

GGC TAC AAC GTA GCT CAG TGC AAC ATG ACC AAG GAC TGG TTC CTG GTG      2352
Gly Tyr Asn Val Ala Gln Cys Asn Met Thr Lys Asp Trp Phe Leu Val
        770                 775                 780

CAG ATG TTG GCC AAC TAC AAT ATT GGC TAC CAG GGC TTC TAC ATT CCA      2400
Gln Met Leu Ala Asn Tyr Asn Ile Gly Tyr Gln Gly Phe Tyr Ile Pro
    785                 790                 795

GAA AGC TAC AAG GAC CGC ATG TAC TCG TTC TTC AGA AAC TTC CAG CCC      2448
Glu Ser Tyr Lys Asp Arg Met Tyr Ser Phe Phe Arg Asn Phe Gln Pro
800                 805                 810                 815

ATG AGC CGG CAA GTG GTT GAC GAT ACT AAA TAC AAG GAG TAT CAG CAG      2496
Met Ser Arg Gln Val Val Asp Asp Thr Lys Tyr Lys Glu Tyr Gln Gln
                820                 825                 830

GTT GGA ATT CTT CAC CAG CAT AAC AAC TCA GGA TTC GTA GGC TAC CTC      2544
Val Gly Ile Leu His Gln His Asn Asn Ser Gly Phe Val Gly Tyr Leu
            835                 840                 845
```

```
GCT CCC ACC ATG CGC GAG GGA CAG GCT TAC CCC GCC AAC GTG CCC TAC         2592
Ala Pro Thr Met Arg Glu Gly Gln Ala Tyr Pro Ala Asn Val Pro Tyr
        850                 855                 860

CCA CTA ATA GGC AAA ACC GCG GTT GAC AGT ATT ACC CAG AAA AAG TTT         2640
Pro Leu Ile Gly Lys Thr Ala Val Asp Ser Ile Thr Gln Lys Lys Phe
865                 870                 875

CTT TGC GAT CGC ACC CTT TGG CGC ATC CCA TTC TCC AGT AAC TTT ATG         2688
Leu Cys Asp Arg Thr Leu Trp Arg Ile Pro Phe Ser Ser Asn Phe Met
880                 885                 890                 895

TCC ATG GGC GCA CTC ACA GAC CTG GGC CAA AAC CTT CTC TAC GCC AAC         2736
Ser Met Gly Ala Leu Thr Asp Leu Gly Gln Asn Leu Leu Tyr Ala Asn
                900                 905                 910

TCC GCC CAC GCG CTA GAC ATG ACT TTT GAG GTG GAT CCC ATG GAC GAG         2784
Ser Ala His Ala Leu Asp Met Thr Phe Glu Val Asp Pro Met Asp Glu
            915                 920                 925

CCC ACC CTT CTT TAT GTT TTG TTT GAA GTC TTT GAC GTG GTC CGT GTG         2832
Pro Thr Leu Leu Tyr Val Leu Phe Glu Val Phe Asp Val Val Arg Val
        930                 935                 940

CAC CAG CCG CAC CGC GGC GTC ATC GAG ACC GTG TAC CTG CGC ACG CCC         2880
His Gln Pro His Arg Gly Val Ile Glu Thr Val Tyr Leu Arg Thr Pro
945                 950                 955

TTC TCG GCC GGC AAC GCC ACA ACA TAA                                     2907
Phe Ser Ala Gly Asn Ala Thr Thr
960                 965

(2) INFORMATION FOR SEQ ID NO:56:

(i) SEQUENCE CHARACTERISTICS:
        (A) LENGTH: 967 amino acids
        (B) TYPE: amino acid
        (D) TOPOLOGY: linear (ii) MOLECULE TYPE: protein (xi) SEQUENCE DESCRIPTION: SEQ ID NO:56:

Ala Thr Pro Ser Met Met Pro Gln Trp Ser Tyr Met His Ile Ser Gly
1               5                   10                  15

Gln Asp Ala Ser Glu Tyr Leu Ser Pro Gly Leu Val Gln Phe Ala Arg
            20                  25                  30

Ala Thr Glu Thr Tyr Phe Ser Leu Asn Asn Lys Phe Arg Asn Pro Thr
        35                  40                  45

Val Ala Pro Thr His Asp Val Thr Thr Asp Arg Ser Gln Arg Leu Thr
    50                  55                  60

Leu Arg Phe Ile Pro Val Asp Arg Glu Asp Thr Ala Tyr Ser Tyr Lys
65                  70                  75                  80

Ala Arg Phe Thr Leu Ala Val Gly Asp Asn Arg Val Leu Asp Met Ala
                85                  90                  95

Ser Thr Tyr Phe Asp Ile Arg Gly Val Leu Asp Arg Gly Pro Thr Phe
            100                 105                 110

Lys Pro Tyr Ser Gly Thr Ala Tyr Asn Ala Leu Ala Pro Lys Gly Ala
        115                 120                 125

Pro Asn Ser Cys Glu Trp Glu Gln Thr Glu Asp Ser Gly Arg Ala Val
    130                 135                 140

Ala Glu Asp Glu Glu Glu Asp Glu Asp Glu Glu Glu Glu Glu
145                 150                 155                 160

Glu Gln Asn Ala Arg Asp Gln Ala Thr Lys Lys Thr His Val Tyr Ala
                165                 170                 175

Gln Ala Pro Leu Ser Gly Glu Thr Ile Thr Lys Ser Gly Leu Gln Ile
            180                 185                 190
```

-continued

```
Gly Ser Asp Asn Ala Glu Thr Gln Ala Lys Pro Val Tyr Ala Asp Pro
        195                 200                 205

Ser Tyr Gln Pro Glu Pro Gln Ile Gly Glu Ser Gln Trp Asn Glu Ala
        210                 215                 220

Asp Ala Asn Ala Ala Gly Gly Arg Val Leu Lys Lys Thr Thr Pro Met
225                 230                 235                 240

Lys Pro Cys Tyr Gly Ser Tyr Ala Arg Pro Thr Asn Pro Phe Gly Gly
                245                 250                 255

Gln Ser Val Leu Val Pro Asp Glu Lys Gly Val Pro Leu Pro Lys Val
                260                 265                 270

Asp Leu Gln Phe Phe Ser Asn Thr Thr Ser Leu Asn Asp Arg Gln Gly
        275                 280                 285

Asn Ala Thr Lys Pro Lys Val Val Leu Tyr Ser Glu Asp Val Asn Met
        290                 295                 300

Glu Thr Pro Asp Thr His Leu Ser Tyr Lys Pro Gly Lys Gly Asp Glu
305                 310                 315                 320

Asn Ser Lys Ala Met Leu Gly Gln Gln Ser Met Pro Asn Arg Pro Asn
                325                 330                 335

Tyr Ile Ala Phe Arg Asp Asn Phe Ile Gly Leu Met Tyr Tyr Asn Ser
                340                 345                 350

Thr Gly Asn Met Gly Val Leu Ala Gly Gln Ala Ser Gln Leu Asn Ala
        355                 360                 365

Val Val Asp Leu Gln Asp Arg Asn Thr Glu Leu Ser Tyr Gln Leu Leu
370                 375                 380

Leu Asp Ser Ile Gly Asp Arg Thr Arg Tyr Phe Ser Met Trp Asn Gln
385                 390                 395                 400

Ala Val Asp Ser Tyr Asp Pro Asp Val Arg Ile Ile Glu Asn His Gly
                405                 410                 415

Thr Glu Asp Glu Leu Pro Asn Tyr Cys Phe Pro Leu Gly Gly Ile Gly
                420                 425                 430

Val Thr Asp Thr Tyr Gln Ala Ile Lys Ala Asn Gly Asn Gly Ser Gly
                435                 440                 445

Asp Asn Gly Asp Thr Thr Trp Thr Lys Asp Glu Thr Phe Ala Thr Arg
450                 455                 460

Asn Glu Ile Gly Val Gly Asn Asn Phe Ala Met Glu Ile Asn Leu Asn
465                 470                 475                 480

Ala Asn Leu Trp Arg Asn Phe Leu Tyr Ser Asn Ile Ala Leu Tyr Leu
                485                 490                 495

Pro Asp Lys Leu Lys Tyr Asn Pro Thr Asn Val Glu Ile Ser Asp Asn
                500                 505                 510

Pro Asn Thr Tyr Asp Tyr Met Asn Lys Arg Val Val Ala Pro Gly Leu
                515                 520                 525

Val Asp Cys Tyr Ile Asn Leu Gly Ala Arg Trp Ser Leu Asp Tyr Met
                530                 535                 540

Asp Asn Val Asn Pro Phe Asn His His Arg Asn Ala Gly Leu Arg Tyr
545                 550                 555                 560

Arg Ser Met Leu Leu Gly Asn Gly Arg Tyr Val Pro Phe His Ile Gln
                565                 570                 575

Val Pro Gln Lys Phe Phe Ala Ile Lys Asn Leu Leu Leu Leu Pro Gly
                580                 585                 590

Ser Tyr Thr Tyr Glu Trp Asn Phe Arg Lys Asp Val Asn Met Val Leu
                595                 600                 605
```

```
Gln Ser Ser Leu Gly Asn Asp Leu Arg Val Asp Gly Ala Ser Ile Lys
    610                 615                 620

Phe Asp Ser Ile Cys Leu Tyr Ala Thr Phe Pro Met Ala His Asn
625                 630                 635                 640

Thr Ala Ser Thr Leu Glu Ala Met Leu Arg Asn Asp Thr Asn Asp Gln
                645                 650                 655

Ser Phe Asn Asp Tyr Leu Ser Ala Ala Asn Met Leu Tyr Pro Ile Pro
                660                 665                 670

Ala Asn Ala Thr Asn Val Pro Ile Ser Ile Pro Ser Arg Asn Trp Ala
                675                 680                 685

Ala Phe Arg Gly Trp Ala Phe Thr Arg Leu Lys Thr Lys Glu Thr Pro
690                 695                 700

Ser Leu Gly Ser Gly Tyr Asp Pro Tyr Tyr Thr Tyr Ser Gly Ser Ile
705                 710                 715                 720

Pro Tyr Leu Asp Gly Thr Phe Tyr Leu Asn His Thr Phe Lys Lys Val
                725                 730                 735

Ala Ile Thr Phe Asp Ser Ser Val Ser Trp Pro Gly Asn Asp Arg Leu
                740                 745                 750

Leu Thr Pro Asn Glu Phe Glu Ile Lys Arg Ser Val Asp Gly Glu Gly
            755                 760                 765

Tyr Asn Val Ala Gln Cys Asn Met Thr Lys Asp Trp Phe Leu Val Gln
770                 775                 780

Met Leu Ala Asn Tyr Asn Ile Gly Tyr Gln Gly Phe Tyr Ile Pro Glu
785                 790                 795                 800

Ser Tyr Lys Asp Arg Met Tyr Ser Phe Phe Arg Asn Phe Gln Pro Met
                805                 810                 815

Ser Arg Gln Val Val Asp Asp Thr Lys Tyr Lys Glu Tyr Gln Gln Val
                820                 825                 830

Gly Ile Leu His Gln His Asn Asn Ser Gly Phe Val Gly Tyr Leu Ala
                835                 840                 845

Pro Thr Met Arg Glu Gly Gln Ala Tyr Pro Ala Asn Val Pro Tyr Pro
850                 855                 860

Leu Ile Gly Lys Thr Ala Val Asp Ser Ile Thr Gln Lys Lys Phe Leu
865                 870                 875                 880

Cys Asp Arg Thr Leu Trp Arg Ile Pro Phe Ser Ser Asn Phe Met Ser
                885                 890                 895

Met Gly Ala Leu Thr Asp Leu Gly Gln Asn Leu Leu Tyr Ala Asn Ser
                900                 905                 910

Ala His Ala Leu Asp Met Thr Phe Glu Val Asp Pro Met Asp Glu Pro
            915                 920                 925

Thr Leu Leu Tyr Val Leu Phe Glu Val Phe Asp Val Val Arg Val His
            930                 935                 940

Gln Pro His Arg Gly Val Ile Glu Thr Val Tyr Leu Arg Thr Pro Phe
945                 950                 955                 960

Ser Ala Gly Asn Ala Thr Thr
                965
```

(2) INFORMATION FOR SEQ ID NO:57:

(i) SEQUENCE CHARACTERISTICS:
        (A) LENGTH: 2858 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

```
ATG GCT ACC CCT TCG ATG ATG CCG CAG TGG TCT TAC ATG CAC ATC TCG      48
Ala Thr Pro Ser Met Met Pro Gln Trp Ser Tyr Met His Ile Ser
 1               5                  10                  15

GGC CAG GAC GCC TCG GAG TAC CTG AGC CCC GGG CTG GTG CAG TTT GCC      96
Gly Gln Asp Ala Ser Glu Tyr Leu Ser Pro Gly Leu Val Gln Phe Ala
                20                  25                  30

CGC GCC ACC GAG ACG TAC TTC AGC CTG AAT AAC AAG TTT AGA AAC CCC     144
Arg Ala Thr Glu Thr Tyr Phe Ser Leu Asn Asn Lys Phe Arg Asn Pro
            35                  40                  45

ACG GTG GCG CCT ACG CAC GAC GTG ACC ACA GAC CGG TCC CAG CGT TTG     192
Thr Val Ala Pro Thr His Asp Val Thr Thr Asp Arg Ser Gln Arg Leu
        50                  55                  60

ACG CTG CGG TTC ATC CCT GTG GAC CGT GAG GAT ACT GCG TAC TCG TAC     240
Thr Leu Arg Phe Ile Pro Val Asp Arg Glu Asp Thr Ala Tyr Ser Tyr
    65                  70                  75

AAG GCG CGG TTC ACC CTA GCT GTG GGT GAT AAC CGT GTG CTG GAC ATG     288
Lys Ala Arg Phe Thr Leu Ala Val Gly Asp Asn Arg Val Leu Asp Met
 80                  85                  90                  95

GCT TCC ACG TAC TTT GAC ATC CGC GGC GTG CTG GAC AGG GGC CCT ACT     336
Ala Ser Thr Tyr Phe Asp Ile Arg Gly Val Leu Asp Arg Gly Pro Thr
                100                 105                 110

TTT AAG CCC TAC TCT GGC ACT GCC TAC AAC GCC CTG GCT CCC AAG GGT     384
Phe Lys Pro Tyr Ser Gly Thr Ala Tyr Asn Ala Leu Ala Pro Lys Gly
            115                 120                 125

GCC CCA AAT CCT TGC GAA TGG GAT GAA GCT GCT ACT GCT CTT GAA ATA     432
Ala Pro Asn Pro Cys Glu Trp Asp Glu Ala Ala Thr Ala Leu Glu Ile
        130                 135                 140

AAC CTA GAA GAA GAG GAC GAT GAC AAC GAA GAC GAA GTA GAC GAG CAA     480
Asn Leu Glu Glu Glu Asp Asp Asp Asn Glu Asp Glu Val Asp Glu Gln
    145                 150                 155

GCT GAG CAG CAA AAA ACT CAC GTA TTT GGG CAG GCG CCT TAT TCT GGT     528
Ala Glu Gln Gln Lys Thr His Val Phe Gly Gln Ala Pro Tyr Ser Gly
160                 165                 170                 175

ATA AAT ATT ACA AAG GAG GGT ATT CAA ATA GGT GTC GAA GGT CAA ACA     576
Ile Asn Ile Thr Lys Glu Gly Ile Gln Ile Gly Val Glu Gly Gln Thr
                180                 185                 190

CCT AAA TAT GCC GAT AAA ACA TTT CAA CCT GAA CCT CAA ATA GGA GAA     624
Pro Lys Tyr Ala Asp Lys Thr Phe Gln Pro Glu Pro Gln Ile Gly Glu
            195                 200                 205

TCT CAG TGG TAC GAA ACT GAA ATT AAT CAT GCA GCT GGG AGA GTC CTT     672
Ser Gln Trp Tyr Glu Thr Glu Ile Asn His Ala Ala Gly Arg Val Leu
        210                 215                 220

AAA AAG ACT ACC CCA ATG AAA CCA TGT TAC GGT TCA TAT GCA AAA CCC     720
Lys Lys Thr Thr Pro Met Lys Pro Cys Tyr Gly Ser Tyr Ala Lys Pro
    225                 230                 235

ACA AAT GAA AAT GGA GGG CAA GGC ATT CTT GTA AAG CAA CAA AAT GGA     768
Thr Asn Glu Asn Gly Gly Gln Gly Ile Leu Val Lys Gln Gln Asn Gly
240                 245                 250                 255

AAG CTA GAA AGT CAA GTG GAA ATG CAA TTT TTC TCA ACT ACT GAG GCG     816
Lys Leu Glu Ser Gln Val Glu Met Gln Phe Phe Ser Thr Thr Glu Ala
                260                 265                 270

ACC GCA GGC AAT GGT GAT AAC TTG ACT CCT AAA GTG GTA TTG TAC AGT     864
Thr Ala Gly Asn Gly Asp Asn Leu Thr Pro Lys Val Val Leu Tyr Ser
            275                 280                 285

GAA GAT GTA GAT ATA GAA ACC CCA GAC ACT CAT ATT TCT TAC ATG CCC     912
Glu Asp Val Asp Ile Glu Thr Pro Asp Thr His Ile Ser Tyr Met Pro
        290                 295                 300
```

```
ACT ATT AAG GAA GGT AAC TCA CGA GAA CTA ATG GGC CAA CAA TCT ATG        960
Thr Ile Lys Glu Gly Asn Ser Arg Glu Leu Met Gly Gln Gln Ser Met
    305                 310                 315

CCC AAC AGG CCT AAT TAC ATT GCT TTT AGG GAC AAT TTT ATT GGT CTA       1008
Pro Asn Arg Pro Asn Tyr Ile Ala Phe Arg Asp Asn Phe Ile Gly Leu
320                 325                 330                 335

ATG TAT TAC AAC AGC ACG GGT AAT ATG GGT GTT CTG GCG GGC CAA GCA       1056
Met Tyr Tyr Asn Ser Thr Gly Asn Met Gly Val Leu Ala Gly Gln Ala
                340                 345                 350

TCG CAG TTG AAT GCT GTT GTA GAT TTG CAA GAC AGA AAC ACA GAG CTT       1104
Ser Gln Leu Asn Ala Val Val Asp Leu Gln Asp Arg Asn Thr Glu Leu
            355                 360                 365

TCA TAC CAG CTT TTG CTT GAT TCC ATT GGT GAT AGA ACC AGG TAC TTT       1152
Ser Tyr Gln Leu Leu Leu Asp Ser Ile Gly Asp Arg Thr Arg Tyr Phe
        370                 375                 380

TCT ATG TGG AAT CAG GCT GTT GAC AGC TAT GAT CCA GAT GTT AGA ATT       1200
Ser Met Trp Asn Gln Ala Val Asp Ser Tyr Asp Pro Asp Val Arg Ile
385                 390                 395

ATT GAA AAT CAT GGA ACT GAA GAT GAA CTT CCA AAT TAC TGC TTT CCA       1248
Ile Glu Asn His Gly Thr Glu Asp Glu Leu Pro Asn Tyr Cys Phe Pro
400                 405                 410                 415

CTG GGA GGT GTG ATT AAT ACA GAG ACT CTT ACC AAG GTA AAA CCT AAA       1296
Leu Gly Gly Val Ile Asn Thr Glu Thr Leu Thr Lys Val Lys Pro Lys
                420                 425                 430

ACA GGT CAG GAA AAT GGA TGG GAA AAA GAT GCT ACA GAA TTT TCA GAT       1344
Thr Gly Gln Glu Asn Gly Trp Glu Lys Asp Ala Thr Glu Phe Ser Asp
            435                 440                 445

AAA AAT GAA ATA AGA GTT GGA AAT AAT TTT GCC ATG GAA ATC AAT CTA       1392
Lys Asn Glu Ile Arg Val Gly Asn Asn Phe Ala Met Glu Ile Asn Leu
        450                 455                 460

AAT GCC AAC CTG TGG AGA AAT TTC CTG TAC TCC AAC ATA GCG CTG TAT       1440
Asn Ala Asn Leu Trp Arg Asn Phe Leu Tyr Ser Asn Ile Ala Leu Tyr
    465                 470                 475

TTG CCC GAC AAG CTA AAG TAC AGT CCT TCC AAC GTA AAA ATT TCT GAT       1488
Leu Pro Asp Lys Leu Lys Tyr Ser Pro Ser Asn Val Lys Ile Ser Asp
480                 485                 490                 495

AAC CCA AAC ACC TAC GAC TAC ATG AAC AAG CGA GTG GTG GCT CCC GGG       1536
Asn Pro Asn Thr Tyr Asp Tyr Met Asn Lys Arg Val Val Ala Pro Gly
                500                 505                 510

TTA GTG GAC TGC TAC ATT AAC CTT GGA GCA CGC TGG TCC CTT GAC TAT       1584
Leu Val Asp Cys Tyr Ile Asn Leu Gly Ala Arg Trp Ser Leu Asp Tyr
            515                 520                 525

ATG GAC AAC GTC AAC CCA TTT AAC CAC CAC CGC AAT GCT GGC CTG CGC       1632
Met Asp Asn Val Asn Pro Phe Asn His His Arg Asn Ala Gly Leu Arg
        530                 535                 540

TAC CGC TCA ATG TTG CTG GGC AAT GGT CGC TAT GTG CCC TTC CAC ATC       1680
Tyr Arg Ser Met Leu Leu Gly Asn Gly Arg Tyr Val Pro Phe His Ile
    545                 550                 555

CAG GTG CCT CAG AAG TTC TTT GCC ATT AAA AAC CTC CTT CTC CTG CCG       1728
Gln Val Pro Gln Lys Phe Phe Ala Ile Lys Asn Leu Leu Leu Leu Pro
560                 565                 570                 575

GGC TCA TAC ACC TAC GAG TGG AAC TTC AGG AAG GAT GTT AAC ATG GTT       1776
Gly Ser Tyr Thr Tyr Glu Trp Asn Phe Arg Lys Asp Val Asn Met Val
                580                 585                 590

CTG CAG AGC TCC CTA GGA AAT GAC CTA AGG GTT GAC GGA GCC AGC ATT       1824
Leu Gln Ser Ser Leu Gly Asn Asp Leu Arg Val Asp Gly Ala Ser Ile
            595                 600                 605
```

```
AAG TTT GAT AGC ATT TGC CTT TAC GCC ACC TTC TTC CCC ATG GCC CAC         1872
Lys Phe Asp Ser Ile Cys Leu Tyr Ala Thr Phe Phe Pro Met Ala His
        610                 615                 620

AAC ACC GCC TCC ACG CTT GAG GCC ATG CTT AGA AAC GAC ACC AAC GAC         1920
Asn Thr Ala Ser Thr Leu Glu Ala Met Leu Arg Asn Asp Thr Asn Asp
                625                 630                 635

CAG TCC TTT AAC GAC TAT CTC TCC GCC GCC AAC ATG CTC TAC CCT ATA         1968
Gln Ser Phe Asn Asp Tyr Leu Ser Ala Ala Asn Met Leu Tyr Pro Ile
640                 645                 650                 655

CCC GCC AAC GCT ACC AAC GTG CCC ATA TCC ATC CCC TCC CGC AAC TGG         2016
Pro Ala Asn Ala Thr Asn Val Pro Ile Ser Ile Pro Ser Arg Asn Trp
                    660                 665                 670

GCG GCT TTC CGC GGC TGG GCC TTC ACG CGC CTT AAG ACT AAG GAA ACC         2064
Ala Ala Phe Arg Gly Trp Ala Phe Thr Arg Leu Lys Thr Lys Glu Thr
            675                 680                 685

CCA TCA CTG GGC TCG GGC TAC GAC CCT TAT TAC ACC TAC TCT GGC TCT         2112
Pro Ser Leu Gly Ser Gly Tyr Asp Pro Tyr Tyr Thr Tyr Ser Gly Ser
        690                 695                 700

ATA CCC TAC CTA GAT GGA ACC TTT TAC CTC AAC CAC ACC TTT AAG AAG         2160
Ile Pro Tyr Leu Asp Gly Thr Phe Tyr Leu Asn His Thr Phe Lys Lys
705                 710                 715

GTG GCC ATT ACC TTT GAC TCT TCT GTC AGC TGG CCT GGC AAT GAC CGC         2208
Val Ala Ile Thr Phe Asp Ser Ser Val Ser Trp Pro Gly Asn Asp Arg
720                 725                 730                 735

CTG CTT ACC CCC AAC GAG TTT GAA ATT AAG CGC TCA GTT GAC GGG GAG         2256
Leu Leu Thr Pro Asn Glu Phe Glu Ile Lys Arg Ser Val Asp Gly Glu
                740                 745                 750

GGT TAC AAC GTT GCC CAG TGT AAC ATG ACC AAA GAC TGG TTC CTG GTA         2304
Gly Tyr Asn Val Ala Gln Cys Asn Met Thr Lys Asp Trp Phe Leu Val
            755                 760                 765

CAA ATG CTA GCT AAC TAC AAC ATT GGC TAC CAG GGC TTC TAT ATC CCA         2352
Gln Met Leu Ala Asn Tyr Asn Ile Gly Tyr Gln Gly Phe Tyr Ile Pro
        770                 775                 780

GAG AGC TAC AAG GAC CGC ATG TAC TCC TTC TTT AGA AAC TTC CAG CCC         2400
Glu Ser Tyr Lys Asp Arg Met Tyr Ser Phe Phe Arg Asn Phe Gln Pro
785                 790                 795

ATG AGC CGT CAG GTG GTG GAT GAT ACT AAA TAC AAG GAC TAC CAA CAG         2448
Met Ser Arg Gln Val Val Asp Asp Thr Lys Tyr Lys Asp Tyr Gln Gln
800                 805                 810                 815

GTG GGC ATC CTA CAC CAA CAC AAC AAC TCT GGA TTT GTT GGC TAC CTT         2496
Val Gly Ile Leu His Gln His Asn Asn Ser Gly Phe Val Gly Tyr Leu
                820                 825                 830

GCC CCC ACC ATG CGC GAA GGA CAG GCC TAC CCT GCT AAC TTC CCC TAT         2544
Ala Pro Thr Met Arg Glu Gly Gln Ala Tyr Pro Ala Asn Phe Pro Tyr
            835                 840                 845

CCG CTT ATA GGC AAG ACC GCA GTT GAC AGC ATT ACC CAG AAA AAG TTT         2592
Pro Leu Ile Gly Lys Thr Ala Val Asp Ser Ile Thr Gln Lys Lys Phe
        850                 855                 860

CTT TGC GAT CGC ACC CTT TGG CGC ATC CCA TTC TCC AGT AAC TTT ATG         2640
Leu Cys Asp Arg Thr Leu Trp Arg Ile Pro Phe Ser Ser Asn Phe Met
865                 870                 875

TCC ATG GGC GCA CTC ACA GAC CTG GGC CAA AAC CTT CTC TAC GCC AAC         2688
Ser Met Gly Ala Leu Thr Asp Leu Gly Gln Asn Leu Leu Tyr Ala Asn
880                 885                 890                 895

TCC GCC CAC GCG CTA GAC ATG ACT TTT GAG GTG GAT CCC ATG GAC GAG         2736
Ser Ala His Ala Leu Asp Met Thr Phe Glu Val Asp Pro Met Asp Glu
                900                 905                 910

CCC ACC CTT CTT TAT GTT TTG TTT GAA GTC TTT GAC GTG GTC CGT GTG         2784
Pro Thr Leu Leu Tyr Val Leu Phe Glu Val Phe Asp Val Val Arg Val
            915                 920                 925
```

```
CAC CGG CCG CAC CGC GGC GTC ATC GAA ACC GTG TAC CTG CGC ACG CCC    2832
His Arg Pro His Arg Gly Val Ile Glu Thr Val Tyr Leu Arg Thr Pro
        930                     935                     940

TTC TCG GCC GGC AAC GCA CAA CAT AA                                 2858
Phe Ser Ala Gly Asn Ala Gln His
945                 950
```

(2) INFORMATION FOR SEQ ID NO:58:

(i) SEQUENCE CHARACTERISTICS:
        (A) LENGTH: 951 amino acids
        (B) TYPE: amino acid
        (D) TOPOLOGY: linear (ii) MOLECULE TYPE: protein (xi) SEQUENCE DESCRIPTION: SEQ ID NO:58:

```
Ala Thr Pro Ser Met Met Pro Gln Trp Ser Tyr Met His Ile Ser Gly
 1               5                  10                  15

Gln Asp Ala Ser Glu Tyr Leu Ser Pro Gly Leu Val Gln Phe Ala Arg
                20                  25                  30

Ala Thr Glu Thr Tyr Phe Ser Leu Asn Asn Lys Phe Arg Asn Pro Thr
            35                  40                  45

Val Ala Pro Thr His Asp Val Thr Thr Asp Arg Ser Gln Arg Leu Thr
        50                  55                  60

Leu Arg Phe Ile Pro Val Asp Arg Glu Asp Thr Ala Tyr Ser Tyr Lys
65                  70                  75                  80

Ala Arg Phe Thr Leu Ala Val Gly Asp Asn Arg Val Leu Asp Met Ala
                85                  90                  95

Ser Thr Tyr Phe Asp Ile Arg Gly Val Leu Asp Arg Gly Pro Thr Phe
            100                 105                 110

Lys Pro Tyr Ser Gly Thr Ala Tyr Asn Ala Leu Ala Pro Lys Gly Ala
        115                 120                 125

Pro Asn Pro Cys Glu Trp Asp Glu Ala Ala Thr Ala Leu Glu Ile Asn
    130                 135                 140

Leu Glu Glu Glu Asp Asp Asp Asn Glu Asp Glu Val Asp Glu Gln Ala
145                 150                 155                 160

Glu Gln Gln Lys Thr His Val Phe Gly Gln Ala Pro Tyr Ser Gly Ile
                165                 170                 175

Asn Ile Thr Lys Glu Gly Ile Gln Ile Gly Val Glu Gly Gln Thr Pro
            180                 185                 190

Lys Tyr Ala Asp Lys Thr Phe Gln Pro Glu Pro Gln Ile Gly Glu Ser
        195                 200                 205

Gln Trp Tyr Glu Thr Glu Ile Asn His Ala Ala Gly Arg Val Leu Lys
    210                 215                 220

Lys Thr Thr Pro Met Lys Pro Cys Tyr Gly Ser Tyr Ala Lys Pro Thr
225                 230                 235                 240

Asn Glu Asn Gly Gly Gln Gly Ile Leu Val Lys Gln Gln Asn Gly Lys
                245                 250                 255

Leu Glu Ser Gln Val Glu Met Gln Phe Phe Ser Thr Thr Glu Ala Thr
            260                 265                 270

Ala Gly Asn Gly Asp Asn Leu Thr Pro Lys Val Val Leu Tyr Ser Glu
        275                 280                 285

Asp Val Asp Ile Glu Thr Pro Asp Thr His Ile Ser Tyr Met Pro Thr
    290                 295                 300
```

```
Ile Lys Glu Gly Asn Ser Arg Glu Leu Met Gly Gln Ser Met Pro
305                 310                 315                 320

Asn Arg Pro Asn Tyr Ile Ala Phe Arg Asp Asn Phe Ile Gly Leu Met
            325                 330                 335

Tyr Tyr Asn Ser Thr Gly Asn Met Gly Val Leu Ala Gly Gln Ala Ser
            340                 345                 350

Gln Leu Asn Ala Val Val Asp Leu Gln Asp Arg Asn Thr Glu Leu Ser
            355                 360                 365

Tyr Gln Leu Leu Leu Asp Ser Ile Gly Asp Arg Thr Arg Tyr Phe Ser
370                 375                 380

Met Trp Asn Gln Ala Val Asp Ser Tyr Asp Pro Asp Val Arg Ile Ile
385                 390                 395                 400

Glu Asn His Gly Thr Glu Asp Glu Leu Pro Asn Tyr Cys Phe Pro Leu
            405                 410                 415

Gly Gly Val Ile Asn Thr Glu Thr Leu Thr Lys Val Lys Pro Lys Thr
            420                 425                 430

Gly Gln Glu Asn Gly Trp Glu Lys Asp Ala Thr Glu Phe Ser Asp Lys
            435                 440                 445

Asn Glu Ile Arg Val Gly Asn Asn Phe Ala Met Glu Ile Asn Leu Asn
450                 455                 460

Ala Asn Leu Trp Arg Asn Phe Leu Tyr Ser Asn Ile Ala Leu Tyr Leu
465                 470                 475                 480

Pro Asp Lys Leu Lys Tyr Ser Pro Ser Asn Val Lys Ile Ser Asp Asn
            485                 490                 495

Pro Asn Thr Tyr Asp Tyr Met Asn Lys Arg Val Val Ala Pro Gly Leu
            500                 505                 510

Val Asp Cys Tyr Ile Asn Leu Gly Ala Arg Trp Ser Leu Asp Tyr Met
            515                 520                 525

Asp Asn Val Asn Pro Phe Asn His His Arg Asn Ala Gly Leu Arg Tyr
            530                 535                 540

Arg Ser Met Leu Leu Gly Asn Gly Arg Tyr Val Pro Phe His Ile Gln
545                 550                 555                 560

Val Pro Gln Lys Phe Phe Ala Ile Lys Asn Leu Leu Leu Leu Pro Gly
            565                 570                 575

Ser Tyr Thr Tyr Glu Trp Asn Phe Arg Lys Asp Val Asn Met Val Leu
            580                 585                 590

Gln Ser Ser Leu Gly Asn Asp Leu Arg Val Asp Gly Ala Ser Ile Lys
            595                 600                 605

Phe Asp Ser Ile Cys Leu Tyr Ala Thr Phe Phe Pro Met Ala His Asn
            610                 615                 620

Thr Ala Ser Thr Leu Glu Ala Met Leu Arg Asn Asp Thr Asn Asp Gln
625                 630                 635                 640

Ser Phe Asn Asp Tyr Leu Ser Ala Ala Asn Met Leu Tyr Pro Ile Pro
            645                 650                 655

Ala Asn Ala Thr Asn Val Pro Ile Ser Ile Pro Ser Arg Asn Trp Ala
            660                 665                 670

Ala Phe Arg Gly Trp Ala Phe Thr Arg Leu Lys Thr Lys Glu Thr Pro
            675                 680                 685

Ser Leu Gly Ser Gly Tyr Asp Pro Tyr Tyr Thr Tyr Ser Gly Ser Ile
            690                 695                 700

Pro Tyr Leu Asp Gly Thr Phe Tyr Leu Asn His Thr Phe Lys Lys Val
705                 710                 715                 720
```

```
Ala Ile Thr Phe Asp Ser Ser Val Ser Trp Pro Gly Asn Asp Arg Leu
                725                 730                 735

Leu Thr Pro Asn Glu Phe Glu Ile Lys Arg Ser Val Asp Gly Glu Gly
            740                 745                 750

Tyr Asn Val Ala Gln Cys Asn Met Thr Lys Asp Trp Phe Leu Val Gln
            755                 760                 765

Met Leu Ala Asn Tyr Asn Ile Gly Tyr Gln Gly Phe Tyr Ile Pro Glu
    770                 775                 780

Ser Tyr Lys Asp Arg Met Tyr Ser Phe Phe Arg Asn Phe Gln Pro Met
785                 790                 795                 800

Ser Arg Gln Val Val Asp Asp Thr Lys Tyr Lys Asp Tyr Gln Gln Val
                805                 810                 815

Gly Ile Leu His Gln His Asn Asn Ser Gly Phe Val Gly Tyr Leu Ala
                820                 825                 830

Pro Thr Met Arg Glu Gly Gln Ala Tyr Pro Ala Asn Phe Pro Tyr Pro
            835                 840                 845

Leu Ile Gly Lys Thr Ala Val Asp Ser Ile Thr Gln Lys Lys Phe Leu
    850                 855                 860

Cys Asp Arg Thr Leu Trp Arg Ile Pro Phe Ser Ser Asn Phe Met Ser
865                 870                 875                 880

Met Gly Ala Leu Thr Asp Leu Gly Gln Asn Leu Leu Tyr Ala Asn Ser
                885                 890                 895

Ala His Ala Leu Asp Met Thr Phe Glu Val Asp Pro Met Asp Glu Pro
            900                 905                 910

Thr Leu Leu Tyr Val Leu Phe Glu Val Phe Asp Val Val Arg Val His
            915                 920                 925

Arg Pro His Arg Gly Val Ile Glu Thr Val Tyr Leu Arg Thr Pro Phe
            930                 935                 940

Ser Ala Gly Asn Ala Gln His
945                 950

(2) INFORMATION FOR SEQ ID NO:59:

(i) SEQUENCE CHARACTERISTICS:
        (A) LENGTH: 98 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:59:

GAA CTC GGA GGT GGA GGT GGA ACT AGT TTT GGA CGC GGA GAC ATT CGC      48
Glu Leu Gly Gly Gly Gly Gly Thr Ser Phe Gly Arg Gly Asp Ile Arg
  1               5                  10                  15

AAT TAAAGTACTG GATTCATGAC TCTAGACTTA ATTAAGGATC CAATAAA              98
Asn (2) INFORMATION FOR SEQ ID NO:60:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:60:
```

```
-continued

Glu Leu Gly Gly Gly Gly Gly Thr Ser Phe Gly Arg Gly Asp Ile Arg
 1               5                  10                  15
Asn
```

CHIMERIC ADENOVIRAL COAT PROTEIN AND METHODS OF USING SAME

RELATED APPLICATION

This is a continuation-in-part application of U.S. patent application Ser. No. 08/395,381 filed Feb. 21, 1995 now U.S. Pat. No. 5,770,442.

TECHNICAL FIELD OF THE INVENTION

The present invention relates to a chimeric adenoviral coat protein and a recombinant adenovirus comprising same. In particular, the invention provides a chimeric adenoviral hexon protein and a recombinant adenovirus comprising the chimeric adenoviral hexon protein. Such a recombinant adenovirus can be employed inter alia in gene therapy.

BACKGROUND OF THE INVENTION

In vivo gene therapy is a strategy in which nucleic acid, usually in the form of DNA, is administered to modify the genetic repertoire of target cells for therapeutic purposes. This can be accomplished efficiently using a recombinant adenoviral vector encoding a so-called "therapeutic gene". A therapeutic gene is generally considered a gene that corrects or compensates for an underlying protein deficit or, alternately, a gene that is capable of down-regulating a particular gene, or counteracting the negative effects of its encoded product, in a given disease state or syndrome. Recombinant adenoviral vectors have been used to transfer one or more recombinant genes to diseased cells or tissues in need of treatment. As reviewed by Crystal, *Science*, 270, 404–410 (1995), such vectors are preferred over other vectors commonly employed for gene therapy (e.g., retroviral vectors) since adenoviral vectors can be produced in high titers (i.e., up to $10^{13}$ viral particles/ml), and they efficiently transfer genes to nonreplicating, as well as replicating, cells. Moreover, adenoviral vectors are additionally preferred based on their normal tropism for the respiratory epithelium in cases where the targeted tissue for somatic gene therapy is the lung, as well as for other reasons (see, e.g., Straus, *In Adenoviruses*, Plenan Press, New York, N.Y., 451–496 (1984)); Horwitz et al., *In Virology*, 2nd Ed., Fields et al., eds., Raven Press, New York, N.Y., 1679–1721 (1990); Berkner, *BioTechniques*, 6, 616 (1988); Chanock et al., *JAMA*, 195, 151 (1966); Haj-Ahmad et al., *J. Virol.*, 57, 267 (1986); and Ballay et al., *EMBO*, 4, 3861 (1985)).

There are 49 human adenoviral serotypes, categorized into 6 subgenera (A through F) based on nucleic acid comparisons, fiber protein characteristics, and biological properties (Crawford-Miksza et al., *J. Virol.*, 70, 1836–1844 (1996)). The group C viruses (e.g., serotypes 2 and 5, or Ad2 and Ad5) are well characterized. It is these serotypes that currently are employed for gene transfer studies, including human gene therapy trials (see, e.g., Rosenfeld et al., *Science*, 252, 431–434 (1991); Rosenfeld et al., *Cell*, 68, 143–155 (1992); Zabner, *Cell*, 75, 207–216 (1993); Crystal et al., *Nat. Gen.*, 8, 42–51 (1994); Yei et al., *Gene Therapy*, 1, 192–200 (1994); Chen et al., *Proc. Natl. Acad. Sci.*, 91, 3054–3057 (1994); Yang et al., *Nat. Gen.*, 7, 362–369 (1994); Zabner et al., *Nat. Gen.*, 6, 75–83 (1994)). Other groups and serotypes include, but are not limited to: group A (e.g., serotypes 12 and 31), group B (e.g., serotypes 3 and 7), group D (e.g., serotypes 8 and 30), group E (e.g., serotype 4) and group F (e.g., serotypes 40 and 41) (Horwitz et al., supra).

In terms of general structure, all adenoviruses examined to date are nonenveloped, regular icosahedrons of about 65 to 80 nanometers in diameter. Adenoviruses are comprised of linear, double-stranded DNA that is complexed with core proteins and surrounded by the adenoviral capsid. The capsid is comprised of 252 capsomeres, of which 240 are hexons and 12 are pentons. The hexon capsomere provides structure and form to the capsid (Pettersson, in *The Adenoviruses*, pp. 205–270, Ginsberg, ed., (Plenum Press, New York, N.Y., 1984)), and is a homotrimer of the hexon protein (Roberts et al., *Science*, 232, 1148–1151 (1986)). The penton comprises a penton base, which is bound to other hexon capsomeres, and a fiber, which is noncovalently bound to, and projects from, the penton base. The penton fiber protein comprises three identical polypeptides (i.e., polypeptide IV). The Ad2 penton base protein comprises five identical polypeptides (i.e., polypeptide III) of 571 amino acids each (Boudin et al., *Virology*, 92, 125–138 (1979)).

The adenoviruses provide an elegant and efficient means of transferring therapeutic genes into cells. However, one problem encountered with the use of adenoviral vectors for gene transfer in vivo is the generation of antibodies to antigenic epitopes on adenoviral capsid proteins. If sufficient in titer, the antibodies can limit the ability of the vector to be used more than once as an effective gene transfer vehicle. For instance, animal studies demonstrate that intravenous or local administration (e.g., to the lung, heart or peritoneum) of an adenoviral type 2 or 5 gene transfer vector can result in the production of antibodies directed against the vector which prevent expression from the same serotype vector administered 1 to 2 weeks later (see, e.g., Yei et al., supra; Zabner (1994), supra; Setoguchi et al., *Am. J. Respir. Cell. Mol. Biol.*, 10, 369–377 (1994); Kass-Eisler et al., *Gene Therapy*, 1, 395–402 (1994); Kass-Eisler et al., *Gene Therapy* 3, 154–162 (1996)). This is a drawback in adenoviral-mediated gene therapy, since many uses of an adenoviral vector (e.g., for prolonged gene therapy) require repeat administration inasmuch as the vector does not stably integrate into the host cell genome. The mechanism by which antibodies directed against an adenovirus are able to prevent or reduce expression of an adenoviral-encoded gene is unclear. However, the phenomenon is loosely referred to as "neutralization", and the responsible antibodies are termed "neutralizing antibodies."

There are three capsid structures against which neutralizing antibodies potentially can be elicited: fiber, penton, and hexon (Pettersson, supra). The hexon protein, and to a lesser extent the fiber protein, comprise the main antigenic determinants of the virus, and also determine the serotype specificity of the virus (Watson et al., *J. Gen. Virol.*, 69, 525–535 (1988); Wolfort et al., *J. Virol.*, 62, 2321–2328 (1988); Wolfort et al., *J. Virol.*, 56, 896–903 (1985); Crawford-Miksza et al., supra). Researchers have examined and compared the structure of these coat proteins of different adenoviral serotypes in an effort to define the regions of the proteins against which neutralizing antibodies are elicited.

The Ad2 hexon trimer is comprised of a pseudohexagonal base and a triangular top formed of three towers (Roberts et al., supra; Athappilly et al., *J. Mol. Biol.*, 242, 430–455 (1994)). The base pedestal consists of two tightly packed eight-stranded antiparallel beta barrels stabilized by an internal loop. The predominant regions in hexon protein against which neutralizing antibodies are directed appear to be in loops 1 and 2 (i.e., LI or l1, and LII or l2, respectively) in one of the three towers. For instance, Kinloch et al. (*J. Biol. Chem.*, 258, 6431–6436 (1984)) compared adenoviral hexon sequences and theorized that the serotype-specific antigenic determinants on hexon are located in amino acid residues 120 to 470 encompassing the l1 and l2 loops since type-specific sequence differences are mainly concentrated in this region. Toogood et al. (*J. Gen. Virol.*, 73, 1429–1435 (1992)) used peptides from this region to generate specific anti-loop antisera and confirmed that antibodies against residues 281–292 of l1 and against residues 441–455 of l2 were sufficient to neutralize infection. Also, Crompton et al. (*J. Gen. Virol.*, 75, 133–139 (1994)) modified these loops to accept neutralizing epitopes from polio virus, and demonstrated that infection with the resultant adenoviral vector generated neutralizing immunity against polio virus. More recently it was demonstrated that the hexon protein is composed of seven discrete hypervariable regions in loops and 1 and 2 (HVR1 to HVR7) which vary in length and sequence between adenoviral serotypes (Crawford-Miksza et al., supra).

Less is known regarding the regions of the fiber protein against which neutralizing antibodies potentially can be directed. However, much data is available on the structure of the fiber protein. The trimeric fiber protein consists of a tail, a shaft, and a knob (Devaux et al., *J. Molec. Biol.*, 215, 567–588 (1990)). The fiber shaft region is comprised of repeating 15 amino acid motifs, which are believed to form two alternating beta strands and beta bends (Green et al., *EMBO J.*, 2, 1357–1365 (1983)). The overall length of the fiber shaft region and the number of 15 amino acid repeats differ between adenoviral serotypes. The receptor binding domain of the fiber protein and sequences necessary for fiber trimerization are localized in the knob region encoded by roughly the last 200 amino acids of the protein (Henry et al., *J. Virol.*, 68(8), 5239–5246 (1994)); Xia et al., *Structure*, 2(12), 1259–1270 (1994)). Furthermore, all adenovirus serotypes appear to possess a type of specific moiety located in the knob region (Toogood et al., supra.)

Given the existence of these potential epitopes in hexon protein and fiber protein, it is understandable that, in some cases, difficulties have been encountered using adenovirus as a vector for gene therapy. Accordingly, recombinant adenoviral vectors capable of escaping such neutralizing antibodies (in the event they are preexisting and hamper gene expression commanded by adenovirus in an initial dose), and which would allow repeat doses of adenoviral vectors to be administered, would significantly advance current gene therapy methodology.

Thus, the present invention seeks to overcome at least some of the aforesaid problems of recombinant adenoviral gene therapy. In particular, it is an object of the present invention to provide a recombinant adenovirus comprising a chimeric coat protein that has a decreased ability or inability to be recognized by antibodies (i.e., neutralizing antibodies) directed against the corresponding wild-type adenovirus coat protein. These and other objects and advantages of the present invention, as well as additional inventive features, will be apparent from the description of the invention provided herein.

BRIEF SUMMARY OF THE INVENTION

The present invention provides a chimeric adenovirus coat protein (particularly a chimeric adenovirus hexon protein) comprising a nonnative amino acid sequence. The chimeric adenovirus coat protein is not recognized by, or has a decreased ability to be recognized by, a neutralizing antibody directed against the corresponding wild-type (i.e., native) coat protein. The chimeric adenovirus coat protein enables a vector (such as an adenovirus) comprising the corresponding protein to be administered repetitively, or to be administered following administration of an adenovirus vector comprising the corresponding wild-type coat protein. It also enables a vector (such as an adenovirus) comprising the chimeric protein to be administered and effect gene expression in the case where there are preexisting neutralizing antibodies directed against the wild-type adenovirus coat protein. The present invention also provides a vector, particularly an adenoviral vector, that comprises a chimeric adenovirus coat protein such as chimeric adenovirus hexon protein (and which optionally further comprises a chimeric adenovirus fiber and/or penton base protein), and methods of constructing and using such a vector.

DETAILED DESCRIPTION OF THE INVENTION

Figure 1:
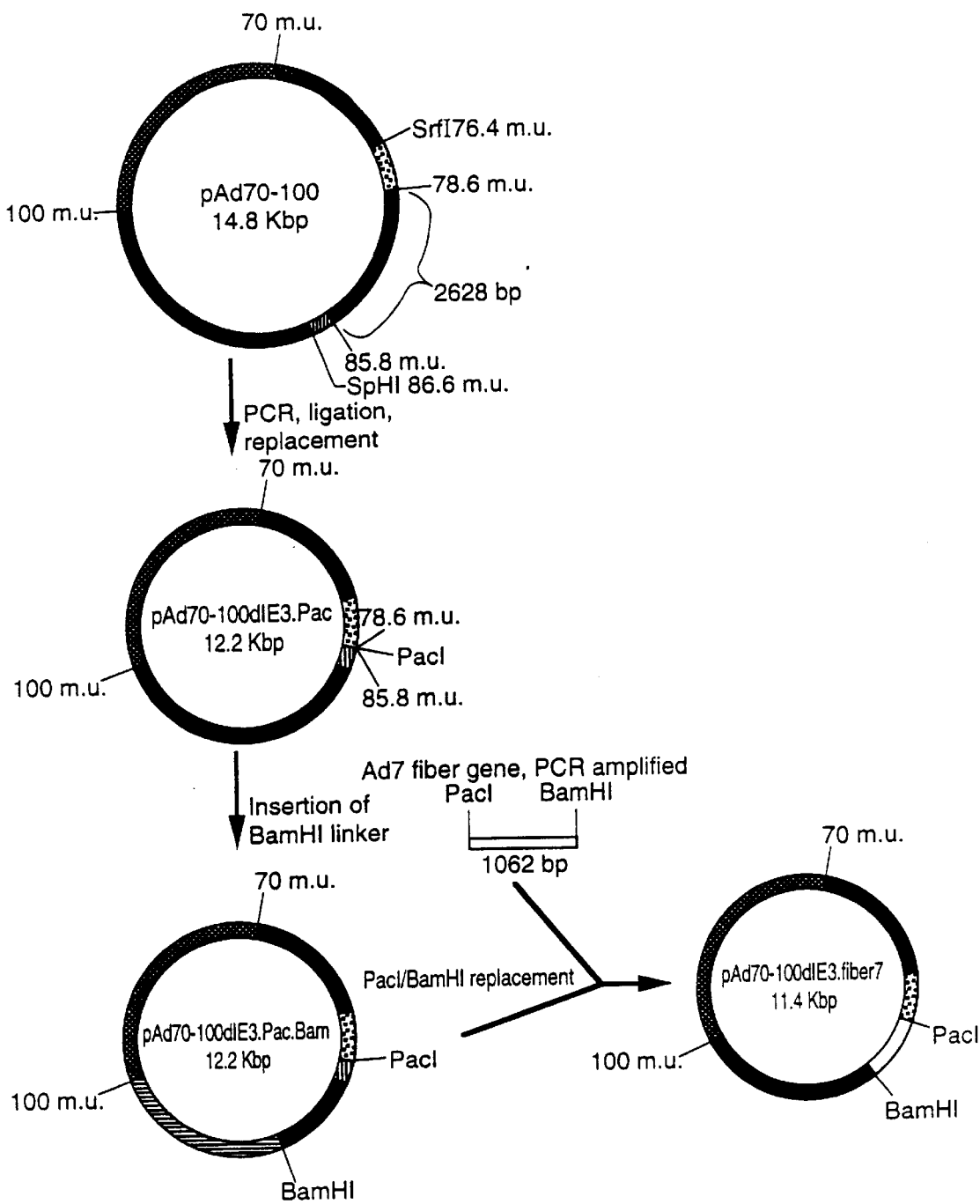
FIG. 1 is a diagram of the method employed to construct the vector pAd70–100dlE3.fiber7.

The present invention provides, among other things, a chimeric adenovirus coat protein. The chimeric adenovirus coat protein comprises a nonnative amino acid sequence, such that the chimeric adenovirus coat protein (or a vector comprising the chimeric adenovirus coat protein) has a decreased ability or inability to be recognized by antibodies (e.g., neutralizing antibodies) directed against the corresponding wild-type adenovirus coat protein.

Chimeric Adenovirus Coat Protein

A "coat protein" according to the invention is either an adenoviral penton base protein, an adenoviral hexon protein, or an adenoviral fiber protein. Preferably a coat protein is a adenoviral hexon protein or an adenoviral fiber protein. Any one of the serotypes of human or nonhuman adenovirus can be used as the source of the coat protein, or its gene or coding sequence. Optimally, however, the adenovirus coat protein is that of a Group B or C adenovirus and, preferably, is that of Ad1, Ad2, Ad3, Ad5, Ads, Ad7, Ad11, Ad12, Ad14, Ad16, Ad21, Ad34, Ad35, Ad40, Ad41, or Ad48.

The chimeric adenovirus coat protein (or a vector, such as adenoviral vector, comprising the chimeric adenovirus coat protein) has a decreased ability or an inability to be recognized by an antibody (e.g., a neutralizing antibody) directed against the corresponding wild-type adenovirus coat protein. A "neutralizing antibody" is an antibody that either is purified from or is present in serum. As used herein, an antibody can be a single antibody or a plurality of antibodies. An antibody is "neutralizing" if it inhibits infectivity of (i.e., cell entry) or gene expression commanded by an adenovirus comprising wild-type coat protein, or if it exerts a substantial deleterious effect on infectivity of or gene expression commanded by an adenovirus comprising wild-type coat protein, as compared, for instance, to any effect on any other adenoviral property.

An ability or inability of a chimeric coat protein to "be recognized by" (i.e., interact with) a neutralizing antibody directed against the wild-type adenovirus coat protein can be assessed by a variety of means known to those skilled in the art. For instance, the removal of one or more epitopes for a neutralizing antibody present in a wild-type adenovirus coat protein to generate a chimeric adenovirus coat protein will result in a decreased ability or inability of the chimeric coat protein to be recognized by the neutralizing antibody. Also, such a decreased ability or inability to interact with a neutralizing antibody directed against wild-type coat protein can be demonstrated by means of a neutralization test (see, e.g., Toogood et al., supra; Crawford-Miksza et al., supra; Mastrangeli et al., *Human Gene Therapy*, 7, 79–87 (1996)), or as further described herein.

Generally, an "inability" of a chimeric adenovirus coat protein (or a vector comprising a chimeric adenovirus coat protein) to be recognized by a neutralizing antibody directed against wild-type adenovirus coat protein means that such an antibody does not interact with the chimeric coat protein, and/or exhibits no substantial deleterious effect on infectivity of or gene expression commanded by an adenovirus comprising wild-type coat protien, as compared, for instance, to any effect on any other adenoviral property.

A "decreased ability" to be recognized by neutralizing antibody directed against wild-type adenovirus coat protein refers to any decrease in the ability of the chimeric adenovirus coat protein (or a vector comprising the chimeric coat protein) to be recognized by an antibody directed against the corresponding wild-type adenovirus coat protein as compared to the wild-type adenovirus coat protein. When such ability/inability is assessed by means of a neutralization test in particular, preferably a "decreased ability" to be recognized by a neutralizing antibody directed against wild-type adenovirus coat protein is exhibited by from about a 10% to about a 99% increase in the ability of a recombinant adenovirus comprising the chimeric coat protein to cause a visible cytopathic effect (c.p.e.) in cells such as A549 cells or COS-1 cells (or other such cells appropriate for a neutralization assay) in the presence of the neutralizing antibody as compared to an adenovirus comprising the wild-type coat protein against which the neutralizing antibody is directed.

Furthermore, a decreased ability or inability of an adenovirus chimeric coat protein (or a vector comprising a chimeric adenovirus coat protein) to interact with a neutralizing antibody can be shown by a reduction of inhibition (from about 10% to about 99%) or no inhibition at all of cell infectivity by a recombinant vector (such as an adenoviral vector) containing the chimeric coat protein as compared to a recombinant vector containing the wild-type protein. Also, a decreased ability or inability of an adenovirus chimeric coat protein (or a vector comprising a chimeric adenovirus coat protein) to interact with a neutralizing antibody can be shown by a reduction of inhibition (from about 10% to about 99%) or no inhibition at all of gene expression commanded by a recombinant vector (such as an adenoviral vector) containing the chimeric coat protein as compared to a recombinant vector containing the wild-type coat protein. These tests can be carried out when the recombinant adenovirus containing the chimeric coat protein is administered following the administration of an adenovirus containing the wild-type coat protein, or when the recombinant adenovirus is administered to a host that has never before encountered or internalized adenovirus (i.e., a "naive" host). These methods are described, for instance, in the Examples which follow as well as in Mastrangeli et al., supra. Other means such as are known to those skilled in the art also can be employed.

The coat protein is "chimeric" in that it comprises a sequence of amino acid residues that is not typically found in the protein as isolated from, or identified in, wild-type adenovirus, which comprises the so-called native coat protein, or "wild-type coat protein". The chimeric coat protein thus comprises (or has) a "nonnative amino acid sequence". By "nonnative amino acid sequence" is meant any amino acid sequence (i.e., either component residues or order thereof) that is not found in the native coat protein of a given serotype of adenovirus, and which preferably is introduced into the coat protein at the level of gene expression (i.e., by production of a nucleic acid sequence that encodes the nonnative amino acid sequence). Generally, the nonnative amino acid sequence can be obtained by deleting a portion of the amino acid sequence, deleting a portion of the amino acid sequence and replacing the deleted amino sequence with a so-called "spacer region", or introducing the spacer region into an unmodified coat protein. Preferably such manipulations result in a chimeric adenovirus coat protein according to the invention that is capable of carrying out the functions of the corresponding wild-type adenovirus coat protein (or, at least that when incorporated into an adenovirus, will allow appropriate virion formation and will not preclude adenoviral-mediated cell entry), and, optimally, that is not impeded in its proper folding. Also, it is desirable that the manipulations do not result in the creation of new epitopes for differing antibodies, unless, of course, such epitopes do not interfere with use of an adenovirus containing the chimeric coat protein as a gene transfer vehicle in vivo.

In particular, a nonnative amino acid sequence according to the invention preferably comprises a deletion of a region of a wild-type adenovirus coat protein, particularly an adenovirus hexon or fiber protein. Optimally the resultant nonnative amino acid sequence is such that one or more of the existing epitopes for neutralizing antibodies directed against the corresponding wild-type adenovirus coat protein have been rendered non-immunogenic. Desirably, the region deleted comprises from about 1 to about 750 amino acids, preferably from about 1 to about 500 amino acids, and optimally from about 1 to about 300 amino acids. It also is desirable that the region deleted comprises a smaller region less than about 200 amino acids, preferably less than about 100 amino acids, and optimally less than about 50 amino acids. The chimeric coat protein also desirably comprises a plurality of such deletions. Thus, according to the invention, the chimeric adenovirus coat protein comprises modification of one or more amino acids, and such modification is made in one or more regions.

In a preferred embodiment of the present invention, a nonnative amino acid sequence comprises a deletion of one or more regions of a wild-type adenovirus hexon protein, wherein preferably the hexon protein is the Ad2 hexon protein [SEQ ID NO:2] (which is encoded by the sequence of SEQ ID NO:1; GenBank® Data Bank Accession Number U20821), or the Ad5 hexon protein [SEQ ID NO:3] (GenBank® Data Bank Accession Number M73260, which is encoded by the sequence of SEQ ID NO:4), or the Ad7 hexon protein (GenBank® Data Bank Accession Number x76551). Alternately, preferably the hexon protein is the protein sequence reported by Crawford-Miksza et al. (Ad2 hexon [SEQ ID NO:56], Ad5 hexon SEQ ID NO:58]). In particular, the sequences of Crawford-Miksza et al. differ over those reported in the GenBank® Data Bank in that the amino acid residue reported as the first in the Crawford-Miksza et al. sequences is not Met, and the Ad5 hexon sequence is reported as terminating with "Gln His" instead of with "Thr Thr". As employed herein, the numbering of adenovirus hexon amino acid residues corresponds to that in Crawford-Miksza et al.

Desirably the region(s) of the deletion comprises an internal hexon protein sequence ("internal" meaning not at or near the C- or N-terminus of the protein; "near" referring to a distance of 500 amino acids or less ), preferably a hypervariable region, e.g., as reported in Crawford-Miksza et al. In particular, optimally, the internal region of the wild-type hexon protein that is deleted to generate the chimeric hexon protein comprises the entirety of l1 loop, preferably from about residue 131 to about residue 331 of the Ad2 hexon protein [SEQ ID NO:6] (which is encoded by the sequence of SEQ ID NO:5), or the corresponding region from another adenoviral serotype, e.g., particularly the corresponding region from Ad1, Ad5 [SEQ ID NO:81 (which is encoded by the sequence of SEQ ID NO:7), Ad6, Ad7, Ad8, Ad12, Ad16, Ad40, Ad41, Ad48, BAV3, or MAV1, especially as reported in Crawford-Miksza et al., supra.

Alternately, preferably the internal region of the wild-type hexon protein that is deleted to produce the chimeric hexon protein comprises one or more regions (e.g., smaller regions) of the l1 loop. Optimally the region deleted comprises a hypervariable region. Desirably the one or more regions of the l1 loop deleted are regions (i.e., hypervariable regions) selected from this group consisting of the HVR1 region, the HVR2 region, the HVR3 region, the HVR4 region, the HVR5 region, and the HVR6 region. Moreover, preferably the region of the wild-type protein that is deleted (or otherwise manipulated as described herein) occurs on the external surface of the hexon protein. Thus, HVR2, HVR3, HVR4, and HVR5—each of which are externally located regions of the hexon protein—are particularly preferred for deletion or modification.

The "HVR1 region" preferably comprises from about amino acid 137 to about amino acid 188 of the Ad2 hexon protein [SEQ ID NO:10] (which is encoded by the sequence of SEQ ID NO:9), or the corresponding region from another adenoviral serotype, e.g., particularly the corresponding region from Ad1, Ad3, Ads [SEQ ID NO:12] (which is encoded by the sequence of SEQ ID NO:11), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The "HVR2 region" preferably comprises from about amino acid 194 to about amino acid 204 of the Ad2 hexon protein [SEQ ID NO:14] (which is encoded by the sequence of SEQ ID NO:13), or the corresponding region from another adenoviral serotype, e.g., particularly the corresponding region from Ad1, Ad3, Ad5 [SEQ ID NO:16] (which is encoded by the sequence of SEQ ID NO:15), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The "HVR3 region" preferably comprises from about amino acid 222 to about amino acid 229 of the Ad2 hexon protein [SEQ ID NO:18] (which is encoded by the sequence of SEQ ID NO:17), or the corresponding region from another adenoviral serotype, e.g., particularly the corresponding region from Ad1, Ad3, Ad5 [SEQ ID NO:20] (which is encoded by the sequence of SEQ ID NO:19), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The "HVR4 region" preferably comprises from about amino acid 258 to about amino acid 271 of the Ad2 hexon protein [SEQ ID NO:22] (which is encoded by the sequence of SEQ ID NO:21), or the corresponding region from another adenoviral serotype, e.g., particularly the corresponding region from Ad1, Ad3, Ad5 [SEQ ID NO:24] (which is encoded by the sequence of SEQ ID NO:23), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The "HVR5 region" preferably comprises from about amino acid 278 to about amino acid 294 of the Ad2 hexon protein [SEQ ID NO:26] (which is encoded by the sequence of SEQ ID NO:25), or the corresponding region from another adenoviral serotype, e.g., particularly the corresponding region from Ad1, Ad3, Ad5 [SEQ ID NO:28] (which is encoded by the sequence of SEQ ID NO:27), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra. In particular, preferably the deleted region comprises from about amino acid 297 to about amino acid 304 just outside of the HVR5 region of the Ad2 hexon protein [SEQ ID NO:30] (which is encoded by the sequence of SEQ ID NO:29), or the corresponding region from another adenoviral serotype, e.g., particularly the corresponding region from Ad1, Ad3, Ad5 [SEQ ID NO:32] (which is encoded by the sequence of SEQ ID NO:31), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The "HVR6 region" preferably comprises from about amino acid 316 to about amino acid 327 of the Ad2 hexon protein [SEQ ID NO:34] (which is encoded by the sequence of SEQ ID NO:33), or the corresponding region from another adenoviral serotype, e.g., particularly the corresponding region from Ad1, Ad3, Ad5 [SEQ ID NO:36] (which is encoded by the sequence of SEQ ID NO:35), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

In another preferred embodiment of the invention, the internal region of the wild-type hexon protein that is deleted to generate the chimeric hexon protein comprises the entirety of the l2 loop, preferably from about residue 423 to about residue 477 of the Ad2 hexon protein [SEQ ID NO:38] (which is encoded by the sequence of SEQ ID NO:37), or the corresponding region from another adenoviral serotype, e.g., particularly the corresponding region from Ad1, Ad3, Ad5 [SEQ ID NO:40] (which is encoded by the sequence of SEQ ID NO:39), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra. Alternately, preferably the internal region of the wild-type hexon protein that is deleted to produce the chimeric hexon protein comprises one or more smaller regions (e.g., hypervariable regions) of the l2 loop. In particular, preferably the smaller region of the l2 loop comprises the HVR7 region.

The "HVR7 region" preferably comprises from about amino acid 433 to about amino acid 465 of the Ad2 hexon protein [SEQ ID NO:42] (which is encoded by the sequence of SEQ ID NO:41), or the corresponding region from another adenoviral serotype, e.g., particularly the corresponding region from Ad1, Ad3, Ad5 [SEQ ID NO:44] (which is encoded by the sequence of SEQ ID NO:43), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra. In particular, preferably the deleted region comprises from about amino acid 460 to about amino acid 466 of the HVR7 region (i.e., extending one base pair outside of this region) of the Ad2 hexon protein [SEQ ID NO:46] (which is encoded by the sequence of SEQ ID NO:45), or the corresponding region from another adenoviral serotype, e.g., particularly the corresponding region from Ad1, Ad3, Ad5 [SEQ ID NO:48] (which is encoded by the sequence of SEQ ID NO:47), Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

Along the same lines, the chimeric adenovirus hexon protein desirably comprises deletions in one or both of the aforementioned regions, i.e., the hexon protein comprises deletions in one or both of the l1 and l2 loops, which deletions can constitute the entirety of the loop(s), or can comprise deletions of one or more smaller regions (e.g., hypervariable regions) in one or both of the hexon loops. In particular, desirably the deleted region(s) are selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48, and equivalents and conservative variations of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:32, SEQ ID NO:38, SEQ ID NO:40, SEQ ID NO:42, SEQ ID NO:44, SEQ ID NO:46, and SEQ ID NO:48.

An "equivalent" is a naturally occurring variation of an amino acid or nucleic acid sequence, e.g., as are observed among different strains of adenovirus. A conservative variation is a variation of an amino acid sequence that results in one or more conservative amino acid substitution(s). A "conservative amino acid substitution" is an amino acid substituted by an alternative amino acid of similar charge density, hydrophilicity/hydrophobicity, size, and/or configuration (e.g., basic, Arg and Lys; aliphatic Ala, Cys, Gly, Ile, Leu, Met and Val; aromatic, Phe, Tyr, Trp, and His; hydrophilic, Glu, Gln, Asn, and Asp; hydroxyl, Ser and Thr). In another preferred embodiment, the nonnative amino acid sequence of the chimeric adenoviral coat protein (i.e., particularly a chimeric adenoviral fiber or hexon protein) comprises a deletion of one or more region(s) of the wild-type adenovirus coat protein (particularly the l1 and/or l2 loops, and, most particularly, the HVR1, HVR2, HVR3, HVR4, HVR5, HVR6, and/or HVR7 regions of the wild-type adenovirus hexon protein) as previously described, and further comprises a replacement of the region(s) with a spacer region preferably of from 1 to about 750 amino acids, especially of from about 1 to about 500 amino acids, and particularly of from about 1 to about 300 amino acids. It also is desirable that the region deleted and replaced comprises a smaller region less than about 200 amino acids, preferably less than about 100 amino acids, and optimally less than about 50 amino acids. The chimeric coat protein also desirably comprises a plurality of such replacements. Thus, according to the invention, the chimeric adenovirus coat protein comprises modification of one or more amino acids, and such modification is made in one or more regions which can be a smaller region. A spacer region of the aforementioned size also preferably simply can be inserted into one of the aforementioned regions (particularly into the l1 and/or l2 loop, or one or more of the aforementioned HVR1, HVR2, HVR3, HVR4, HVR5, HVR6, and HVR7 regions of the adenovirus hexon protein) in the absence of any deletion to render the resultant chimeric protein nonimmunogenic by, for instance, destroying the ability of a neutralizing antibody to interact with that particular site (e.g., by changing the spatial juxtaposition of critical amino acids with which the antibody interacts).

Optimally the spacer region comprises a nonconservative variation of the amino acid sequence of wild-type adenovirus coat protein (particularly wild-type adenovirus hexon protein) that comprises an epitope for a neutralizing antibody, and which may or may not be deleted upon the insertion of the spacer region. A "nonconservative variation" is a variation of this amino acid sequence that does not result in the creation or recreation in the chimeric adenovirus coat protein of the epitope for a neutralizing antibody directed against the wild-type adenovirus coat protein, and, in particular, is a variation of the spacer region that results in one or more nonconservative amino acid insertion(s) or substitution(s) in this region. A "nonconservative amino acid substitution" is an amino acid substituted by an alternative amino acid of differing charge density, hydrophilicity/hydrophobicity, size, and/or configuration (e.g., a change of a basic amino acid for an acidic amino acid, a hydrophilic amino acid for a hydrophobic amino acid, and the like).

Desirably the spacer region does not interfere with the functionality of the chimeric adenovirus coat protein, particularly the chimeric adenovirus hexon or fiber protein, e.g., the ability of hexon protein to bind penton base protein or other hexon capsomeres, or the ability of penton fiber to bind penton base and/or to a cell surface receptor. Such functionality can be assessed by virus viability. Similarly, the absence of the creation or recreation of the epitope(s) for a neutralizing antibody directed against the wild-type coat (e.g., hexon and/or fiber) protein can be confirmed using techniques as described in the Examples which follow (e.g., by ensuring the antibody, which may be in a carrier fluid such as serum or other liquid, binds the wild-type adenovirus coat protein, but not the chimeric adenovirus coat protein).

Preferably the spacer region incorporated into the adenovirus coat protein (i.e., either as an insertion into the wild-type coat protein, or to replace one or more deleted region(s) of the wild-type adenovirus coat protein) comprise a series of polar and/or charged amino acids (e.g., Lys, Arg, His, Glu, Asp, and the like), or amino acids with intermediate polarity (e.g., Gln, Asn, Thr, Ser, Met, and the like). In particular, desirably the spacer region comprises the sequence of SEQ ID NO:50 (which is encoded by the sequence of SEQ ID NO:49), and equivalents and conservative variations of SEQ ID NO:50. Alternately, the spacer region can comprise any other sequence like the FLAG octapeptide sequence of SEQ ID NO:50 that will not interfere with the functionality of the resultant chimeric protein.

In still yet another preferred embodiment, a region of a wild-type adenovirus coat protein (particularly an adenovirus hexon and/or fiber protein) is deleted and replaced with a spacer region comprising the corresponding coat protein region of another adenoviral serotype. Preferably in this embodiment the spacer region is of a different adenoviral group. For instance, preferably a region of an Ad2 coat protein can be replaced with the corresponding region of an Ad5 or Ad7 coat protein (or any other serotype of adenovirus as described above), and vice versa. It also is preferable that such a spacer region comprising the coat protein region of another adenoviral serotype is simply inserted into the corresponding coat protein region of the chimeric coat protein. In this case, the likelihood of obtaining a chimeric hexon protein that is functional can be increased by making sure that the size of the hypervariable domain resulting from such insertion approximates the size of a known hypervariable domain. For instance, the HVR1 region of Ad40 is about 30 amino acids smaller than the HVR1 region of Ad2 (as well as other adenoviruses such as Ad5, Ad8, etc.). Thus, preferably a spacer region of about 30 amino acids can be incorporated into the Ad40 HVR1 region to produce a chimeric adenovirus hexon protein. In particular, desirably the region of Ad2 (or other adenovirus) that is not present in Ad40 (i.e., approximately amino acid residues 138 to 174), or a portion thereof, is introduced into Ad40 to produce the chimeric adenoviral hexon protein.

According to the invention, desirably the nonnative amino acid sequence of a chimeric coat protein comprises a plurality of such replacements or insertions. When the coat protein is incorporated into an adenoviral vector, preferably the entire coat protein of one adenoviral serotype can be substituted with the entire coat protein of another adenoviral serotype, as described further herein.

The region or regions of wild-type adenovirus hexon protein that are deleted and replaced by the spacer region, or into which the spacer region is inserted, can be any suitable region(s) and desirably comprise one or more of the regions described above with respect to the hexon protein deletions. For instance, preferably the one or more regions into which the spacer region is inserted or which the spacer region replaces comprises the entirety of the l1 and/or l2 loop, or a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48, and equivalents and conservative variations of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48.

Similarly, the spacer region itself (i.e., both for insertion as well as replacement) preferably comprises the entirety of the l1 and/or l2 loop, or a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48, and equivalents and conservative variations of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48.

The fiber protein also preferably is altered in a similar fashion as described for modification of hexon protein to escape antibodies directed in particular against wild-type adenovirus fiber protein. Fiber protein sequences and methods of modifying fiber protein are known to those skilled in the art (see, e.g., Xia et al., supra; Novelli et al., *Virology*, 185, 365–376 (1991)). The fiber manipulations can be carried out in the absence of, or along with, modifications to the adenovirus hexon protein. In particular, preferably the fiber protein can be replaced in its entirety, or in part, with sequences of a fiber protein from a different serotype of adenovirus. Also, preferably, deletions can be made of fiber sites that constitute an epitope for a neutralizing antibody, and/or insertions can be made at the site to destroy the ability of the protein to interact with the antibody.

Nucleic Acid Encoding The Chimeric Adenovirus Coat Protein

Preferably the chimeric adenovirus coat protein (particularly the chimeric adenovirus hexon or fiber protein) comprises a nonnative amino acid sequence wherein the alteration is made at the level of DNA. Thus, the invention preferably provides an isolated and purified nucleic acid encoding a chimeric adenovirus coat protein. Desirably, the invention provides an isolated and purified nucleic acid encoding a chimeric adenovirus hexon protein as defined herein, wherein the nucleic acid sequence comprises a deletion of a region (or a plurality of such deletions) that encodes from about 1 to about 750 amino acids of the wild-type adenovirus coat protein, preferably from about 1 to about 500 amino acids, and optimally from about 1 to about 300 amino acids. It also is desirable that the region deleted comprises a smaller region that encodes less than about 200 amino acids, preferably less than about 100 amino acids, and optimally less than about 50 amino acids. In particular, optimally the deletion (e.g., of an adenoviral hexon protein) comprises the entirety of the l1 and/or l2 loop, or a sequence selected from the group consisting of SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, and SEQ ID NO:47, or a sequence comprising the corresponding region from Ad1, Ad3, Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

The invention also preferably provides an isolated and purified nucleic acid encoding a chimeric adenovirus hexon protein as defined herein, wherein the nucleic acid sequence comprises a deletion of one or more sequences selected from the group consisting of equivalents and conservatively modified variants of sequences that encode the entirety of the l1 and/or l2 loop, or SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, and SEQ ID NO:47, or a sequence comprising the corresponding region from Ad1, Ad3, Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra.

With respect to the nucleic acid sequence, an "equivalent" is a variation on the nucleic acid sequence such as can occur in different strains of adenovirus, and which either does or does not result in a variation at the amino acid level. Failure to result in variation at the amino acid level can be due, for instance, to degeneracy in the triplet code. A "conservatively modified variant" is a variation on the nucleic acid sequence that results in one or more conservative amino acid substitutions. In comparison, a "nonconservatively modified variant" is a variation on the nucleic acid sequence that results in one or more nonconservative amino acid substitutions.

In another preferred embodiment, the invention provides an isolated and purified nucleic acid encoding a chimeric adenovirus coat protein wherein the nucleic acid sequence further comprises a replacement of the deleted region (or a plurality of such replacements) with a spacer nucleic acid region (i.e., the nucleic acid sequence that encodes the aforementioned "spacer region") that encodes from about 1 to about 750 amino acids of the wild-type adenovirus coat protein, preferably from about 1 to about 500 amino acids, and optimally from about 1 to about 300 amino acids. It also is desirable that the region deleted and replaced comprises a smaller region that encodes less than about 200 amino acids, preferably less than about 100 amino acids, and optimally less than about 50 amino acids.

Preferably, the spacer nucleic acid region comprises a FLAG octaptide-encoding sequence [SEQ ID NO:49], and equivalents and conservatively modified variants of SEQ ID NO:49. Similarly, a spacer nucleic acid region can be employed that substitutes one or more coat protein encoding regions (particularly a hexon protein encoding region) of a particular adenoviral serotype with a coat protein encoding region (particularly a hexon protein encoding region) of another adenoviral serotype. Thus, preferably a spacer nucleic acid region present in a chimeric adenoviral hexon protein is selected from the group consisting of sequences that encode the entirety of the l1 and/or l2 loop, or SEQ ID NO: 5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, and SEQ ID NO:47, or a sequence comprising the corresponding region from Ad1, Ad3, Ad6, Ad7, Ad8, Ad11, Ad12, Ad14, Ad16, Ad21, Ad34, Ad35, Ad40, Ad41, Ad48, BAV3, or MAV1, especially as reported in Crawford-Miksza et al., supra, and equivalents and conservatively modified variants of these sequences.

As described above with respect to the chimeric adenovirus coat protein, the spacer nucleic acid region (or a plurality thereof) simply can be incorporated into the coat protein in the absence of any deletions. These manipulations can be carried out so as to produce the above-described chimeric adenovirus coat protein.

The means of making such a chimeric adenoviral coat protein (i.e., by introducing conservative or nonconservative variations at either the level of DNA or protein) are known in the art, are described in the Examples which follow, and also can be accomplished by means of various commercially available kits and vectors (e.g., New England Biolabs, Inc., Beverly, Me.; Clontech, Palo Alto, Calif.; Stratagene, LaJolla, Calif., and the like). In particular, the ExSite™ PCR-based site-directed mutagenesis kit and the Chameleona double-stranded site-directed mutagenesis kit by Stratagene can be employed for introducing such mutations. Moreover, the means of assessing such mutations (e.g., in terms of effect on ability not to be neutralized by antibodies directed against wild-type hexon protein) are described in the Examples herein.

Accordingly, the present invention provides a preferred means of making a chimeric adenoviral coat protein, particularly a chimeric adenoviral hexon protein, which comprises obtaining an adenoviral genome encoding the wild-type adenovirus coat protein (e.g., the wild-type adenovirus hexon protein), and deleting one or more region(s) of the chimeric adenovirus coat protein (particularly the chimeric adenovirus hexon protein) comprising from about 1 to about 750 amino acids by modifying the corresponding nucleic acid coding sequence. Similarly, the invention provides a method of making a chimeric adenovirus coat protein (particularly a chimeric adenovirus hexon protein) which comprises obtaining an adenoviral genome encoding the wild-type adenovirus coat protein, deleting one or more region(s) of the adenovirus coat protein comprising from about 1 to about 750 amino acids by modifying the corresponding coding sequence, and replacing the deleted region(s) with a spacer region comprising from about 1 to about 300 amino acids by introducing a nucleic acid region (i.e., a "spacer nucleic acid region") that codes for same. Alternately, the spacer region preferably is simply incorporated into the coat protein (particularly the hexon protein) in the absence of any deletion. Optimally the spacer nucleic acid region encodes a nonconservative variation of the amino acid sequence of the wild-type adenovirus coat protein. The size of the DNA used to replace the native coat protein coding sequence may be constrained, for example, by impeded folding of the coat protein or improper assembly of the coat protein into a complex (e.g., penton base/hexon complex) or virion. DNA encoding 150 amino acids or less is particularly preferred for insertion/replacement in the chimeric coat protein gene sequence, and DNA encoding 50 amino acids or less is even more preferred.

Briefly, the method of mutagenesis comprises deleting one or more regions of an adenovirus coat protein, and/or inserting into an adenovirus coat protein one or more regions with a differing amino acid sequence, particularly by manipulating the DNA sequence. Several methods are available for carrying out such manipulations of adenovirus coat protein DNA sequences; these methods further can be used in combination. The method of choice depends on factors known to those skilled in the art, e.g., the size of the DNA region to be manipulated. For instance, convenient restriction sites (which further can be introduced into a sequence) can be used to introduce or remove segments of DNA, or entire genes or coding sequences. Alternately, other methods of mutagenesis involve the hybridization of a mismatched oligonucleotide to a region of single-stranded target DNA, extending the primer, for instance, using T7 DNA polymerase or other such means to produce a double-stranded heteroduplex, and isolating the mutant strand that incorporates the mismatched oligonucleotide from the parental nonmutant strand for use as a template and in further manipulations. The mutant strand can be separated from the parental strand using various selection means known to those skilled in the art (see, e.g., Kunkel et al., *Methods Enzymol.,* 204, 125–139 (1991), as well as the underlying methodology employed in the Chameleon™ kit). Alternately, the parental strand can be selectively degraded, for instance, with use of enzymes that nick the nonmethylated strand of a hemi-methylated DNA molecule (e.g., HpaII, MspI, and Sau3AI), and by extending the mutant strand using 5-methyl-dCTP, which renders the strand resistant to cleavage by these enzymes. Along the same lines, an entirely PCR-based approach can be employed for making mutations (e.g., Kunkel, *Proc. Natl. Acad. Sci.,* 82, 488–492 (1985); Costa et al., *Nucleic Acids Res.,* 22, 2423 (1994)), for instance, such as the approach encompassed by the ExSite™ kit. More generally, amino acid substitutions or deletions can be introduced during PCR by incorporating appropriate mismatches in one or both primers. Once the chimeric coat protein sequence has been produced, the nucleic acid fragment encoding the sequence further can be isolated, e.g., by PCR amplification using 5' and 3' primers, or through use of convenient restriction sites.

Vector Comprising a Chimeric Hexon Protein

A "vector" according to the invention is a vehicle for gene transfer as that term is understood by those skilled in the art, and includes viruses, plasmids, and the like. A preferred vector is an adenovirus, particularly a virus of the family Adenoviridae, and desirably of the genus Mastadenovirus (e.g., comprised of mammalian adenoviruses) or Aviadenovirus (e.g., comprised of avian adenoviruses). Such an adenovirus (or other viral vector) can be transferred by its own means of effecting cell entry (e.g., by receptor-mediated endocytosis), or can be transferred to a cell like a plasmid, i.e., in the form of its nucleic acid, for instance, by using liposomes to transfer the nucleic acid, or by microinjecting or transforming the DNA into the cell. The nucleic acid vectors that can be employed for gene transfer, particularly the adenoviral nucleic acid vectors, are referred to herein as "transfer vectors". Such nucleic acid vectors also include intermediary plasmid vectors that are employed, e.g., in the construction of adenoviral vectors.

Desirably an adenoviral vector is a serotype group C virus, preferably an Ad2 or Ad5 vector, although any other serotype adenoviral vector (e.g., group A including serotypes 12 and 31, group B including serotypes 3 and 7, group D including serotypes 8 and 30, group E including serotype 4, and group F including serotypes 40 and 41, and other Ad vectors previously described) can be employed. An adenoviral vector employed for gene transfer can be replication competent. Alternately, an adenoviral vector can comprise genetic material with at least one modification therein, which renders the virus replication deficient. The modification to the adenoviral genome can include, but is not limited to, addition of a DNA segment, rearrangement of a DNA segment, deletion of a DNA segment, replacement of a DNA segment, or introduction of a DNA lesion. A DNA segment can be as small as one nucleotide and as large as 36 kilobase pairs (i.e., the approximate size of the adenoviral genome) or, alternately, can equal the maximum amount which can be packaged into an adenoviral virion (i.e., about 38 kb). Preferred modifications to the group C adenoviral genome include modifications in the E1, E2, E3 and/or E4 regions. Similarly, an adenoviral vector can be a cointegrate, i.e., a ligation of adenoviral sequences with other sequences, such as other virus sequences, particularly baculovirus sequences, or plasmid sequences, e.g., so as to comprise a prokaryotic or eukaryotic expression vector.

In terms of an adenoviral vector (particularly a replication deficient adenoviral vector), such a vector can comprise either complete capsids (i.e., including a viral genome such as an adenoviral genome) or empty capsids (i.e., in which a viral genome is lacking, or is degraded, e.g., by physical or chemical means). The capsid further can comprise nucleic acid linked to the surface by means known in the art (e.g., Curiel et al., *Human Gene Therapy*, 3, 147–154 (1992)) or can transfer non-linked nucleic acid, for instance, by adenoviral-mediated uptake of bystander nucleic acid (e.g., PCT International Application WO 95/21259).

Along the same lines, since methods are available for transferring an adenovirus in the form of its nucleic acid sequence (i.e., DNA), a vector (i.e., a transfer vector) similarly can comprise DNA, in the absence of any associated protein such as capsid protein, and in the absence of any envelope lipid. Inasmuch as techniques are available for making a RNA copy of DNA (e.g., in vitro transcription), and inasmuch as RNA viruses also can be employed as vectors or transfer vectors, a transfer vector also can comprise RNA. Thus, according to the invention whereas a vector comprises (and, further, may encode) a chimeric adenoviral coat protein, a transfer vector typically encodes a chimeric adenoviral coat protein (particularly a chimeric adenoviral hexon and/or fiber protein).

Based on this, the invention provides an adenoviral vector that comprises a chimeric coat protein (particularly a chimeric hexon and/or fiber protein) according to the invention. Preferably such a vector comprises a chimeric coat protein (particularly a chimeric adenovirus hexon protein and/or chimeric adenovirus fiber protein) as described above. Alternately, preferably the vector lacks wild-type fiber protein, e.g., the vector encodes a truncated or non-functional fiber protein, or fails to translate fiber protein. Such fiber mutations and the means of introducing fiber mutations are known to those skilled in the art (see, e.g., Falgout et al., *J. Virol.*, 62, 622–625 (1988)).

Of course, the chimeric adenoviral coat proteins include coat proteins in which the native (i.e., wild-type) hexon and/or fiber protein of an adenoviral vector is replaced by a hexon and or fiber amino acid sequence of a different adenoviral serotype such that the resultant adenoviral vector has a decreased ability or inability to be recognized by neutralizing antibodies directed against the corresponding wild-type coat protein. This replacement can comprise the entirety of the hexon and/or fiber amino acid sequence, or only a portion, as described above. Both proteins can be manipulated (e.g., in a single adenovirus), or only a single chimeric adenovirus coat protein can be employed, with the remaining coat proteins being wild-type.

A vector according to the invention (including a transfer vector) preferably comprises additional sequences and mutations, e.g., some that can occur within the coat protein coding sequence itself. In particular, a vector according to the invention further preferably comprises a nucleic acid encoding a passenger gene or passenger coding sequence. A "nucleic acid" is a polynucleotide (i.e., DNA or RNA). A "gene" is any nucleic acid sequence coding for a protein or an RNA molecule. Whereas a gene comprises coding sequences plus any non-coding sequences, a "coding sequence" does not include any non-coding (e.g., regulatory) DNA. A "passenger gene" or "passenger coding sequence" is any gene which is not typically present in and is subcloned into a vector (e.g., a transfer vector) according to the present invention, and which upon introduction into a host cell is accompanied by a discernible change in the intracellular environment (e.g., by an increased level of deoxyribonucleic acid (DNA), ribonucleic acid (RNA), peptide or protein, or by an altered rate of production or degradation thereof). A "gene product" is either an as yet untranslated RNA molecule transcribed from a given gene or coding sequence (e.g., mRNA or antisense RNA) or the polypeptide chain (i.e., protein or peptide) translated from the mRNA molecule transcribed from the given gene or coding sequence. A gene or coding sequence is "recombinant" if the sequence of bases along the molecule has been altered from the sequence in which the gene or coding sequence is typically found in nature, or if the sequence of bases is not typically found in nature. According to this invention, a gene or coding sequence can be naturally occurring or wholly or partially synthetically made, can comprise genomic or complementary DNA (cDNA) sequences, and can be provided in the form of either DNA or RNA.

Non-coding sequences or regulatory sequences include promoter sequences. A "promoter" is a DNA sequence that directs the binding of RNA polymerase and thereby promotes RNA synthesis. "Enhancers" are cis-acting elements of DNA that stimulate or inhibit transcription of adjacent genes. An enhancer that inhibits transcription is also termed a "silencer". Enhancers differ from DNA-binding sites for sequence-specific DNA binding proteins found only in the promoter (which also are termed "promoter elements") in that enhancers can function in either orientation, and over distances of up to several kilobase pairs, even from a position downstream of a transcribed region. According to the invention, a coding sequence is "operably linked" to a promoter (e.g., when both the coding sequence and the promoter constitute a passenger gene) when the promoter is capable of directing transcription of that coding sequence.

Accordingly, a "passenger gene" can be any gene, and desirably either is a therapeutic gene or a reporter gene. Preferably a passenger gene is capable of being expressed in a cell in which the vector has been internalized. For instance, the passenger gene can comprise a reporter gene, or a nucleic acid sequence which encodes a protein that can be detected in a cell in some fashion. The passenger gene also can comprise a therapeutic gene, for instance, a therapeutic gene which exerts its effect at the level of RNA or protein. Similarly, a protein encoded by a transferred therapeutic gene can be employed in the treatment of an inherited disease, such as, e.g., the cystic fibrosis transmembrane conductance regulator cDNA for the treatment of cystic fibrosis. The protein encoded by the therapeutic gene can exert its therapeutic effect by resulting in cell killing. For instance, expression of the gene in itself may lead to cell killing, as with expression of the diphtheria toxin A gene, or the expression of the gene may render cells selectively sensitive to the killing action of certain drugs, e.g., expression of the HSV thymidine kinase gene renders cells sensitive to antiviral compounds including acyclovir, gancyclovir and FIAU (1-(2-deoxy-2-fluoro-b-D-arabinofuranosil)-5-iodouracil). Moreover, the therapeutic gene can exert its effect at the level of RNA, for instance, by encoding an antisense message or ribozyme, by affecting splicing or 3' processing (e.g., polyadenylation), or by encoding a protein which acts by affecting the level of expression of another gene within the cell (i.e., where gene expression is broadly considered to include all steps from initiation of transcription through production of a processed protein), perhaps, among other things, by mediating an altered rate of mRNA accumulation, an alteration of mRNA transport, and/or a change in post-transcriptional regulation. Accordingly, the use of the term "therapeutic gene" is intended to encompass these and any other embodiments of that which is more commonly referred to as gene therapy and is known to those of skill in the art. Similarly, the recombinant adenovirus can be used for gene therapy or to study the effects of expression of the gene (e.g., a reporter gene) in a given cell or tissue in vitro or in vivo, or for diagnostic purposes.

Also, a passenger coding sequence can be employed in the vector. Such a coding sequence can be employed for a variety of purposes even though a functional gene product may not be translated from the vector sequence. For instance, the coding sequence can be used as a substrate for a recombination reaction, e.g., to recombine the sequence with the host cell genome or a vector resident in the cell. The coding sequence also can be an "anticoding sequence," e.g., as appropriate for antisense approaches. Other means of using the coding sequence will be known to one skilled in the art.

The present invention thus provides recombinant adenoviruses comprising a chimeric hexon protein and/or a chimeric fiber protein, and which preferably additionally comprise a passenger gene or genes capable of being expressed in a particular cell. The recombinant adenoviruses can be generated by use of a vector, specifically, a transfer vector, and preferably a viral (especially an adenoviral) or plasmid transfer vector, in accordance with the present invention. Such a transfer vector preferably comprises a chimeric adenoviral hexon and/or fiber gene sequence as previously described.

Similarly, the means of constructing such a transfer vector are known to those skilled in the art. For instance, a chimeric adenovirus coat protein gene sequence can simply be ligated into the vector using convenient restriction sites. Alternately, a wild-type adenovirus gene sequence can be mutagenized to create the chimeric coat protein sequence following its subcloning into a vector. Similarly, a chimeric coat protein gene sequence can be moved via standard molecular genetic techniques from a transfer vector into baculovirus or a suitable prokaryotic or eukaryotic expression vector (e.g., a viral or plasmid vector) for expression and evaluation of penton base binding, and other biochemical characteristics.

Accordingly, the present invention also provides recombinant baculoviral and prokaryotic and eukaryotic expression vectors comprising an aforementioned chimeric adenoviral coat protein gene sequence, which, along with the nucleic acid form of the adenoviral vector (i.e., an adenoviral transfer vector) are "transfer vectors" as defined herein. By moving the chimeric gene from an adenoviral vector to baculovirus or a prokaryotic or eukaryotic expression vector, high protein expression is achievable (approximately 5–50% of the total protein being the chimeric protein).

Similarly, adenoviral vectors (e.g., virions or virus particles) are produced using transfer vectors. For instance, an adenoviral vector comprising a chimeric coat protein according to the invention can be constructed by introducing into a cell, e.g., a 293 cell, a vector comprising sequences from the adenoviral left arm, and a vector comprising sequences from the adenoviral right arm, wherein there is a region of overlap between the sequences. As described in the Examples which follow, this methodology results in recombination between the sequences, generating a vector that comprises a portion of each of the vectors, particularly the region comprising the chimeric coat protein sequences.

The present invention thus preferably also provides a method of constructing an adenoviral vector that has a decreased ability or inability to be recognized by a neutralizing antibody directed against wild-type adenovirus hexon protein and/or fiber protein. This method comprises replacing a coat protein of the vector (i.e., a wild-type adenovirus hexon and/or fiber protein) with the corresponding chimeric adenovirus coat protein according to the invention to produce a recombinant adenoviral vector.

The coat protein chimera-containing particles are produced in standard cell lines, e.g., those currently used for adenoviral vectors. Deletion mutants lacking the fiber gene, or possessing shortened versions of the fiber protein, similarly can be employed in vector construction, e.g., H2dl802, H2dl807, H2dl1021 (Falgout et al., supra), as can other fiber mutants. The fiberless particles have been shown to be stable and capable of binding and infecting cells (Falgout et al., supra).

Illustrative Uses and Benefits

The present invention provides a chimeric coat protein that has a decreased ability or inability to be recognized by a neutralizing antibody directed against the corresponding wild-type coat protein, as well as vectors (including transfer vectors) comprising same. The chimeric coat protein (such as a chimeric hexon and/or fiber protein) has multiple uses, e.g., as a tool for studies in vitro of capsid structure and assembly, and capsomere binding to other proteins.

A vector (e.g., a transfer vector) comprising a chimeric coat protein can be used in strain generation, for instance, in generation of recombinant strains of adenovirus. Similarly, such a vector, particularly an adenoviral vector, can be used in gene therapy. Specifically, a vector of the present invention can be used to treat any one of a number of diseases by delivering to targeted cells corrective DNA, i.e., DNA encoding a function that is either absent or impaired, or a discrete killing agent, e.g., DNA encoding a cytotoxin that, for instance, is active only intracellularly. Diseases that are candidates for such treatment include, but are not limited to, cancer, e.g., melanoma, glioma or lung cancers; genetic disorders, e.g., cystic fibrosis, hemophilia or muscular dystrophy; pathogenic infections, e.g., human immunodeficiency virus, tuberculosis or hepatitis; heart disease, e.g., preventing restenosis following angioplasty or promoting angiogenesis to reperfuse necrotic tissue; and autoimmune disorders, e.g., Crohn's disease, colitis or rheumatoid arthritis. In particular, gene therapy can be carried out in the treatment of diseases, disorders, or conditions that require repeat administration of the corrective DNA and/or the adenoviral vector, and thus for which current adenoviral-mediated approaches to gene therapy are less than optimal.

Moreover, such a vector, particularly an adenoviral vector, can be used to deliver material to a cell not as a method of gene therapy, but for diagnostic or research purposes. In particular, a vector comprising a chimeric adenovirus coat protein according to the invention can be employed to deliver a gene either in vitro or in vivo, for research and/or diagnostic purposes.

For instance, instead of transferring a so-called therapeutic gene, a reporter gene or some type of marker gene can be transferred instead. Marker genes and reporter genes are of use, for instance, in cell differentiation and cell fate studies, as well as potentially for diagnostic purposes. Moreover, a standard reporter gene such as a β-galactosidase reporter gene, a gene encoding green fluorescent protein (GFP), or a β-glucuronidase gene can be used in vivo, e.g., as a means of assay in a living host, or, for instance, as a means of targeted cell ablation (see, e.g., Minden et al., *Biotechniques*, 20, 122–129 (1996); Youvan, *Science*, 268, 264 (1995); U.S. Pat. No. 5,432,081; Deonarain et al., *Br. J. Cancer*, 70, 786–794 (1994)).

Similarly, it may be desirable to transfer a gene to use a host essentially as a means of production in vivo of a particular protein. Along these lines, transgenic animals have been employed, for instance, for the production of recombinant polypeptides in the milk of transgenic bovine species (e.g., PCT International Application WO 93/25567). The use of an adenovirus according to the invention for gene transfer conducted for protein production in vivo further is advantageous in that such use should result in a reduced (if not absent) immune response as compared with the use of a wild-type adenovirus vector. Other "non-therapeutic" reasons for gene transfer include the study of human diseases using an animal model (e.g., use of transgenic mice and other transgenic animals including p53 tumor suppressor gene knockouts for tumorigenic studies, use of a transgenic model for impaired glucose tolerance and human Alzheimer's amyloid precursor protein models for the study of glucose metabolism and for the pathogenesis of Alzheimer's disease, respectively, etc.).

Furthermore, an adenoviral vector comprising a chimeric adenovirus coat protein and employed as described above is advantageous in that it can be isolated and purified by conventional means. For instance, it is likely that special cell lines will not need to be made in order to propagate adenoviruses comprising the chimeric coat proteins.

These aforementioned illustrative uses and recitation of benefits are by no means comprehensive, and it is intended that the present invention encompass such further uses which necessarily flow from, but are not explicitly recited, in the disclosure herein.

Means of Administration

The vectors and transfer vectors of the present invention can be employed to contact cells either in vitro or in vivo. According to the invention "contacting" comprises any means by which a vector is introduced intracellularly; the method is not dependent on any particular means of introduction and is not to be so construed. Means of introduction are well known to those skilled in the art, and also are exemplified herein.

Accordingly, introduction can be effected, for instance, either in vitro (e.g., in an ex vivo type method of gene therapy or in tissue culture studies) or in vivo by methods that include, but are not limited to, electroporation, transformation, transduction, conjugation, triparental mating, (co-)transfection, (co-)infection, high velocity bombardment with DNA-coated microprojectiles, incubation with calcium phosphate-DNA precipitate, direct microinjection into single cells, and the like. Similarly, the vectors can be introduced by means of membrane fusion using cationic lipids, e.g., liposomes. Such liposomes are commercially available (e.g., Lipofectin®, Lipofectamine™, and the like, supplied by Life Technologies, Gibco BRL, Gaithersburg, Md.). Moreover, liposomes having increased transfer capacity and/or reduced toxicity in vivo (see, e.g., PCT International Application WO 95/21259 and references reviewed therein) can be employed in the present invention. Other methods also are available and are known to those skilled in the art.

According to the invention, a "host" encompasses any host into which a vector of the invention can be introduced, and thus encompasses an animal, including, but not limited to, an amphibian, bird, insect, reptile, or mammal. Optimally a host is a mammal, for instance, a rodent, primate (such as chimpanzee, monkey, ape, gorilla, orangutan, or gibbon), feline, canine, ungulate (such as ruminant or swine), as well as, in particular, a human.

Similarly, a "cell" encompasses any cell (or collection of cells) from a host into which an adenoviral vector can be introduced, e.g., preferably an epithelial cell. Any suitable organs or tissues or component cells can be targeted for vector delivery. Preferably, the organs/tissues/cells employed are of the circulatory system (e.g., heart, blood vessels or blood), respiratory system (e.g., nose, pharynx, larynx, trachea, bronchi, bronchioles, lungs), gastrointestinal system (e.g., mouth, pharynx, esophagus, stomach, intestines, salivary glands, pancreas, liver, gallbladder), urinary system (e.g., kidneys, ureters, urinary bladder, urethra), nervous system (e.g. brain and spinal cord, or special sense organs such as the eye) and integumentary system (e.g., skin). Even more preferably the cells being targeted are selected from the group consisting of heart, blood vessel, lung, liver, gallbladder, urinary bladder, and eye cells.

Thus, the present invention preferably also provides a method of genetically modifying a cell. This method preferably comprises contacting a cell with a vector comprising a chimeric adenovirus hexon protein and/or a chimeric adenovirus fiber protein, wherein desirably the vector is an adenovirus vector. The method preferably results in the production of a host cell comprising a vector according to the invention.

Moreover, the method of the invention of genetically modifying a cell can be employed in gene therapy, or for administration for diagnosis or study. The application of this method in vivo optimally comprises administering to a patient in need of gene therapy (e.g., a patient suffering from a disease, condition or disorder) a therapeutically effective amount of a recombinant adenovirus vector according to the invention. This method preferably can be employed as part of an ongoing gene therapy regimen, e.g., wherein the vector (e.g., a recombinant adenovirus vector) comprising the chimeric adenovirus coat protein is administered following (e.g., after from about 1 week to about 2 months) administration of a therapeutically effective amount of a vector comprising either the corresponding wild-type coat protein or a coat protein of a different adenoviral serotype. Alternately, the vector comprising the chimeric adenovirus coat protein can be employed as an initial attempt at gene delivery.

One skilled in the art will appreciate that suitable methods of administering a vector (particularly an adenoviral vector) of the present invention to an animal for purposes of gene therapy (see, for example, Rosenfeld et al. (1991), supra; Jaffe et al., Clin. Res., 39(2), 302A (1991); Rosenfeld et al., Clin. Res., 39(2), 311A (1991a); Berkner, supra), chemotherapy, vaccination, diagnosis, and/or further study are available. Although more than one route can be used for administration, a particular route can provide a more immediate and more effective reaction than another route. For instance, local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration. Clinical trials regarding use of gene therapy vectors in vivo are ongoing. The methodology employed for such clinical trials as well as further technologies known to those skilled in the art can be used to administer the vector of the present invention for the purpose of research, diagnosis and/or gene therapy.

Pharmaceutically acceptable excipients also are well-known to those who are skilled in the art, and are readily available. The choice of excipient will be determined in part by the particular method used to administer the recombinant vector. Accordingly, there is a wide variety of suitable formulations for use in the context of the present invention. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

A vector of the present invention (including an adenoviral vector and a transfer vector), alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, a vector of the present invention can be made into suppositories by mixing with a variety of bases such as emulsifying bases or water-soluble bases.

Formulations suitable for vaginal administration can be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene of interest, the composition employed, the method of administration, the particular site and organism undergoing administration, and the reason for the administration (e.g., gene therapy, diagnosis, means of producing a protein, further study, etc). Generally, the "effective amount" of the composition is such as to produce the desired effect in a host which can be monitored using several end-points known to those skilled in the art. For example, one desired effect might comprise effective nucleic acid transfer to a host cell. Such transfer can be monitored in terms of a therapeutic effect (e.g., alleviation of some symptom associated with the disease or syndrome being treated), or by further evidence of the transferred gene or coding sequence or its expression within the host (e.g., using the polymerase chain reaction, Northern or Southern hybridizations, or transcription assays to detect the nucleic acid in host cells, or using immunoblot analysis, antibody-mediated detection, or particularized assays to detect protein or polypeptide encoded by the transferred nucleic acid, or impacted in level or function due to such transfer). One such particularized assay described in the Examples which follow includes an assay for expression of a chloramphenicol acetyl transferase reporter gene.

Generally, to ensure effective transfer of the vectors of the present invention, it is preferable that from about 1 to about 5,000 copies of the vector be employed per cell to be contacted, based on an approximate number of cells to be contacted in view of the given route of administration. It is even more preferable that from about 1 to about 300 plaque forming units (pfu) enter each cell. However, this is just a general guideline which by no means precludes use of a higher or lower amount of a component, as might be warranted in a particular application, either in vitro or in vivo. For example, the actual dose and schedule can vary depending on whether the composition is administered in combination with other pharmaceutical compositions, or depending on interindividual differences in pharmacokinetics, drug disposition, and metabolism. Similarly, amounts can vary in in vitro applications depending on the particular cell type utilized or the means by which the vector is transferred. One skilled in the art easily can make any necessary adjustments in accordance with the necessities of the particular situation.

The following examples further illustrate the present invention and, of course, should not be construed as in any way limiting its scope.

EXAMPLE 1

This example describes experiments investigating adenoviral anti-vector neutralizing immunity.

To clarify the phenomenon of neutralizing immunity, an animal having circulating antibodies to one adenoviral vector type received intratracheal administration of another serotype adenoviral vector, and gene expression commanded by the second vector was monitored. Specifically, either an Ad4 or Ad5 wild-type vector was administered to the lungs of Sprague-Dawley rats. Ten days later, an Ad5 reporter vector was administered to the lungs of the same animals. This reporter vector, which is referred to herein as the "pure 5" vector, comprises an E1⁻ E3⁻ type 5 adenoviral vector which expresses the chloramphenicol acetyl transferase (CAT) gene driven by the cytomegalovirus early/intermediate promoter/enhancer (CMV) (i.e., AdCMV-CATgD described in Kass-Eisler et al., *Proc. Natl. Acad. Sci.*, 15, 11498–11502 (1993)).

About twenty-four hours following administration of the "pure 5" vector, CAT activity was measured in homogenized lung tissue using a CAT assay as previously described (Kass Eisler et al. (1993), supra). CAT activity was monitored at various times thereafter up to 10 days following introduction of the "pure 5" vector. CAT activity was determined relative to the "pure 5" vector administered to naive animals (i.e., expression measured under this condition was considered 100%). The results of these studies are set out in Table 1, and are further reported in Mastrangeli et al., *Human Gene Therapy*, 1, 79–87 (1996).

TABLE 1

Effect of anti-serotype 4 (group E) neutralizing antibodies on the ability of a "pure 5" adenoviral vector to transfer a CAT reporter gene to the lung

| Time (0 hours) | Time (10 days) | CAT Activity |
| --- | --- | --- |
| — | — | 0% |
| — | pure 5 | 100% |
| Ad5 | pure 5 | 0% |
| Ad4 | pure 5 | 105 ± 10% |

These results confirm that in the presence of neutralizing antibodies elicited against one adenoviral group (e.g., against group E, serotype 4), it is possible to efficiently transfer and express a gene in vivo using an adenoviral vector derived from another group (e.g., derived from group C, serotype 5). Neutralizing immunity evoked against one serotype group does not protect against infection by another group of adenovirus. These data support the paradigm of alternating adenoviral vectors derived from different subgroups as a strategy to circumvent anti-adenoviral humoral immunity.

EXAMPLE 2

The predominant epitopes that evoke neutralizing immunity are located on the fiber and hexon. Based on this, the effect of switching the fiber protein was investigated. Namely, a vector was constructed that was identical to the "pure 5" vector except that the fiber gene was switched from a serotype 5, group C fiber to a serotype 7, group B fiber. The resultant vector is referred to herein as the "5 base/7 fiber" vector.

Figure 2:
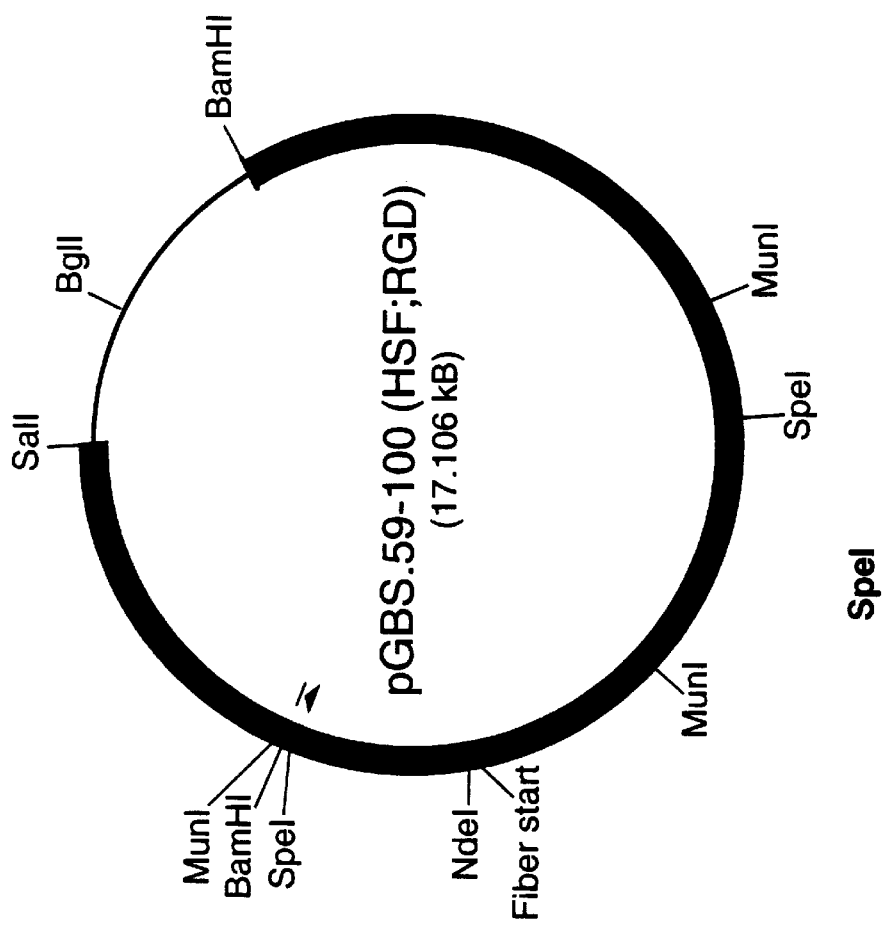
FIG. 2 is a partial restriction map of the vector pGBS.59–100(HSF:RGD).

The Ad5/Ad7 fiber construct was generated as shown in FIG. 1. An approximately 2.7 kb (Ad5 28689–31317 bp) fragment in pAd70-100 was replaced with a PacI linker (pAd70–100dlE3.Pac). A BamHI linker was inserted at a MunI site as indicated in FIG. 2 to produce pAd70–100dlE3.Pac.Bam. A PCR-amplified PacI-BamHI fragment of approximately 1.1 kb containing the Ad7 fiber gene was inserted into pAd70-100dlE3.Pac.Bam to produce pAd70-100dlE3.fiber7.

In order to assess the ability of the Ad5 virus with Ad7 fiber to infect cells in vitro and in vivo, reporter gene assays were performed. A replication-defective recombinant adenoviral reporter vector designated AdCMv-CATNeo was used in the reporter gene assay. The reporter vector consists of the adenoviral origin of replication and viral packaging sequences, a combination of strong eukaryotic promoter (cytomegalovirus or CMV-1) and splicing elements, the bacterial chloramphenicol acetyl transferase (CAT) gene sequence, the mouse $\beta^{maj}$-globin poly(A) site, the neomycin gene sequence (Neo), and sufficient adenoviral DNA to allow for overlap recombination.

The reporter vector was used to generate AdCMV-CATNeo, AdCMV-CATNeo-dlE3 (AdCMV-CATNeo+pAd70-100dlE3) and AdCMV-CATNeo-dlE3-Fiber7 (AdCMV-CATNeo+pAd70-100lE3.Fiber7) viruses. Each virus was grown in large scale, i.e., a one liter suspension of human embryonic kidney 293 cells, to yield virus at a concentration of $10^{12}$ particles/ml. A549 cells were infected with an estimated 100, 300 or 1,000 particles/cell of one of the three viruses. After 48 hours, the cells were harvested and lysates were prepared as described in Kass-Eisler et al. (1993), supra. Using 50 μl of each lysate, CAT assays were performed and acetylated chloramphenicol products were separated by thin layer chromatography using chloroform-:methanol (95:5). The results of the assays confirm that each virus was able to infect cells and express gene products at appropriate levels. Accordingly, the virus in which the native fiber was replaced with a nonnative fiber could infect cells and express genes like the parental virus.

Following this study, adult Sprague-Dawley rats were infected with 108 viral particles by direct cardiac injection as described in Kass-Eisler et al. (1993), supra. Five days later, the rats were sacrificed, cardiac lysates were prepared, and CAT assays were performed. The amount of the CAT gene product produced was compared between the dlE3 and dlE3-Fiber7 viruses. Results indicated that both viruses were able to infect cells in vivo. The replacement of the wild-type Ad5 fiber gene with that of Ad7 did not impair the ability of the virus to infect cells. Accordingly, the virus in which the native fiber was replaced with a nonnative fiber could also infect cells and express genes like the parental virus in vivo. These results support the utility of adenovirus with chimeric fiber in the context of gene therapy.

EXAMPLE 3

This example describes the effect on neutralizing immunity of switching the fiber protein of an adenovirus from one serotype to another.

The "pure 5" and "5 base/7 fiber" vectors described in the preceding Example were administered to Sprague-Dawley rats which either were naive or pre-immunized against wild-type Ads. For these experiments, wild-type Ad5 or wild-type Ad7 ($6 \times 10^9$ particles in phosphate buffered saline (PBS)) was administered intraperitoneally as a primary inoculation. Seventeen days later, serum samples were taken, and about $6 \times 10^9$ particles in about 50 μl of PBS was injected. At about 120 hours following injection the animals were sacrificed, serum and heart tissue were harvested, and heart tissue was processed for CAT assays as previously described (Kass-Eisler et al. (1993), supra). CAT assays also were performed on heart lysates of rat hearts infected with the "pure 5" vector or "5 base/7 fiber" vector alone.

Administration of either vector to naive animals resulted in comparable levels of CAT in heart tissue. In comparison, administration of either the "pure 5" vector or the "5 base/7 fiber" vector to the animals that were pre-immunized against the "pure 5" vector resulted in a reduction of CAT levels by more than two orders of magnitude as compared with mock-infected controls. These and further results are reported in Gall et al., *J. Virol.*, 70, 2116–2163 (1996).

These results confirm that switching the fiber from that of adenoviral serotype 5 group C vector to that of an adenoviral serotype 7 group B vector by itself is insufficient to allow the vector to escape neutralizing antibodies generated against an adenoviral vector comprising Ad5 fiber. These results imply that antibodies against adenoviral structures other than fiber also are important in the process of neutralizing immunity. Furthermore, whereas switching the fiber serotype to another serotype may be insufficient in and of itself to allow an adenovirus to escape immune detection, such switching when done in combination with removal of other epitopes may be desirable, for instance, to reduce an immune response.

EXAMPLE 4

This example describes the construction of adenovirus vectors wherein the neutralizing immunity-evoking epitopes have been modified. In particular, this example describes vectors comprising chimeric adenoviral hexon protein, wherein the hexon neutralizing immunity-evoking epitopes are modified.

The results of the prior example indicate that it is possible to develop vectors for repeat administration in gene therapy from non-group C adenovirus, thus circumventing pre-existing neutralizing immunity. As another strategy, the dominant neutralizing immunity-evoking epitopes on existing group C vectors can be modified to render the vectors "stealth" to the existing neutralizing immunity. For instance, adenoviral type 5-based E1⁻ E3⁻ CAT-expressing vectors can be constructed that have the same genetic composition as the "pure 5" and "5 base/7 fiber" vectors described above, except for possessing a gene encoding a chimeric hexon that is not recognized by pre-existing anti-type 5 neutralizing immunity.

To derive the vectors, the chimeric hexon gene present in the "pure 5" parental vector can be modified, in particular, l1 and/or l2 can be altered. The hexon modifications that can be made on the "pure 5" CAT vector, or other adenoviral vector (such as any other adenoviral serotype vector), include, but are not limited to: (1) hexon with l1 deleted in its entirety; (2) hexon with l2 deleted in its entirety; (3) hexon with both l1 and l2 deleted; (4) hexon with any one or more of HVR1, HVR2, HVR3, HVR4, HVR5, HVR6, or HVR7, deleted; (5)–(8) hexon with a FLAG octamer epitope (i.e., Asp Tyr Lys Asp Asp Asp Asp Lys (SEQ ID NO:50]; Hopp et al., *Biotechnology*, 6, 1205–1210 (1988)) substituted for l1, l2, or both l1 and l2, or any one or more of HVR1, HVR2, HVR3, HVR4, HVR5, HVR6 or HVR7; (9)–(12) hexon with a FLAG octamer epitope [SEQ ID NO:50] inserted into l1, l2, or both l1 and l2; (13)-(16) hexon with comparable epitopes from Ad7 (group B) (GenBank® Data Bank Accession Number x76551 for Ad7 hexon, and Number M73260 for Ad5 hexon) or Ad2, or any other adenoviral serotype, substituted for l1, l2, both l1 and l2, respectively, or for any one or more of HVR1, HVR2, HVR3, HVR4, HVR5, HVR6, or HVR7; (17)–(20) hexon with comparable epitopes from Ad7 (group B) (GenBank® Data Bank Accession Number x76551 for Ad7 hexon, and Number M73260 for Ad5 hexon) or Ad2, or any other adenoviral serotype, inserted into l1, l2, both l1 and l2, respectively, or any one or more of HVR1, HVR2, HVR3, HVR4, HVR5, HVR6, or HVR7; and (21) complete substitution of the hexon from Ad7, or hexon of any other adenoviral serotype, for the Ad5 hexon. The use of the FLAG octamer epitope provides a sequence for incorporation in the chimeric hexon protein that is different from the Ad5 hexon loop sequences, and also provides a positive control using available specific anti-FLAG antibodies (Hopp et al., supra).

These chimeric hexon proteins (and vectors containing them) can be made in several steps. To modify the hexon in the "pure 5" vector, a viral or plasmid vector can be constructed to contain the hexon type 5 coding sequence in a cassette that can be easily modified. The hexon is read off the 1 strand of the L3 transcription unit, i.e., map units 51.6 to 59.7, comprising a region of about 2.9 kb. The two other transcripts that also are encoded by L3—i.e., polypeptide VI and a 23 kDa protein—do not overlap the hexon coding sequence. Moreover, there are no other coding sequences on the r strand that would be altered by the modification of the hexon coding sequence.

Thus, all the modifications of the type 5 hexon can be made using a "hexon 5 cassette" comprised of an approximate 6.7 kb SfiI-SfiI fragment of the "pure 5" CAT vector. SfiI cuts Ad5 into 3 fragments, the center 6.7 kb fragment (i.e., comprising about 16,282 to 22,992 base pairs, as identified by agarose gel electrophoresis) of which contains all of the L3 region plus some overlap. The "hexon 5 cassette" can be subcloned into a commercially available vector having restriction sites and the like making the vector easily manipulable in terms of modification and recovery of subcloned sequences. One such vector appropriate for subcloning is either the SK or KS version of the pBlueScript® phagemid (Stratagene, Lajolla, Calif.).

The "hexon 5 cassette" can be mutagenized to generate site-specific mutations in the cloned DNA segment. Several methods are available for carrying out site-specific mutagenesis. The l1 and l2 deletions, insertions, or replacements (or deletions, insertions, or replacements in HVR1, HVR2, HVR3, HVR4, HVR5, HVR6, or HVR7 regions contained therein) can be made by deleting the relevant sequences using restriction enzymes that cut uniquely within the vector inserts, or other similar means, e.g., by ligating in an end-polished, or otherwise modified, PCR product. Alternately, the hexon sequence contained in the hexon 5 cassette can be modified, e.g., using single-stranded mutagenesis in M13mp8 or some other convenient vector, and using appropriate oligonucleotides encompassing the flanking sequences for identification of plaques as described by Crompton et al., supra. Alternately, a commercially available kit such as the ExSite™ PCR-based site-directed mutagenesis kit and the Chameleon™ double-stranded site-directed mutagenesis kit by Stratagene can be used to introduce insertions, point mutations, or deletions into the chimeric hexon sequence without any need for subcloning into an M13, or other special vector.

Similarly, the FLAG octapeptide sequence (Hopp et al., supra) can be introduced into the vectors (i.e., in the presence or absence of any deletion) by inserting the relevant 24 base pair sequence (GAY TAY AAR GAY GAY GAY GAY AAR [SEQ ID NO:50], wherein Y is C or T/U, and R is A or G)). The replacement of Ad5 loop epitopes with comparable sequences of Ad7, Ad2, or any other adenoviral serotype, or an incorporation of these sequences in the absence of any deletion, can be accomplished by using unique restriction sites, or using one of the aforementioned means of mutagenesis.

EXAMPLE 5

This example describes the method of replacing the hexon protein of one serotype adenoviral vector with the hexon protein of another serotype adenoviral vector to generate a recombinant adenovirus. As representative of this method, the hexon protein of an Ad5 vector was replaced with the hexon protein of an Ad7 vector. This example also describes the method of incorporating the chimeric hexon proteins of the preceding Example into a vector to make a recombinant adenovirus.

The Ad5 hexon gene open reading frame (ORF) was replaced with the Ad7 (i.e., Ad7A) hexon gene ORF in such a fashion so as to maintain the proper Ad5 sequences upstream and downstream of the hexon gene. First, Ad5 genomic DNA was digested with HindIII and KpnI. The HindIII-KpnI fragment containing the hexon gene and flanking DNA (i.e., m.u. 50.9–61.6) was subcloned into pBlueScript® SK (pBS SK) to generate pBSH5. Next, the BamHI site in the polylinker of pBSH5 was deleted by digesting the plasmid with EcoRV and SpeI, filling in the ends, and circularizing the plasmid to generate pH5. Then the ClaI-BamHI subgenomic fragment of Ad7A (i.e., comprising the Ad7 hexon ORF from nucleotide 12 to 2676, where nucleotide 1 corresponds to the adenine in the ATG initiation codon) was subcloned into pBS SK to generate pH7.int. Next, a new ClaI site was engineered at map unit 52.33 of Ad5 with use of the polymerase chain reaction (PCR) and the primers HexonCas1 CACACACCCGTAACGCTGGAC [SEQ ID NO:51] and HexonCas2 GGGGGGATCGATG-GCGCGCGGCGGCYCAGCAGCT [SEQ ID NO:52]. A new ClaI site is created in the non-translated region between hexon and protein VI by the right-hand primer HexonCas2. The resultant PCR-amplified fragment comprising the Ad5 sequence immediately upstream of the hexon ORF is HexCas 1.2.

HexCas 1.2 was subcloned into pH7.int by means of sticky end/blunt end cloning. Namely, HexCas 1.2 was digested with ClaI and BstNI. The plasmid pH7.int was cut with ClaI and KpnI. The HexCas 1.2 ClaI site was ligated to the ClaI site of pH7.int. The plasmid was circularized by blunting the KDnI and BstNI ends with T4 polymerase and ligating the blunt ends. The resultant plasmid is pH7.int2. The Ad7 hexon fragment from pH7.int2 was subcloned into plasmid pH5 to yield pH5–7.int by making use of the ClaI and BamHI sites. Finally, a synthetic linker was inserted at the ClaI site of pH5–7.int to complete the Ad7 hexon ORF (i.e., nucleotides 1 to 12) and yield pH5–7. The synthetic linker was made of two partially homologous oligonucleotides: Hex57jxna comprising CGA TCC AAG ATG GCC ACC CCA T [SEQ ID NO:53], and Hex5–7jxnb comprising CGA TGG GGT GGC CAT CTT GGA T [SEQ ID NO:54].

The "hexon-modified" CAT-expressing adenoviral vectors, or adenoviral vectors comprising any of the chimeric hexon proteins in the former Example, can be constructed by homologous recombination using standard techniques and the transformed human embryonic kidney packaging cell line 293 (Rosenfeld et al. (1991), supra; Rosenfeld et al. (1992), supra). For instance, map units 0 to 57.3 of dlAd5NCAT (Gall et al., supra) can be isolated by Bsu36I digestion, and map units 58.4 to 100 of dlAd5NCAT can be isolated by DrdI digestion. These DNA fragments can be transfected into 293 cells along with pH5–7.

Similarly, vectors (particularly adenoviral vectors) can be constructed that have the aforementioned hexon modifications, and which have further modifications, for instance, in the adenoviral fiber coding sequences. This can be accomplished by making the hexon modifications described above, and using different parental plasmids for homologous recombination, such as parental plasmids comprising mutations in fiber coding sequences. In particular, the "5 base/7 fiber" vector can be employed as a starting vector for vector construction.

All of the viral vectors prepared according to this example can be plaque-purified, amplified, and further purified using standard methods (Rosenfeld et al. (1991), supra; Rosenfeld et al. (1992), supra).

EXAMPLE 6

This example describes a characterization of the activity in vitro and in vivo of the vectors described in the preceding Examples.

Each of the viruses prepared as described in the preceding Examples can be evaluated in vitro and in vivo using standard methods as previously described (e.g., Kass-Eisler et al., supra), and as set forth herein. In particular, for the in vitro studies, the various vectors along with control vectors (e.g., the "pure 5" and "5 base/7 fiber" vectors, and the Ad5 wild-type vector) can be added to human lung carcinoma A549 cells alone, or in the presence of dilutions of serum from hosts infected with Ad5, Ad7, "pure 5" CAT vector, or "5 base/7 fiber" CAT vector, or anti-FLAG epitope serum. The cells are then evaluated for CAT activity to determine the ability of antibodies present in the serum to block gene expression.

The in vivo studies can be carried out in Sprague-Dawley rats. The Sprague-Dawley rat as opposed to the mouse or cotton rat is preferred for these experiments since the rat is non-permissive, and the wild-type adenovirus cannot replicate in this host. Accordingly, immunizations can be carried out using wild-type viruses (e.g., wild-type Ad5 or Ad7), the "pure 5" CAT vector, and the "5 base/7 fiber" CAT vector by intravenous administration (e.g., Kass-Eisler et al., supra). At various times ranging from about one to about four weeks later, the vector of interest can be administered intravenously or directly into the airways of the host. Whereas intravenous administration allows an assessment of the "worst case scenario" (i.e., wherein the vector is in immediate contact with the circulating humoral immune system, and thus the strongest immune response is to be expected), introduction in the airways of the host allows an evaluation of a compartmentalized and mucosal humoral immune response.

CAT activity can be quantified as previously described in all the relevant organs, e.g., liver, heart, and lung for intravenous administration, and lung only for respiratory administration. Appropriate standards can be used to compensate for variations in organ expression of CAT activity (see e.g., Kass-Eisler et al., *Gene Therapy*, 2 395–402 (1994)). The in vitro and in vivo results can be compared and assessed using standard statistical methods.

All of the references cited herein, including the GenBank® Data Bank sequence information, are hereby incorporated in their entireties by reference.

While this invention has been described with emphasis upon preferred embodiments, it will be obvious to those of ordinary skill in the art that the preferred embodiments can be varied. It is intended that the invention can be practiced otherwise than as specifically described herein. Accordingly, this invention includes all modifications encompassed within the spirit and scope of the appended claims.

What is claimed is:

1. A chimeric adenovirus coat protein, comprising a non-native amino acid sequence, which comprises a non-hexon amino acid sequence, wherein said chimeric adenovirus coat protein has a decreased ability or inability to be recognized by a neutralizing antibody directed against a corresponding wild-type adenovirus coat protein.

2. The chimeric adenovirus coat protein of claim 1, wherein said non-hexon amino acid sequence comprises a deletion or a substitution of from about 1 to about 750 amino acids of any region of said wild-type adenovirus coat protein or the insertion of from about 1 to about 750 amino acids.

3. The chimeric adenovirus coat protein of claim 1, wherein said non-hexon amino acid sequence comprises a spacer region of from about 1 to about 750 amino acids.

4. The chimeric adenovirus coat protein of claim 2, wherein said coat protein is a chimeric adenovirus hexon protein.

5. A method of constructing an adenoviral vector that has a decreased ability or inability to be recognized by a neutralizing antibody directed against a corresponding wild-type adenovirus coat protein, which method comprises obtaining an adenoviral vector comprising a wild-type adenovirus coat protein and replacing said wild-type adenovirus coat protein with the chimeric adenovirus coat protein of claim 1.

6. The chimeric adenovirus coat protein of claim 2, wherein said non-hexon acid sequence comprises a plurality of deletions, substitutions, or insertions.

7. The chimeric adenovirus hexon protein of claim 5, wherein said hypervariable region comprises a sequence selected from the group consisting of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48.

8. The chimeric adenovirus coat protein of claim 2, wherein said coat protein is a chimeric adenovirus fiber or penton base protein.

9. An adenoviral vector that comprises the chimeric adenovirus coat protein of claim 5.

10. The chimeric adenovirus coat protein of claim 3, wherein said non-hexon amino acid sequence comprises a plurality of spacer regions.

11. The adenoviral vector of claim 10, wherein said solution containing a neutralizing antibody comprises serum of an animal that has been administered an identical vector that comprises a wild type coat protein in place of said chimeric adenoviral coat protein.

12. The chimeric adenovirus coat protein of claim 2, wherein said deletion comprises the entirety of the l1 loop and l2 loop.

13. The chimeric adenovirus coat protein of claim 3, wherein said spacer region is a non-adenoviral protein.

14. The chimeric adenovirus coat protein of claim 3, wherein said coat protein is chimeric adenovirus fiber or penton base protein.

15. The chimeric adenovirus coat protein of claim 2, wherein said nonnative amino acid sequence further comprises a replacement of said deletion with a spacer region of from about 1 to about 750 amino acids.

16. The chimeric adenovirus coat protein of claim 15, wherein said nonnative amino acid sequence comprises a plurality of deletions and replacements.

17. The chimeric adenovirus coat protein of claim 15, wherein said spacer region comprises the sequence of SEQ ID NO:50.

18. The chimeric adenovirus coat protein of claim 7, wherein said non-hexon amino acid sequence is within a hypervariable region in the l1 loop or the l2 loop.

19. The chimeric adenovirus coat protein of claim 18, wherein said spacer region is from a chimeric adenovirus hexon protein.

20. The chimeric adenovirus hexon protein of claim 19, wherein said spacer region is a hypervariable region in the l1 loop or the l2 loop.

21. The chimeric adenovirus hexon protein of claim 20, wherein said hypervariable region is selected from the group consisting of HVR1, HVR2, HVR3, HVR4, HVR5, HVR6, and HVR7.

22. An adenoviral vector that comprises the chimeric adenovirus coat protein of claim 13.

23. An adenoviral vector that comprises the chimeric adenovirus coat protein of claim 20.

24. The chimeric adenovirus hexon protein of claim 19, wherein said spacer region comprises the entirety of the l1 loop and l2 loop.

25. An adenoviral vector that comprises the chimeric adenovirus coat protein of claim 24.

26. An adenoviral vector that comprises the chimeric adenovirus coat protein of claim 18.

27. An adenoviral vector that comprises the chimeric adenovirus coat protein of claim 15.

28. The chimeric adenovirus coat protein of claim 18, wherein said non-hexon amino acid sequence substitutes for the entirety of the l1 loop or the l2 loop.

29. An adenoviral vector that comprises the chimeric adenovirus coat protein of claim 2.

30. A host cell comprising the vector of claim 29.

31. The chimeric adenovirus coat protein of claim 1, wherein said nonnative amino acid sequence comprises an insertion into a region of said coat protein of a spacer region of from about 1 to about 750 amino acids.

32. The chimeric adenovirus coat protein of claim 31, wherein said nonnative amino acid sequence comprises a plurality of insertions.

33. A chimeric adenovirus fiber or penton base protein comprising a nonnative amino acid sequence, wherein said chimeric adenovirus fiber or penton base protein has a decreased ability or inability to be recognized by a neutralizing antibody directed against a corresponding wild-type adenovirus fiber or penton base protein.

34. The chimeric adenovirus fiber or penton base protein of claim 33, wherein said nonnative amino acid sequence comprises a deletion or a replacement of from about 1 to about 750 amino acids of any region of said wild-type adenovirus fiber or penton base protein or the insertion of from about 1 to about 750 amino acids into said wild-type adenovirus fiber or penton base protein.

35. The chimeric adenovirus fiber or penton base protein of claim 33, wherein said nonnative amino acid sequence comprises a spacer region of from about 1 to about 750 amino acids.

36. An adenoviral vector that comprises the chimeric adenovirus fiber or penton base protein of claim 33.

37. A method of constructing an adenoviral vector that has a decreased ability or inability to be recognized by a neutralizing antibody directed against a corresponding wild-type adenovirus fiber or penton base protein, which method comprises obtaining an adenoviral vector comprising a wild-type adenovirus fiber or penton base protein and replacing said wild-type adenovirus fiber or penton base protein with the chimeric adenovirus fiber or penton base protein of claim 33.

38. The chimeric adenovirus fiber or penton base protein of claim 34, wherein said nonnative amino acid sequence comprises a plurality of deletions, replacements, or insertions.

39. An adenoviral vector that comprises the chimeric adenovirus fiber or penton base protein of claim 34.

40. The chimeric adenovirus fiber or penton base protein of claim 35, wherein said spacer region comprises the sequence of SEQ ID NO:50.

41. Teh chimeric adenovirus fiber or penton base protein of claim 35, wherein said spacer region comprises a coat region of another serotype of adenovirus.

42. The chimeric adenovirus fiber or penton base protein of claim 35, wherein said spacer region comprises a non-adenoviral protein.

43. An adenoviral vector that comprises the chimeric adenovirus fiber or penton base protein of claim 35.

44. A host cell comprising the vector of claim 36.

45. The adenoviral vector of claim 36, wherein said vector, when contacted to a host cell in contact with a solution containing a neutralizing antibody, directs at least about 10% greater expression of a passenger gene when compared to the expression of said passenger gene carried by an identical vector that comprises wild-type fiber or penton base protein in place of said chimeric adenovirus fiber or penton base protein.

46. A host cell comprising the vector of claim 39.

47. A host cell comprising the vector of claim 43.

48. The adenoviral vector of claim 45, wherein said solution containing a neutralizing antibody comprises serum of an animal that has been administered an identical vector that comprises a wild type fiber or penton base protein in place of said chimeric adenovirus fiber or penton base protein.

* * * * *

UNITED STATES PATENT AND TRADEMARK OFFICE
CERTIFICATE OF CORRECTION

PATENT NO. : 6,127,525  Page 1 of 1
DATED : October 3, 2000
INVENTOR(S) : Ronald G. Crystal, Erik Falck-Pedersen, Jason Gall, Imre Kovesdi, and Thomas J. Wickham It is certified that error appears in the above-identified patent and that said Letters Patent is hereby corrected as shown below:

Column 4,
Line 40, please delete "Ads" and substitute therefore -- Ad6 --.

Column 7,
Line 6, please delete "NO:81" and substitute therefore -- NO:8] --.
Line 30, please delete "Ads" and substitute therefore -- Ad5 --.

Column 9,
Line 18, please delete the second occurrence of "NO:32" and substitute therefor
-- NO:36 --.

Column 13,
Line 40, please delete "Me." And substitute therefor -- Ma --.
Lines 42-43, please delete "Chameleona" And substitute therefor -- Chameleon ™ --.

Column 24,
Line 63, please delete "Ads" And substitute therefor -- Ad5 --.

Column 26,
Line 67, please delete "Ads" And substitute therefor -- Ad5 --.

Column 27,
Line 45, please delete "KDnI" and substitute therefor -- KpnI --.

Claims,
Line 7, please change the dependency from "claim 5" to -- claim 18 --.

Signed and Sealed this

Eighteenth Day of June, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO.    : 6,127,525
DATED         : October 3, 2000
INVENTOR(S)   : Ronald G. Crystal et al.

It is certified that error appears in the above-identified patent and that said Letters Patent is hereby corrected as shown below:

Column 4,
Line 40, please delete "Ads" and substitute therefore -- Ad6 --.

Column 7,
Line 6, please delete "NO:81" and substitute therefore -- NO:8] --.
Line 30, please delete "Ads" and substitute therefore -- Ad5 --.

Column 9,
Line 18, please delete the second occurrence of "NO:32" and substitute therefor
-- NO:36 --.

Column 13,
Line 40, please delete "Me." And substitute therefor -- Ma --.
Lines 42-43, please delete "Chameleona" And substitute therefor -- Chameleon ™ --.

Column 24,
Line 63, please delete "Ads" And substitute therefor -- Ad5 --.

Column 26,
Line 67, please delete "Ads" And substitute therefor -- Ad5 --.

Column 27,
Line 45, please delete "KDnI" and substitute therefor -- KpnI --.

UNITED STATES PATENT AND TRADEMARK OFFICE
CERTIFICATE OF CORRECTION

PATENT NO. : 6,127,525
DATED : October 3, 2000
INVENTOR(S) : Ronald G. Crystal, Erik Falck-Pedersen, Jason Gall, Imre Kovesdi, and Thomas J. Wickham It is certified that error appears in the above-identified patent and that said Letters Patent is hereby corrected as shown below:

Column 103,
Line 38, please change the dependency from "claim 5" to -- claim 18 --.

This certificate supersedes Certificate of Correction issued June 18, 2002.

Signed and Sealed this

Twenty-first Day of January, 2003

JAMES E. ROGAN
*Director of the United States Patent and Trademark Office*